(12) United States Patent
Bell et al.

(10) Patent No.: US 7,846,960 B2
(45) Date of Patent: Dec. 7, 2010

(54) FXR AGONISTS

(75) Inventors: Michael Gregory Bell, Indianapolis, IN (US); Robert Anthony Doti, Indianapolis, IN (US); Michael James Genin, Zionsville, IN (US); Peter Ambrose Lander, Indianapolis, IN (US); Tianwei Ma, Carmel, IN (US); Peter Rudolph Manninen, Brownsburg, IN (US); Jason Matthew Ochoada, Greenwood, IN (US); Fucheng Qu, Carmel, IN (US); Lindsay Scott Stelzer, Indianapolis, IN (US); Ryan Edward Stites, Indianapolis, IN (US); Alan M. Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 106 days.

(21) Appl. No.: 12/296,534

(22) PCT Filed: May 22, 2007

(86) PCT No.: PCT/US2007/069445

§ 371 (c)(1),
(2), (4) Date: Oct. 9, 2008

(87) PCT Pub. No.: WO2007/140183

PCT Pub. Date: Dec. 6, 2007

(65) Prior Publication Data

US 2009/0270460 A1    Oct. 29, 2009

Related U.S. Application Data

(60) Provisional application No. 60/802,920, filed on May 24, 2006, provisional application No. 60/869,995, filed on Dec. 14, 2006.

(51) Int. Cl.
*A61K 31/415*    (2006.01)
*C07D 231/10*    (2006.01)

(52) U.S. Cl. .................................... 514/406; 548/373.1
(58) Field of Classification Search ................. 514/406; 548/373.1
See application file for complete search history.

(56) References Cited

U.S. PATENT DOCUMENTS 5,990,139 A    11/1999    Yano et al.

FOREIGN PATENT DOCUMENTS

| WO | WO 03/015771 | 2/2003 |
| WO | WO 2004/048349 | 6/2004 |
| WO | WO 2005/065683 | 7/2005 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*

* cited by examiner

*Primary Examiner*—Kamal A Saeed
*Assistant Examiner*—Samantha L Shterengarts
(74) *Attorney, Agent, or Firm*—Francis O. Ginah

(57) ABSTRACT

Compounds of formula wherein variables are as defined herein and their pharmaceutical compositions and methods of use are disclosed as useful for treating dyslipidemia and related diseases.

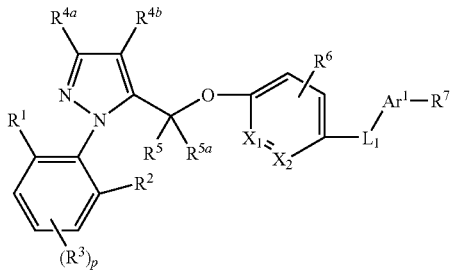

19 Claims, No Drawings

FXR AGONISTS

This application claims the benefit of U.S. Provisional Application Ser. No. 60/802,920, filed 24 May 2006; U.S. Provisional Application Ser. No. 60/869,995, filed 14 Dec. 2006; and PCT Application Serial No. PCT/US2007/069445, filed 22 May 2007, each hereby incorporated by reference in their entirety.

FIELD OF THE INVENTION

The current invention relates to the fields of medicinal organic chemistry, pharmacology, and medicine. Specifically, the invention relates to novel compounds useful for the treatment of diseases related to dyslipidemia.

BACKGROUND OF THE INVENTION

Dyslipidemia and diseases related to dyslipidemia e.g. atherosclerosis, coronary artery disease, stroke, etc., are major causes of death, morbidity, and economic loss. Plasma lipids, especially cholesterol fractions, are recognized as having a significant role in cardiovascular health. Favorable modulation of plasma lipids such as triglycerides, HDL cholesterol, and LDL cholesterol is desirable.

Numerous efforts are underway to provide safe and efficacious molecular entities for the treatment of diseases related to dyslipidemia. For example, International application WO 2004/048349 A1 discloses compounds useful as farnesoid X receptor (FXR) agonists.

FXR agonists are ligands for a nuclear receptor that regulates the transcription of genes that control triglyceride, cholesterol, and carbohydrate metabolism. The above efforts and others not withstanding, there remains a need to discover and develop compounds that are believed to be (1) potent, (2) efficacious (based on in-vivo models) and/or (3) selective agonists of FXR. Such compounds would be useful for treatment of disorders characterized by or resulting from an undesirable lipid profile including dyslipidemia, atherosclerosis, diabetes and related diseases.

The present invention provides compounds that that are believed to be (1) potent, (2) efficacious (based on in-vivo models) and/or (3) selective agonists of the FXR.

SUMMARY OF THE INVENTION

The present invention provides a compound of formula

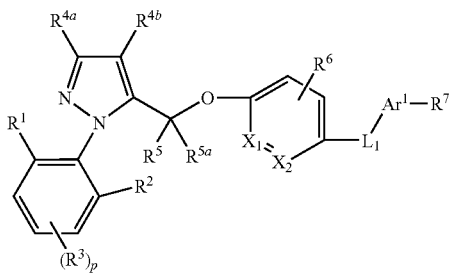

p is 0 or 1 or 2;

$X_1$ is C or N and $X_2$ is C or N; provided that both $X_1$ and $X_2$ are not N;

$R^1$ and $R^2$ are independently selected from the group consisting of hydrogen, $C_1$-$C_6$ alkyl, $C_1$-$C_6$ haloalkyl, $C_1$-$C_6$ alkoxy, $C_1$-$C_6$ haloalkoxy, halo, —S$C_1$-$C_6$ alkyl, and —S—$C_1$-$C_3$ haloalkyl;

each $R^3$ is independently selected from the group consisting of hydrogen, $C_1$-$C_6$ alkyl, $C_1$-$C_6$ haloalkyl, $C_1$-$C_6$ alkoxy, $C_1$-$C_6$ haloalkoxy, and halo;

$R^{4a}$ is selected from the group consisting of hydrogen, $C_1$-$C_6$ alkyl, $C_1$-$C_6$ haloalkyl, $C_3$-$C_8$ cycloalkyl, $C_4$-$C_8$ alkylcycloalkyl, $C_1$-$C_6$ alkoxy, and $C_1$-$C_6$ haloalkoxy;

$R^{4b}$ is selected from the group consisting of hydrogen, $C_1$-$C_6$ alkyl, $C_1$-$C_6$ haloalkyl, $C_3$-$C_8$ cycloalkyl, $C_4$-$C_8$ alkylcycloalkyl, $C_1$-$C_6$ alkoxy, and $C_1$-$C_6$ haloalkoxy;

$R^5$ and $R^{5a}$ are independently selected from the group consisting of hydrogen, and $C_1$-$C_3$ alkyl;

$R^6$ is selected from the group consisting of hydrogen, $C_1$-$C_6$ alkyl, $C_1$-$C_6$ haloalkyl, halo, $C_1$-$C_6$ alkoxy, $C_1$-$C_6$ haloalkoxy, $NO_2$, $C_3$-$C_8$ cycloalkyl, and $C_4$-$C_8$ alkylcycloalkyl;

$L_1$ is selected from the group consisting of a bond, $C_1$-$C_6$ alkyl, $CR^a$=$CR^b$, ethynyl, $C_1$-$C_5$ alkylene, $C_1$-$C_5$ alkyl-S—, $C_1$-$C_5$ alkyl-O—, $N(R^c)$—$C_1$-$C_5$ alkyl, and —$C_1$-$C_5$ alkyl-N($R^c$)—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl and $C_4$-$C_8$ alkylcycloalkyl;

$Ar^1$ is selected from the group consisting of indolyl, thienyl, benzothienyl, naphthyl, phenyl, pyridinyl, pyrazolyl, oxazolyl, benzoisoxazolyl, benzofuranyl, pyrrolyl, thiazolyl, benzoisothiazolyl, indazolyl, and furanyl, each optionally substituted with one or two groups independently selected from the group consisting of hydroxy, $C_1$-$C_6$ alkyl, $C_1$-$C_6$ haloalkyl, halo, $C_2$-$C_6$ alkenyl, $C_2$-$C_6$ alkynyl, $C_1$-$C_6$ alkoxy, —$OC_1$-$C_2$ alkylphenyl, $N(R^c)SO_2C_1$-$C_6$ alkyl, —C(O)$R^{10}$, and NHC(O)$R^{10}$;

$R^7$ is selected from the group consisting of COOH, $C_1$-$C_5$ alkylCOOH, —O—$C_1$-$C_5$ alkylCOOH, $C_2$-$C_4$ alkenyl-COOH, $C_3$-$C_8$ cycloalkylCOOH, and $CONR^{11}R^{11}$;

each $R^{10}$ is independently selected from the group consisting of hydrogen, $C_1$-$C_6$ alkyl, and phenyl;

each $R^{11}$ is independently hydrogen, or $C_1$-$C_6$ alkyl; or a pharmaceutically acceptable salt thereof.

The compounds of the present invention are agonists of FXRs. The compounds of present invention are useful for beneficially altering lipid profiles, including lowering total cholesterol, lowering LDL cholesterol, lowering VLDL cholesterol, raising HDL levels, and lowering triglyceride levels. Thus the present invention provides a method for treating FXR mediated conditions such as dyslipidemia and diseases related to dyslipidemia comprising administering a therapeutically effective amount of a compound of present invention to a patient in need thereof.

The present invention provides a pharmaceutical composition comprising a compound of the present invention and a pharmaceutically acceptable carrier.

The present invention relates to the use of a compound according to the invention for lowering total cholesterol, lowering LDL cholesterol, lowering VLDL cholesterol, raising HDL levels, and/or lowering triglyceride levels comprising administering a therapeutically effective amount of a compound of present invention to a patient in need thereof.

The present invention relates to the use of a compound according to the invention for treating FXR mediated conditions such as dyslipidemia and diseases related to dyslipidemia comprising administering a therapeutically effective amount of a compound of present invention to a patient in need thereof.

The present invention also relates to the use of a compound of the present invention for the manufacture of a medicament.

DETAILED DESCRIPTION OF THE INVENTION

The term "dyslipidemia" as used herein refers to abnormality in, or abnormal amounts of lipids and lipoproteins in the blood and the disease states resulting, caused by, exacerbated by or adjunct to such abnormality (see *Dorland's Illustrated Medical Dictionary*, 29th edition, W.B Saunders publishing Company, New York, N.Y.). Disease states encompassed within the definition of dyslipidemia as used herein include hyperlipidemia, hypertriglyceremia, low plasma HDL, high plasma LDL, high plasma VLDL, liver cholestosis, and hypercholesterolemia.

The phrase "diseases related to dyslipidemia" as used herein refers to diseases including but not limited to atherosclerosis, thrombosis, coronary artery disease, stroke, and hypertension. Diseases related to dyslipidemia also include metabolic diseases such as obesity, diabetes, insulin resistance, and complications thereof. Complications of diabetes include for example, diabetic retinopathy.

As used herein, the term "patient" refers to humans, companion animals (e.g. dogs and cats and the like), and livestock animals.

The terms "treatment" "treat" and "treating" include ameliorating, halting, restraining, slowing, and reversing the progression of, or reducing the severity of pathological symptoms of dyslipidemia and diseases related to dyslipidemia.

As used herein, the term "therapeutically effective amount" means an amount of a compound of the invention that is part of an approved therapeutic regimen, or is determined by a qualified prescriber to be sufficient taken as directed, for treating a condition, or detrimental effects thereof herein described.

The term "pharmaceutically acceptable" is used herein as an adjective and means substantially non-deleterious to the recipient patient.

The term "$C_1$-$C_6$ alkyl" represents a straight or branched hydrocarbon moiety having from 1 to 6 carbon atoms, including but not limited to methyl, ethyl, n-propyl, isopropyl, n-butyl, isobutyl, sec-butyl, t-butyl, and the like. Similarly, the term "$C_1$-$C_5$ alkyl" represents a straight or branched hydrocarbon moiety having from 1 to 5 carbon atoms, including but not limited to methyl, ethyl, n-propyl, and isopropyl. It is understood by one of skill in the art that a "$C_1$-$C_6$ alkyl" or the like is synonymous with a "$C_1$-$C_6$ alkylene" or the like, a diradical when the "$C_1$-$C_6$ alkyl" group is sandwiched between two groups such that it is becomes a diradical.

The term "$C_1$-$C_3$ alkyl" represents a straight or branched hydrocarbon moiety having from 1 to 3 carbon atoms, including methyl, ethyl, n-propyl, and isopropyl. It is understood by one of skill in the art that a "$C_1$-$C_3$ alkyl" is synonymous with a "$C_1$-$C_3$ alkylene" a diradical when the "$C_1$-$C_3$ alkyl" group is sandwiched between two groups such that it is becomes a diradical.

The term "$C_2$-$C_6$ alkenyl" represents a straight or branched hydrocarbon moiety having at least one double bond and having from 2 to 6 carbon atoms. Examples include but are not limited to vinyl, propenyl, and 2-butenyl. Similarly, the term "$C_2$-$C_4$ alkenyl" represents a straight or branched hydrocarbon moiety having at least one double bond and having from 2 to 4 carbon atoms.

The term "$C_2$-$C_6$ alkynyl" or the like represents a straight or branched hydrocarbon moiety having at least one triple bond and having from 2 to 6 carbon atoms. Examples include but are not limited to ethynyl, propynyl, 2-butynyl, and the like. Similarly, the term "$C_2$-$C_4$ alkynyl" or the like represents a straight or branched hydrocarbon moiety having at least one triple bond and having from 2 to 4 carbon atoms.

The term "$C_3$-$C_8$ cycloalkyl" refers to a saturated carbocyclic ring having from 3 to 8 carbon atoms including but not limited to cyclopropyl, cyclopentyl and cyclohexyl. Similarly, the term "$C_3$-$C_6$ cycloalkyl" refers to a saturated carbocyclic ring having from 3 to 6 carbon atoms including cyclopropyl, cyclobutyl, cyclopentyl and cyclohexyl.

The term "$C_4$-$C_8$ alkylcycloalkyl" as used herein refers to the combination of an alkyl and a cycloalkyl group such that the total number of carbon atoms is 4 to 8 or as indicated. For example, $C_4$-$C_8$ alkylcycloalkyl includes cycloalkyl rings bonded to at least one carbon atom, such that the total number of carbon atoms is anywhere from 4 to 8. Similarly, the term "$C_4$-$C_5$ alkylcycloalkyl" as used herein refers to the combination of an alkyl and a cycloalkyl group such that the total number of carbon atoms is 4 to 5. For example, $C_4$-$C_5$ alkylcycloalkyl includes —$CH_2$-cyclopropyl, i.e. methylenecyclopropyl which is $C_4$ alkylcycloalkyl.

The term "$C_1$-$C_6$ haloalkyl" refers to a $C_1$-$C_6$ alkyl group substituted with one, two, three or more halogen atoms as indicated or chemically appropriate. Examples of $C_1$-$C_6$ haloalkyl include but are not limited to trifluoromethyl, chloroethyl, and 2-chloropentyl. Similarly, the term "$C_1$-$C_3$ haloalkyl" refers to a $C_1$-$C_3$ alkyl group substituted with one, two, three or more halogen atoms as indicated or chemically appropriate. Examples of $C_1$-$C_3$ haloalkyl includes but is not limited to trifluoromethyl, chloroethyl, and 2-chloropropyl.

A "$C_1$-$C_6$ alkoxy" group is a $C_1$-$C_6$ alkyl moiety connected through an oxy linkage. Examples of alkoxy groups include but are not limited to methoxy (—OMe), ethoxy(—OEt), propoxy (—OPr), isopropoxy (—OiPr), and butoxy (—OBu). Similarly, the term "$C_1$-$C_3$ alkoxy" group is a $C_1$-$C_3$ alkyl moiety connected through an oxy linkage. $C_1$-$C_3$ alkoxy groups include methoxy (—OMe ($OCH_3$)), ethoxy (—OEt (—$OCH_2CH_2$)), propoxy (—OPr (—$OCH_2CH_2CH_2$)), and isopropoxy (—OiPr (—$OCHCH_3CH_3$)).

The term "$C_1$-$C_5$ alkyl-O—" referred to as $C_1$-$C_5$ alkyloxy represents an alkyl group ($C_1$-$C_5$ alkyl or as indicated) terminating in an oxygen atom as distinct from alkoxy (—O—$C_1$-$C_5$ alkyl) reading from left to right. For example radicals or groups such as —$CH_2O$—, —$CH_2CH_2O$—, and —$CH(CH_3)$O— are herein classified as alkyloxy groups. Similarly, the term "—$C_1$-$C_3$ alkyl-O—" referred to as $C_1$-$C_3$ alkyloxy represents a $C_1$-$C_3$ alkyl group terminating in an oxygen atom as distinct from alkoxy (—O—$C_1$-$C_3$ alkyl) reading from left to right. For example radicals or groups such as —$CH_2O$—, —$CH_2CH_2O$—, and —$CH(CH_3)O$— are herein classified as alkyloxy groups.

The term "$C_1$-$C_6$ haloalkoxy" or the like encompasses alkoxy groups wherein one or more of the hydrogen atoms on the alkyl portion have been replaced with halogens. Examples of haloalkoxy groups include difluoromethoxy, trifluoromethoxy, 2-haloethoxy, 2,2,2-trifluoroethoxy, 4,4,4-trifluorobutoxy, up to and including like groups having the indicated number of carbon atoms. Similarly, the term "$C_1$-$C_3$ haloalkoxy" refers to a $C_1$-$C_3$ alkoxy wherein one or more of the hydrogen atoms on the alkyl portion have been replaced with halogens. Examples of $C_1$-$C_3$ haloalkoxy groups include difluoromethoxy, trifluoromethoxy, 2-haloethoxy, 2,2,2-trifluoroethoxy, up to and including like groups having the indicated number of carbon atoms.

The term "S—$C_1$-$C_6$ alkyl" represents a straight or branched thioalkyl or S-alkyl moiety having from 1 to 6 carbon atoms including but not limited to S-methyl, S-ethyl, S-n-propyl, S-isopropyl, S-n-butyl, S-isobutyl and the like. Similarly, the term "$SC_1$-$C_3$ alkyl" represents a straight or branched thioalkyl or S-alkyl moiety having from 1 to 3 carbon atoms, including S-methyl, S-ethyl, S-n-propyl, and S-isopropyl.

The term "$C_1$-$C_6$ thiohaloalkyl" or "—S—$C_1$-$C_6$ haloalkyl" encompasses —S-alkyl groups wherein one or more of the hydrogen atoms on the alkyl portion have been replaced with halogens. Examples of $C_1$-$C_6$ thiohaloalkyl groups include thiodifluoromethyl, thiotrifluoromethyl, 2-halothioethyl, 2,2,2-trifluorothioethyl, 4,4,4-trifluorobutyl, up to and including like groups having the indicated number of carbon atoms. Similarly, the term "$C_1$-$C_3$ thiohaloalkyl" refers to an S—$C_1$-$C_3$ alkyl wherein one or more of the hydrogen atoms on the alkyl portion have been replaced with halogens. Examples of $C_1$-$C_3$ thiohaloalkyl groups include difluorothiomethyl, trifluorothiomethyl, 2-halothioethyl, 2,2,2-trifluorothioethyl, up to and including like groups having the indicated number of carbon atoms.

The term "—$OC_1$-$C_2$ alkylphenyl" refers to a $C_1$-$C_2$ alkoxy group attached to or substituted on a phenyl group.

It is understood that $R^6$ can be a substituent on $X_1$ or $X_2$ when $X_1$ or $X_2$ is carbon but not when $X_1$ or $X_2$ is nitrogen.

The term "halo" means halogens including iodo, chloro, bromo and fluoro.

It is understood that when $Ar^1$ is bicyclic, attachment of $Ar^1$ to the ring containing $R^6$ can occur at any (chemically) appropriate carbon or nitrogen atom of the bicyclic ring unless otherwise indicated.

A compound of the invention may occur as any one of its isomers all of which are objects of the invention. Certain compounds of the invention may possess one or more chiral centers, and thus, may exist in optically active forms. Likewise, compounds of the invention may have alkenyl groups, and thus, may exist as geometric isomers. All such isomers as well as the mixtures thereof are within the ambit of the present invention. If a particular stereoisomer is desired, it can be prepared by methods well known in the art.

One of skill in the art is aware that where amino groups are present in the compounds of the invention (e.g. when $L^1$ is $N(R^c)CH_2CH_2$—) an acid addition salt of the compound may result in the tetravalent ammonium salt of the compound. For example, reacting an acid such as trifluoroacetic acid with a compound of the invention wherein $L^1$ is an amino group may result in the tetravalent ammonium salt of the compound. All such salts are contemplated and within the purview of the present invention.

PREFERRED EMBODIMENTS OF THE INVENTION

Preferably $X_1$ and $X_2$ are both C. Also preferred is a compound of the invention wherein $X_1$ is N.

Preferably p is 0, or 1. More preferably, p is 0.

Preferably $R^1$ and $R^2$ group are each independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy, —$SC_1$-$C_3$ alkyl, —$SC_1$-$C_3$ haloalkyl, and halo. More preferably, $R^1$ and $R^2$ groups are independently selected from the group consisting of hydrogen, chloro, fluoro, $CF_3$, $OCF_3$, and $SCF_3$.

Preferably, $R^3$ group is absent or is selected from the group consisting of hydrogen, $C_1$-$C_3$ alkyl, $C_1$-$C_3$ haloalkyl, $C_1$-$C_3$ alkoxy, $C_1$-$C_3$ haloalkoxy, and halo. More preferred is an $R^3$ group selected from the group consisting of hydrogen, chloro, fluoro, $CF_3$, $OCF_3$, and $SCF_3$. Most preferably, $R^3$ is absent.

Preferably, $R^{4a}$ is independently selected from H, methyl, ethyl, propyl, isopropyl, cyclopropyl, $CF_3$, and methylcyclopropyl. More preferably, $R^{4a}$ is hydrogen.

Preferably, $R^{4b}$ is independently selected from H, methyl, ethyl, propyl, isopropyl, cyclopropyl, $CF_3$, and methylcyclopropyl. More preferably, $R^{4b}$ is $CF_3$, isopropyl or cyclopropyl.

Preferably, $R^5$ and $R^{5a}$ are each independently selected from the group consisting of hydrogen, methyl and ethyl. More preferably, $R^5$ and $R^{5a}$ are both hydrogen.

A preferred $R^6$ group is selected from the group consisting of hydrogen, halo, $C_1$-$C_3$ alkyl, $C_2$-$C_3$ alkenyl, hydroxy, —$NO_2$, and —$OC_1$-$C_2$ alkyl. More preferably, $R^6$ is selected from the group consisting of hydrogen, halo, methyl, and methoxy. Most preferably, $R^6$ is hydrogen, chloro, or methyl.

Preferred $L_1$ $L_1$ is preferably selected from the group consisting of a bond, CH=CH, ethynyl, —$CH_2S$—, —$C(CH_3)_2$—S—, —$CH(CH_2CH_3)S$—, —$CH(CH_3)S$—, —$CH(CH_3)CH_2$—S—, —$CH(CH_3)CH_2O$—, —$C(CH_3)_2O$—, —$CH(CH_3)O$—, —$CH(CH_2CH_3)O$—, —$N(R^c)(CH_2)_m$—, and —$(CH_2)_m$—$N(R^c)$— wherein $R^c$ is hydrogen or $C_1$-$C_3$ alkyl, m is 1, 2, or 3. More preferably, $L_1$ is a bond, CH=CH, —$N(CH_3)CH_2$, —$N(CH_3)CH_2CH_2$, or —$N(CH_3)CH_2CH_2CH_2$—. More particularly preferred $L_1$ is a bond, —$N(CH_3)CH_2$, or —$N(CH_3)CH_2$. Most preferably $L_1$ is —$N(CH_3)CH_2$ or —$N(CH_3)CH_2CH_2$.

A preferred $Ar^1$ group is selected from the group consisting of optionally substituted indolyl, indazolyl, thienyl, benzothienyl, benzisothiazolyl, phenyl, pyridinyl, pyrrolyl, thiazolyl, and furanyl. More preferably, $Ar^1$ is selected from the group consisting of optionally substituted benzothienyl, indolyl, indazolyl, benzoisothiazolyl, and phenyl. A particularly preferred $Ar^1$ is phenyl, indolyl, benzothienyl, or benzoisothiazolyl. Preferably $Ar^1$ is optionally substituted with one or two groups independently selected from the group consisting of halo, $C_1$-$C_3$ alkyl, $C_1$-$C_3$ alkoxy, $C_1$-$C_3$ haloalkoxy, and $C_1$-$C_3$ haloalkyl.

A preferred $R^7$ substituent is COOH or $CONHR^{11}$. More preferably, $R^7$ is COOH or $CONH_2$, —$CONHCH_3$, or $CONHC_2H_5$. Most preferably $R^7$ is COOH.

Also preferred is a compound of the invention wherein p is 0 or 1 or 2;

$X_1$ is C or N and $X_2$ is C or N; provided that both $X_1$ and $X_2$ are not N;

$R^1$ and $R^2$ are independently selected from the group consisting of hydrogen, $C_1$-$C_3$ alkyl, $C_1$-$C_3$ haloalkyl, $C_1$-$C_3$ thiohaloalkyl, $C_1$-$C_3$ alkoxy, $C_1$-$C_3$ haloalkoxy, and halo;

$R^3$ is absent or independently selected from the group consisting of $C_1$-$C_3$ alkyl, $C_1$-$C_3$ haloalkyl, $C_1$-$C_3$ alkoxy, $C_1$-$C_3$ haloalkoxy, and halo;

$R^{4a}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;

$R^{4b}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;

$R^5$ and $R^{5a}$ are independently selected from the group consisting of hydrogen and $C_1$-$C_3$ alkyl;

$R^6$ is selected from the group consisting of hydrogen, $C_1$-$C_3$ alkyl, $C_1$-$C_3$ haloalkyl, halo, and —$NO_2$;

$L_1$ is selected from the group consisting of a bond, $CR^a$=$CR^b$, ethynyl, $C_1$-$C_3$ alkyl-S—, $C_1$-$C_3$ alkyl-O—, $N(R^c)$—$C_1$-$C_3$ alkyl, and —$C_1$-$C_3$ alkyl-$N(R^c)$—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl, and $C_4$-$C_8$ alkylcycloalkyl;

$Ar^1$ is selected from the group consisting of indolyl, benzothienyl, benzoisothiazolyl, indazolyl, naphthyl, phenyl, pyridinyl, pyrazolyl, pyrrolyl, thienyl, thiazolyl, and furanyl, each optionally substituted with one or two groups independently selected from the group consisting of hydroxy, $C_1$-$C_3$ alkyl, $C_1$-$C_3$ haloalkyl, halo, $C_2$-$C_4$ alkenyl, $C_2$-$C_4$ alkynyl, $C_1$-$C_4$ alkoxy, —$OC_1$-$C_2$ alkylphenyl, —NHC(O)$R^{10}$;

$R^7$ is selected from the group consisting of —COOH, —$C_1$-$C_3$ alkylCOOH, —O—$C_1$-$C_3$ alkylCOOH, and, —$CONR^{11}R^{11}$;

each $R^{10}$ is independently selected from the group consisting of hydrogen, $C_1$-$C_3$ alkyl, and phenyl;

each $R^{11}$ is independently hydrogen, or $C_1$-$C_5$ alkyl; or a pharmaceutically acceptable salt thereof.

Also preferred is a compound of the invention wherein:

p is 0 or 1;

$X_1$ and $X_2$ are both C, or $X_1$ is N and $X_2$ is C;

$R^1$ and $R^2$ are independently selected from the group consisting of hydrogen, fluoro, chloro, $CF_3$, $SCF_3$, $OCF_3$, $R^3$ is fluoro, chloro $C_1$-$C_3$ alkyl, $CF_3$, $SCF_3$, or $OCF_3$;

$R^{4a}$ is hydrogen, methyl, ethyl or isopropyl;

$R^{4b}$ is H, $C_1$-$C_3$ alkyl, $C_1$-$C_3$ haloalkyl, $C_1$-$C_3$ haloalkoxy, or $C_3$-$C_4$ cycloalkyl;

$R^5$ and $R^{5a}$ are each independently selected from H or $C_1$-$C_3$ alkyl;

$Ar^1$ group is phenyl, indolyl, pyridinyl, pyrrolyl, thienyl, naphthyl, thiazolyl, furanyl, pyrazolyl, indazolyl, benzoisothiazolyl, and benzothienyl each optionally substituted with one to two groups independently selected from $C_1$-$C_5$ alkyl, $C_1$-$C_4$ alkoxy, $C_1$-$C_2$ haloalkoxy, and $C_1$-$C_3$ haloalkyl;

$R^6$ is hydrogen, methyl, ethyl or chloro;

$L_1$ is a bond, ethenyl, —CH($CH_3$)—S—, C($CH_3$)$_2$—S—, —$CH_2$O—, —$CH_2CH_2$O—, —CH($CH_3$)—O—, —CH($CH_3$)$CH_2$—O—, —CH($CH_2CH_3$)—O—, —$CH_2$NH—, —$CH_2CH_2$NH—, —$N(R^c)CH_2$—, $N(R^c)CH_2CH_2$—, or $N(R^c)CH_2CH_2CH_2$—; wherein $R^c$ is hydrogen, $C_1$-$C_2$ alkyl, or benzyl;

$R^7$ is COOH, —$CH_2$COOH, —CH($CH_3$)COOH, —C($CH_3$)$_2$COOH, $CONH_2$, C(O)$NHCH_3$, or C(O)$NHCH_2CH_3$;

$R^{10}$ is hydrogen or $C_1$-$C_2$ alkyl; and $R^{11}$ is hydrogen or $C_1$-$C_2$ alkyl, or a pharmaceutically acceptable salt thereof.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $R^5$ and $R^{5a}$ are both hydrogen; $L_1$ is ethenyl, ethynyl, —$N(CH_3)CH_2$—, or —$N(CH_3)CH_2CH_2$—; $R^6$ is hydrogen, methyl, chloro or bromo; $Ar^1$ is phenyl, indolyl, indazolyl, benzothienyl, or benzoisothiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —$N(CH_3)CH_2$—, or —$N(CH_3)CH_2CH_2$—; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 1; $R^1$ and $R^2$ are independently selected from the group consisting of hydrogen, chloro, fluoro, trifluoromethyl, thiotrifluoromethyl, and trifluoromethoxy; $R^3$ is hydrogen; $R^{4a}$ is hydrogen; $R^{4b}$ is trifluoromethyl, isopropyl or cyclopropyl; $L_1$ is —$N(CH_3)CH_2$—, or —$N(CH_3)CH_2CH_2$—; $R^5$ and $R^{5a}$ are both hydrogen; $R^6$ is hydrogen, methyl, ethyl or chloro; $Ar^1$ is phenyl, optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond, —$N(CH_3)CH_2$—, or —$N(CH_3)CH_2CH_2$—; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is ethenyl, —$N(CH_3)CH_2$—, or —$N(CH_3)CH_2CH_2$—; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond, —CH($CH_3$)O, —CH($CH_3$)$CH_2$O, —CH($CH_3$)S, —C($CH_3$)$_2$S, —$CH_2$—NH—, and —$CH_2$N($CH_3$)—; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen;

$R^{4b}$ is trifluoromethyl, isopropyl or cyclopropyl; $L_1$ is ethenyl, —CH(CH$_3$)O—, —CH(CH$_3$)CH$_2$O—, —CH(CH$_3$)S—, —C(CH$_3$)$_2$S—, —CH$_2$—NH—, and —CH$_2$N(CH$_3$)—; $R^5$ and $R^{5a}$ are both hydrogen; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is ethenyl; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

Also preferred is a compound of the invention wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

The compounds of the present invention (i.e. compound of formula I) can be prepared by a variety of procedures known in the art and those described below. The products of each step in the Scheme below can be recovered by conventional methods including extraction, evaporation, precipitation, chromatography, filtration, trituration, crystallization, and the like. In the scheme below all substituents, unless otherwise indicated, are as previously defined and suitable reagents are well known and appreciated in the art.

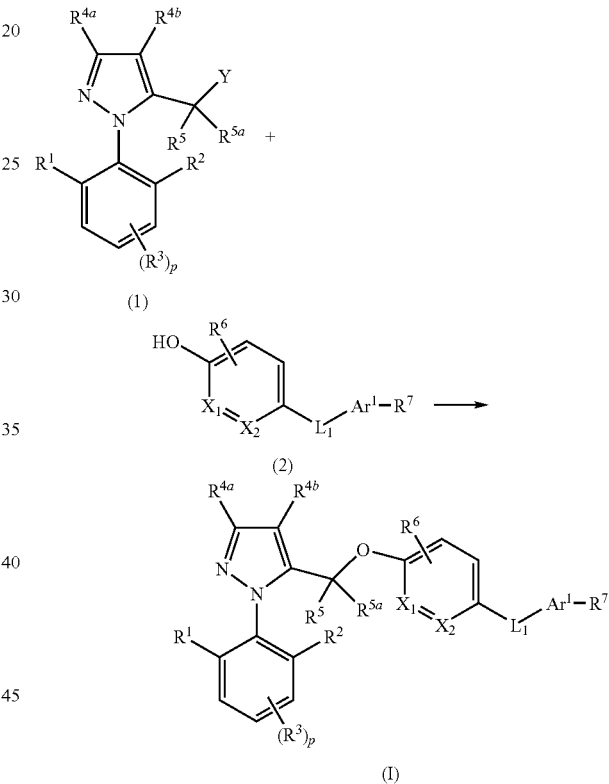

Scheme 1

Scheme 1 depicts the reaction of an appropriate compound of formula (1) with an appropriate compound of formula (2) to give a compound of formula (I). The reaction in Scheme 1 can be carried out by at least two variants discussed below.

In the first variant, an appropriate compound of formula (1) is one in which $R^1$, $R^2$, $R^3$, p, $R^{4a}$, $R^{4b}$, $R^5$, and $R^{5a}$ are defined for formula I, and Y is —OH and an appropriate compound of formula (2) is one in which $R^6$, $R^7$, $X_1$, $X_2$, $L_1$, and $Ar^1$ are as defined in formula (I) or a group which gives rise to $R^7$ as defined in formula (1), for example, by formation of an ester, amide, sulfonamide, or acid.

For example, a compound of formula (1) is reacted with a compound of formula (2) in a Mitsunobu reaction using a suitable diazo reagent, such as DEAD or ADDP, and the like, and a suitable phosphine reagent such as triphenyl phosphine or tributylphosphine, and the like. Such reactions are carried out in a suitable solvent, such as toluene, tetrahydrofuran, and the like. Generally, the reactions are carried out at temperatures of from about 0° C. to 50° C. Typical stoichiometry is for this reaction is, based on the compound of formula (1), about 1 to 2 equivalents of a compound of formula (2) and about 1 to 2 equivalents each of the diazo and phosphine reagents.

In the second variant, an appropriate compound of formula (1) is one in which $R^1$, $R^2$, $R^3$, p, $R^{4a}$, $R^{4b}$, $R^5$, and $R^{5a}$ are defined for formula I and Y is a leaving group and an appropriate compound of formula (2) is as defined above. Suitable leaving groups are well-known in the art and include halides, particularly chloro, bromo, and iodo; and sulfonate esters, such as brosyl, tosyl, methanesulfonyl, and trifluoromethanesulfonyl.

For example, a compound of formula (1) is reacted with a compound of formula (2) in a suitable solvent, such as acetonitrile, dimethylformamide, tetrahydrofuran, pyridine, methylethyl ketone and the like. As will be readily appreciated an excess of a suitable base is usually used in the reaction, including sodium hydride, potassium carbonate, sodium carbonate, cesium carbonate, sodium bicarbonate, triethylamine, diisopropylethylamine. Such reactions generally are carried out at temperatures of about room temperature to about the reflux temperature of the chosen solvent and typically use from about 1 to 2 equivalents of the compound of formula (2).

In an optional step, a pharmaceutically acceptable salt of a compound of formula (I) is formed. The formation of such salts is well known and appreciated in the art.

As will be readily appreciated compounds of formula (1) and (2) can be readily prepared by methods similar to those described herein by procedures that are well-known and established in the art. For example, compounds of formula (1) are prepared by the reaction of optionally substituted phenyl hydrazine with a 1,3-diketoester (or an equivalent thereof) followed by reduction and optionally conversion to a leaving group and compounds of formula (2) are prepared by carbon-carbon bond formation, reductive amination, coupling reaction, etc. Also, it is recognized that the steps required to prepare a compound of formula (2) can be carried out in any order, including after reaction of a partial compound of formula (2) with a compound of formula (1), such that the later carried out carbon-carbon bond formation, reductive amination, coupling reaction, etc, provide a compound of formula I. As will be readily understood the steps to prepare the compounds of formula I is dependent upon the particular compound being synthesized, the starting compound, and the relative liability of the substituted moieties. Also contemplated are various protection and deprotection steps as may be required or beneficial for carrying out the reactions above. The selection and use of suitable protecting groups is well known and appreciated in the art (see for example, *Protecting Groups in Organic Synthesis*, Theodora Greene (Wiley-Interscience)).

The present invention is further illustrated by the following examples and preparations. These examples and preparations are illustrative only and are not intended to limit the invention in any way. The terms used in the examples and preparations have their normal meanings unless otherwise designated.

Assay

The following assay protocols and results demonstrate the utility, in vitro and in vivo efficacy of the compounds and/or methods of the current invention and are provided for the purpose of illustration and not meant to be limiting in any way.

The following abbreviations used herein are defined as follows. "LDL" is: Low Density Lipoprotein; "HDL" is High Density Lipoprotein; "VLDL" is Very Low Density Lipoprotein; "LDLR−/−" is Low Density Lipoprotein receptor deficient; "DMEM" is Dulbecco's Modified Eagle's Medium; "GAPDH" is glyceraldehyde-3-phosphate dehydrogenase; "NaCMC" is sodium carboxymethylcellulose; "SLS" is sodium lauryl sulfate; "FPLC" is fast protein liquid chromatography; "PBS" is phosphate buffered saline; "VLDL-C" is Very Low Density Lipoprotein-Cholesterol; "HDL-C" is High Density Lipoprotein-Cholesterol.

bDNA Assay for SHP mRNA

FXR is a key, direct transcriptional regulator of the Small Heterodimer Partner (SHP) gene, accession number NM_021969, an atypical member of the nuclear receptor family that lacks a DNA-binding domain. SHP interacts with several conventional and orphan members of the nuclear receptor superfamily, including retinoid receptors and thyroid hormone receptor. SHP inhibits transactivation potential of superfamily members with which it interacts. FXR and SHP both have been found to control genes involved in hepatic cholesterol catabolism, triglyceride synthesis, and bile acid transport. Since FXR directly transactivates transcription of the SHP gene, the SHP branched DNA method (bDNA) quantitates FXR activation by ligands. Thus, increased expression of SHP mRNA, as determined by increase bDNA signal, signifies engagement of FXR by an agonist.

Plate human hepatocarcinoma Huh7 cells grown in DMEM:F12 with 10% fetal bovine serum and in 96 well plate at the density of $1 \times 10^5$/well. After overnight incubation, treat the cells with test compounds at various concentrations for 24 hours.

Perform the bDNA assay according to the manufacturer protocol (Panomics, Fremont, Calif.) for the QuantiGene® High Volume Kit. After challenging the cells with a compound of the invention, lyse the cells with QuantiGene® lysis buffer containing the SHP mRNA oligonucleotides described below. Appropriate bDNA oligonucleotide reagents (capture extenders (CEs), label extenders (LEs), and blockers (BLs)) may be designed and synthesized for detecting human SHP mRNA by Panomics (Fremont, Calif.).

Incubate the lysis buffer for 15-minute at 37° C., then transfer 100 µL of the lysate from each well to the corresponding wells of the capture plate. Incubate the capture plate overnight at 53° C. Wash the capture plate twice with QuantiGene® wash buffer followed by addition of 100 µL/well QuantiGene® amplifier working reagent. Incubate the plate for 60 minutes at 46° C. followed by two washes. Label the mRNA to be measured by addition of 100 µL QuantiGene® label probe working buffer then incubate for 60 minutes at 46° C. Wash the capture plate twice and add 100 µL/well QuantiGene® substrate plus QuantiGene® enhancer reagent. Incubate the plates at 37° C. for up to 30 minutes and then read on a luminometer (Packard Fusion Alpha, 1 second detection) to detect the luminescent signal. Calculate $EC_{50}$ values i.e. effective response relative to maximal response.

Exemplified compounds are effective as FXR modulators based on the above assay at an $EC_{50}$ of 2 uM or less. For example the compound of example 90 exhibits SHP gene activation $EC_{50}$ of about 53 nM.

LDLR−/− Serum Lipid Modulation

Acclimate animals for two weeks prior to study initiation. House mice individually in polycarbonate cages with filter tops, and maintain mice on a 12:12 hour light-dark cycle (lights on at 6:00 AM) at 21° C. Provide deionized water ad libitum and maintain for two weeks on 'western diet' TD 88137 Diet (42% fat, 0.15% cholesterol, Harlan Teklad) ad libitum. Optimize groups of five ten-week-old male LDLR−/− mice based on serum triglyceride and cholesterol levels. Dose groups once daily by oral gavage with various doses of the test compound dissolved in 5% EtOH/5% Solutol in NaCMC (1%), SLS (0.5%), antifoam (0.05%), Povidone (0.085%) for seven days. At the end of the seven-day dosing period, collect blood by cardiac puncture after asphyxiation in a $CO_2$ chamber. Measure serum triglycerides, glucose, and total cholesterol using standard clinical chemistry instrumentation and reagents [Hitachi 912 instrument with reagent kits (Roche, Indianapolis, Ind.)]. Assay pooled serum samples by FPLC analysis for lipoprotein cholesterol fraction values (VLDL, LDL, HDL) by separation on a size exclusion column with in-line determination of cholesterol. Lipoproteins were separated by fast protein liquid chromatography, and cholesterol was quantitated with an in-line detection system. Briefly, 35 μL plasma samples/50 μL pooled sample was applied to a Superose 6 HR 10/30 size exclusion column (Amersham Pharmacia Biotech, Piscataway, N.J.) and eluted with PBS, pH 7.4 (diluted 1:10), containing 5 mM EDTA, at 0.5 mL/min. Cholesterol reagent from Roche Diagnostics (Indianapolis, Ind.) at 0.16 mL/min was mixed with the column effluent through a T connection; the mixture was then passed through a 15 m×0.5 mm knitted tubing reactor (Aura Industries, New York, N.Y.) immersed in a 37 C water bath. The colored product produced in the presence of cholesterol was monitored in the flow stream at 505 nm, and the analog voltage from the monitor was converted to a digital signal for collection and analysis. The change in voltage corresponding to change in cholesterol concentration was plotted vs. time, and the area under the curve corresponding to the elution of VLDL-C and HDL-C was calculated using Turbochrome (version 4.12F12) software from PerkinElmer (Norwalk, Conn.).

In this assay, tested compounds of the invention reduce total cholesterol up to 84% and triglycerides up to 86% when dosed at 10 mg/kg. More specifically the compound of Example 199 lowers total cholesterol by 60% and triglycerides by 63% when dosed at 10 mg/kg.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.1 mg to about 1000 mg/day of a compound of the present invention.

The compounds of this invention may be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of the invention, or a pharmaceutically acceptable salt thereof, and a pharmaceutically acceptable carrier, diluent, or excipient.

One skilled in the art can readily select the proper form and route of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions.

Compounds of the invention may be formulated as elixirs or solutions for convenient oral administration or as solutions appropriate for parenteral administration, for example, by intramuscular, subcutaneous or intravenous routes. Additionally, the compounds may be formulated as sustained release dosage forms and the like. The formulations can be constituted such that they release the active ingredient only or preferably in a particular physiological location, possibly over a period of time. The coatings, envelopes, and protective matrices may be made, for example, from polymeric substances or waxes.

PREPARATIONS AND EXAMPLES

The following preparations and examples further illustrate the invention.

The abbreviations used herein are defined according to Aldrichimica Acta, Vol 17, No. 1, 1984. Other abbreviations are defined as follows. "ACN" is acetonitrile; "AcOH" is acetic acid; "MeOH" is methanol; "EtOH" is ethanol; "EtOAc" is ethyl acetate; "$Et_2O$" is diethyl ether; "hex" is hexane; "DCE" is dichloroethane; "DCM" is dichloromethane; "TFA" is trifluoroacetic acid; "$TMSCHN_2$" is (trimethylsilyl)diazomethane; "ADDP" is 1,1-(Azodicarbonyl)dipiperidine; "DPPB" is 1,4 bis-(diphenylphosphino)butane; "dppf" is diphenylphosphinoferrocene; "dba" is dibenzylidineacetone; "TBAI" is tetrabutylammonium iodide; "DIAD" is diisopropyl azodicarboxylate: "OAc" is acetate; "NaOEt" is sodium ethoxide; "$PCy_3$" is tricyclohexyl phosphine.

All compounds are named using ChemDraw Ultra 7.0 available from CambridgeSoft Corporation, Cambridge, Mass., USA.

Preparation 1

4-Methyl-2-oxo-pentanoic Acid Methyl Ester

To a solution of 4-methyl-2-oxo-pentanoic acid (3.4 g, 26 mmol) in methanol (12 mL) and 2,2-dimethoxypropane (48 mL) is added chlorotrimethylsilane (0.38 mL). The reaction mixture is stirred at ambient temperature overnight. The reaction mixture is concentrated under reduced pressure to give the title compound as an oil, (3.8 g, quant.). $^1$H NMR (400 MHz, $CDCl_3$): δ 3.86 (s, 3H), 2.72 (d, 2H), 2.16 (m, 1H), 0.96 (d, 6H).

Preparation 2

2-Methoxyimino-4-oxo-pentanoic Acid Ethyl Ester

A mixture of 2,4-dioxo-pentanoic acid ethyl ester (5.4 mL, 50 mmol), methoxyamine hydrochloride (4.4 g, 52.5 mmol), molecular sieves (3 Å, 35 g) and sodium sulfate (15 g) in ethanol (50 mL) is stirred at ambient temperature for 5 hours. The reaction mixture is filtered and washed with ethanol. The combined filtrate is concentrated under reduced pressure and is partitioned between ethyl ether and saturated sodium bicarbonate. The organic layer is dried ($MgSO_4$), filtered, and concentrated. The residue is purified by column chromatography (0 to 15% EtOAc in hexanes) to give the title compound as a colorless oil (3 g, 32%). $^1$H NMR (400 MHz, CDCl3) δ 4.33 (q, 2H), 4.06 (s, 3H), 3.70 (s, 3H), 2.20 (s, 3H), 1.34 (t, 3H).

Preparation 3

3-Acetyl-2-methoxyimino-5-methyl-hexanoic Acid Ethyl Ester

To a solution of 2-methoxyimino-4-oxo-pentanoic acid ethyl ester (2.62 g, 14 mmol) in DMF (30 mL) is added potassium carbonate (2.5 g, 18.2 mmol) followed by 1-iodo-2-methyl-propane (1.62 mL, 14 mmol) and the mixture is stirred at ambient temperature overnight. Additional 1-iodo-2-methyl-propane (0.8 mL, 7 mmol) is added and the mixture is stirred at 60° C. for 1 hour. The reaction mixture is diluted with EtOAc and is adjusted to pH 3 with 1N HCl. The organic layer is washed with brine, dried ($MgSO_4$), filtered, and concentrated under reduced pressure. The residue is purified by column chromatography (0 to 20% EtOAc in hexanes) to give the title compound as a colorless oil (1 g, 29%). $^1$H NMR (400 MHz, CDCl3) δ 4.33 (q, 2H), 4.06 (s, 3H), 4.03 (dd, 1H), 2.07 (s, 3H), 1.88 (m, 1H), 1.58 (m, 1H), 1.43 (m, 1H), 1.37 (t, 3H), 0.89 (d, 6H).

Preparation 4

2-Cyclopropylmethyl-[1,3]dithiane-2-carboxylic Acid Ethyl Ester

To a flamed dried flask is added dry toluene (80 mL) and sodium hydride (60%, 33.5 mmol, 1.34 g). The reaction is cooled in a ice bath and a solution of ethyl 1,3 dithiane carboxylate (52 mmol, 10 g) and bromomethyl cyclopropane (62.4 mmol, 8.42 g) in DMF (24 mL) are added dropwise over 10 min. The ice bath is removed and the reaction is stirred for 18 h. Water is added (50 mL) and the organic layer is separated. The organic layer is washed with brine, dried ($Na_2SO_4$), and concentrated to a yellow oil (12 g, 92%). LC-MS: 247.0 (M+1).

Preparation 5

3-Cyclopropyl-2-oxo-propionic Acid Ethyl Ester

To a 0° C. suspension of NBS (439 mmol, 79 g) in a mixture of acetonitrile (400 mL) and water (100 mL) is added a solution of 2-cyclopropylmethyl-[1,3]dithiane-2-carboxylic acid ethyl ester (73.2 mmol, 18.05 g) in acetonitrile (50 mL) over 15 minutes. The reaction is warmed and is stirred at room temperature. After 45 minutes, 500 mL of 1:1 hexane/DCM is added. The layers are separated. The organic layer is washed with saturated $Na_2SO_3$ (2×225 mL) and brine (2×225 mL), dried with $Na_2SO_4$, filtered, and concentrated under reduced pressure to a residue. The residue is diluted in $CCl_4$ and is filtered. The filtrate is concentrated to give the title compound (7 g, 61%). LC-MS: 157.0 (M+1).

Preparation 6

3-Cyclobutyl-2-oxo-propionic Acid Ethyl Ester

To a suspension of 5 mg per mL Rieke® magnesium in THF (37.9 mmol, 40 mL) at room temperature is added bromomethyl cyclobutane (37.9 mmol, 4.25 mL) dropwise. After the addition, the reaction is heated to 60° C. for 1 h. The mixture is transferred via syringe to a −78° C. solution of diethyl oxalate (37.9 mmol, 5.14 g) in THF (20 mL). The reaction is allowed to warm to 0° C. and is quenched with 1N HCl. Diethyl ether is added (20 mL) and the layers are separated. The organic layer is dried ($Na_2SO_4$) and adsorbed onto silica and purified using a gradient to 0-10% EtOAc/Hexanes to yield the title compound (2.3 g, 37%). LC-MS: 171.0 (M+1).

Preparation 7

3-Cyclopropyl-4-dimethylamino-2-oxo-but-3-enoic Acid Ethyl Ester

A mixture of 3-cyclopropyl-2-oxo-propionic acid ethyl ester (6.4 mmol, 1.0 g) and dimethylformamide dimethylacetal (12.8 mmol, 2.0 mL) are combined and stirred at room temperature for 18 hours. The reaction is concentrated under reduced pressure to yield the title compound (1.38 g, 100%). LC-MS: 212.0 (M+1).

Preparation 8

3-Cyclobutyl-4-dimethylamino-2-oxo-but-3-enoic Acid Ethyl Ester

The title compound (0.663, 51%) is prepared essentially as described in the preparation of 3-cyclopropyl-4-dimethylamino-2-oxo-but-3-enoic acid ethyl ester using 3-cyclobutyl-2-oxo-propionic acid ethyl ester. LC-ES/MS m/e 226.0 (M+1)

Preparation 9

2-Chloro-6-trifluoromethyl-phenyl)-hydrazine Hydrochloride

To a 0° C. solution of 2-chloro-6-trifluoromethyl-phenylamine (35.7 mmol, 7.0 g) in THF (100 mL) is added 48% $BF_3OEt$ (143 mmol, 36 mL) followed by addition of isoamyl nitrite (143 mmol, 19 mL). The reaction is stirred for 1 hour and is filtered to collect the tetrafluoroborate diazonium salt (48.7 mmol, 9.0 g). The salt is dissolved in a mixture of conc. HCl (30 mL) and water (10 mL) at 0° C. To the resulting mixture is added ascorbic acid (48.7 mmol, 8.5 g). The reaction is heated to 50° C. for 3 hours and cooled to room temperature. The solid is filtered and washed with ice water. The wet solid is dissolved in a mixture of conc. HCl (30 mL) and water (20 mL) and heated to 90° C. for 2 hours. The reaction is cooled to 0° C. and filtered to yield the title compound (5.0 g, 60%). LC-ES/MS m/e 157.0 (M+1).

The following list of compounds is prepared essentially as described in the preparation of 2-chloro-6-trifluoromethyl-phenyl)-hydrazine hydrochloride using the appropriate starting material.

Preparation 9A: 3,5 Difluoro-2-trifluoromethyl-phenylhydrazine hydrochloride, (3.0 g, 25%), LC-ES/MS m/e 159.0 (M+1); Preparation 9B: 2-Fluoro-6-trifluoromethyl-phenylhydrazine hydrochloride (5.2 g, 63%), LC-ES/MS m/e 195.0 (M+1); Preparation 9C: 2-trifluoromethylsulfanyl phenylhydrazine hydrochloride, (0.414 g, 68%), ES/MS m/e 209.0 (M+1).

Preparation 10

2,6 Dichloro-4-fluoro-phenylhydrazine Hydrochloride

To a 0° C. solution of 2,6 Dichloro-4-fluorophenylamine (3.0 g, 16.6 mmol) in 12 M HCl (30 mL) and TFA (20 mL) is added slowly and dropwise $NaNO_2$ (20 mmol, 1.37 mL) in water (6 mL). The reaction is stirred at 0° C. for 1 h. A solution of SnCl$_2$ (5.74 g, 25.6 mmol) in 12 M HCl (16 mL) is added over 15 minutes. The ice bath is removed and the reaction is stirred for 18 h. The reaction is filtered and the solid is washed with isopropyl alcohol. The solid is dried to yield the title compound (3.0 g, 96%). LC-ES/MS m/e 194.0 (M+1)

Preparation 11

(2-Trifluoromethoxy-phenyl)-hydrazine Hydrochloride

To a stirred solution of hydrochloric acid (37%, 1.6 L) at 0° C. is added 2-trifluoromethoxy-phenylamine (200 g, 113 mmol) followed by water (160 mL) and additional hydrochloric acid (160 mL). The mixture is warmed to room temperature, is stirred for 20 minutes, and is cooled to −5° C. A solution of sodium nitrite (82 g, 1.19 mmol) in water (400 mL) is added dropwise keeping the internal temperature below 0° C. The mixture is cooled to −5° C. and a solution of tin (II) chloride dihydrate (1020 g, 4520 mmol) in of HCl (37%, 3.2 L) is added dropwise keeping the internal temperature below 0° C. The mixture is warmed to room temperature, is stirred for 3 h, filtered, and washed with 6 N HCl (3 L) to obtain a yellow solid that is dried under vacuum overnight The title compound (115.8 g, 54%) is obtained pink-brown solid.

Preparation 12

Trifluoromethoxy-phenyl-hydrazine Hydrochloride

The title compound (115.8 g, 54%) is prepared essentially according to the preparation of (2-trifluoromethoxy-phenyl)-hydrazine hydrochloride using 2-trifluoromethoxy-phenylamine.

Preparation 13

2-(2,6-Dichloro-phenyl)-4-isobutyl-5-methyl-2H-pyrazole-3-carboxylic Acid Ethyl Ester A mixture of 3-acetyl-2-methoxyimino-5-methyl-hexanoic acid ethyl ester (1 g, 4.1 mmol), 2,6-dichlorophenylhydrazine hydrochloride (1.76 g, 8.2 mmol) in glacial acetic acid (10 mL) and 2-methoxy-ethanol (5 mL) is stirred at 105° C. for 3 hours. The reaction is concentrated and the residue is partitioned between EtOAc and 1N HCl. The organic layer is concentrated and purified by column chromatography (0-20% EtOAc in hexanes) to give the title product as an oil, 1.1 g (76%).

$^1$H NMR (400 MHz, CDCl3) δ 7.41 (d, 2H), 7.31 (dd, 1H), 4.16 (q, 2H), 2.65 (d, 2H), 2.33 (s, 3H), 1.92 (m, 1H), 1.13 (t, 3H), 0.95 (d, 6H).

Preparation 14

4-Cyclopropyl-2-(2,6-dichloro-phenyl)-2H-Pyrazole-3-carboxylic Acid Ethyl Ester

To a solution of 3-Cycloproply-4-dimethylamino-2-oxo-but-3-enoic acid ethyl ester (6.5 mmol, 1.4 g) in ethanol (25 mL) is added 2,6-dichlorophenyl hydrazine hydrochloride (7.2 mmol, 1.5 g) followed by concentrated HCl (100 µL). The reaction is stirred for 4 h at room temperature followed by heating at 85° C. for 18 h. The reaction mixture is adsorbed onto silica gel and purified using a gradient of 0-20% EtOAc/Hexanes to yield the title compound (0.8 g, 34%). LC-ES/MS m/e 325.0 (M+1).

The following list of compounds is prepared essentially according to the preparation of 4-Cyclopropyl-2-(2,6-dichloro-phenyl)-2H-Pyrazole-3-carboxylic acid ethyl ester using the appropriate starting material.

Preparation 14A: 4-Cyclobutyl-2-(2,6-dichloro-phenyl)-2H-Pyrazole-3-carboxylic acid ethyl ester (0.56 g, 57%), LC-ES/MS m/e 339.0 (M+1); Preparation 14B: 2-(2-Chloro-6-trifluoromethyl-phenyl-4-isopropyl-2H-pyrazole-3-carboxylic acid methyl ester (0.56 g, 10%), LC-ES/MS m/e 293.0 (M+1); Preparation 14C: 2-(3,5-Difluoro-2-trifluoromethyl-phenyl)-4-isopropyl-2H-pyrazol-3-carboxylic acid methyl ester (1.6 g, 60%), LC-ES/MS m/e 295.0 (M+1); Preparation 14D: 2-(2,6-Dichloro-phenyl)-4-isobutyl-5-methyl-2H-pyrazole-3-carboxylic acid ethyl ester (1.1 g, 76%), $^1$H NMR (CDCl3) δ 7.41 (d, 2H), 7.31 (dd, 1H), 4.16 (q, 2H), 2.65 (d, 2H), 2.33 (s, 3H), 1.92 (m, 1H), 1.13 (t, 3H), 0.95 (d, 6H); Preparation 14E: 2-(2-Fluoro-6-trifluoromethyl-phenyl)-4-isopropyl-2H-pyrazole-3-carboxylic acid methyl ester (0.063 g, 67%), LC-ES/MS m/e 277.0 (M+1); Preparation 14F: 2-(2,6-Dichloro-4-fluorophenyl)-4-isopropyl-2H-pyrazol-3-carboxylic acid methyl ester (0.28 g, 39%), LC-ES/MS m/e 331.0 (M+1); Preparation 14G: 4-Isopropyl-2-(2-trifluoromethylsulfanyl-phenyl)-2H-pyrazol-3-carboxylic acid methyl ester (0.25 g, 76%), LC-ES/MS m/e 345.0 (M+1); Preparation 14H: 4-Isopropyl-2-(2-trifluoromethoxy-phenyl)-2H-pyrazole-3-carboxylic acid methyl ester (82 g, 22%); Preparation 14I: 4-Cyclopropyl-2-(2-trifluoromethoxy-phenyl)-2H-pyrazole-3-carboxylic acid ethyl ester (0.65 g, 19%), ES/MS m/e 341.0 (M+1); Preparation 14J: 2-(2-Chloro-6-trifluoromethyl-phenyl)-4-cyclopropyl-2H-pyrazole-3-carboxylic acid ethyl ester (0.82 g, 38%), ES/MS m/e 359.0 (M+1).

Preparation 15

2-(2,6-Dichloro-phenyl)-4-isopropyl-2H-pyrazole-3-carboxylic Acid Methyl Ester

To a solution of 4-methyl-2-oxo-pentanoic acid methyl ester (3.8 g, 26 mmol) in N,N-dimethylformamide dimethyl acetal (7 mL, 52 mmol) is added p-toluenesulfonic acid monohydrate (30 mg) and the mixture is stirred at 80° C. overnight. The reaction mixture is concentrated under reduced pressure to give 3-isopropyl-4-dimethylamino-2-oxo-but-3-enoic acid ethyl ester as an orange oil. To a solution of 3-isopropyl-4-dimethylamino-2-oxo-but-3-enoic acid ethyl ester and 2,6-dichlorophenylhydrazine hydrochloride (2.8 g, 13 mmol) in EtOH (40 mL) is added concentrated HCl (0.5 mL). The mixture is stirred at ambient temperature for 2 h followed by refluxing overnight. The reaction mixture is concentrated and the residue is partitioned between EtOAc and 1N HCl. The organic phase is dried (Na$_2$SO$_4$) and concentrated to a residue. The residue is purified by column chromatography (0-15% EtOAc in hexanes) to give the title compound as an oil (2.2 g, 52%). $^1$H NMR (CDCl$_3$): δ 7.76 (s, 1H), 7.43 (d, 2H), 7.34 (dd, 1H), 3.75 (s, 3H), 3.48 (m, 1H), 1.32 (d, 6H).

Preparation 16

4-Isopropyl-2-(2-trifluoromethoxy-phenyl)-2H-pyrazol-3-carboxylic Acid Methyl Ester The title compound (82 g, 22%) is prepared essentially according to the preparation of 2-(2,6-Dichloro-phenyl)-4-isopropyl-2H-pyrazole-3-carboxylic acid methyl ester using the appropriate starting material.

Preparation 17

[2-(2,6-Dichloro-phenyl)-4-isopropyl-2H-pyrazol-3-yl]-methanol

To a 0° C. solution of 2-(2,6-dichloro-phenyl)-4-isopropyl-2H-pyrazole-3-carboxylic acid methyl ester (2.2 g, 6.8 mmol) in THF (30 mL) is added DIBAL-H (33.7 mL, 1M in toluene). The reaction mixture is stirred at ambient temperature overnight. The reaction is quenched by the addition of methanol and is concentrated under reduced pressure. The residue is partitioned between 5N NaOH and EtOAc. The layers are separated and the organic layer is filtered through a pad of diatomaceous earth. The filtrate is concentrated under reduced pressure to give the title compound as a light yellow solid, (1.6 g, 80%). $^1$H NMR (400 MHz, CDCl$_3$): δ 7.67 (s, 1H), 7.44 (d, 2H), 7.34 (dd, 1H), 4.45 (s, 2H), 3.00 (m, 1H), 1.32 (d, 6H).

The following list is prepared essentially according to the preparation of [2-(2,6-dichloro-phenyl)-4-isopropyl-2H-pyrazol-3-yl]-methanol using the appropriate starting materials.

Preparation 17A: [2-(2,6-Dichloro-phenyl)-4-isobutyl-5-methyl-2H-pyrazol-3-yl]-methanol (920 mg, 95%), $^1$H NMR (400 MHz, CDCl3) δ 7.46 (d, 2H), 7.36 (dd, 1H), 4.40 (s, 2H), 2.39 (d, 2H), 2.30 (s, 3H), 1.83 (m, 1H), 0.94 (d, 6H); Preparation 17B: [2-(2,6-Dichloro-phenyl)-4,5-dimethyl-2H-pyrazol-3-yl]-methanol, $^1$H NMR (CDCl3) δ 7.46 (d, 2H), 7.35 (dd, 1H), 4.40 (s, 2H), 2.29 (s, 3H), 2.11 (s, 3H); Preparation 17C: [2-(2,6-Dichloro-phenyl)-4-ethyl-5-methyl-2H-pyrazol-3-yl]-methanol, $^1$H NMR (CDCl3) δ 7.45 (d, 2H), 7.35 (dd, 1H), 4.40 (d, 2H), 2.55 (q, 2H), 2.32 (s, 3H), 1.20 (t, 3H); Preparation 17D: [2-(2,6-Dichloro-phenyl)-5-methyl-4-propyl-2H-pyrazol-3-yl]-methanol, $^1$H NMR (CDCl3) δ 7.46 (d, 2H), 7.35 (dd, 1H), 4.40 (s, 2H), 2.51 (t, 2H), 2.31 (s, 3H), 1.59 (m, 2H), 0.95 (t, 3H); Preparation 17E: [2-(2,6-Dichloro-phenyl)-5-methyl-2H-pyrazol-3-yl]-methanol $^1$H NMR (CDCl3) δ 7.46 (d, 2H), 7.36 (dd, 1H), 6.27 (s, 1H), 4.45 (s, 2H), 2.36 (s, 3H); Preparation 17F: [4-Isopropyl-2-(2-trifluoromethoxy-phenyl)-2H-pyrazol-3-yl]-methanol $^1$H NMR (CDCl$_3$): δ 7.41, 7.60 (m, 5H), 4.51 (s, 2H), 3.02 (m, 1H), 1.30 (d, 6H); Preparation 17G: [4-Isopropyl-2-(2-trifluoromethyl-phenyl)-2H-pyrazol-3-yl]-methanol, $^1$H NMR (CDCl$_3$): δ 7.82 (d, 1H, J=8.0 Hz), 7.64 (m, 2H), 7.57 (s, 1H), 7.50 (d, 1H, J=7.5 Hz), 4.45 (s, 2H), 2.99 (m, 1H), 1.30 (d, 6H); Preparation 17H: [2-(2,6-Difluoro-phenyl)-4-isopropyl-2H-pyrazol-3-yl]-methanol, $^1$H NMR (CDCl$_3$): δ 7.66 (s, 1H), 7.42, 7.46 (m, 1H), 7.08 (m, 2H), 4.52 (s, 2H), 3.01 (m, 1H), 1.31 (d, 6H); Preparation 17I: [2-(2,6-Dichloro-phenyl)-4-methyl-2H-pyrazol-3-yl]-methanol, $^1$H NMR (CDCl$_3$): δ 7.61 (s, 1H), 7.47 (d, 2H, J=8.3 Hz), 7.38 (dd, 1H, J=7.0, J=8.3 Hz), (m, 5H), 4.45 (s, 2H), 2.20 (s, 3H).

Preparation 18

[4-Cyclopropyl-2-(2,6-dichloro-phenyl)-2H-pyrazol-3-yl]-methanol

To a 0° C. mixture of LAH powder in THF (20 mL) is added a solution of 4-cyclopropyl-2-(2,6-dichloro-phenyl)-2H-Pyrazole-3-carboxylic acid ethyl ester (2.4 mmol, 0.8 g) in THF (10 mL). The reaction is stirred for 2 h at 0° C. The reaction is quenched with a sequence of water (0.26 mL), 5N NaOH (0.26 mL) and water (0.78 mL). The reaction mixture is stirred for 1 h at 0° C. The reaction is filtered and the filtrate is adsorbed onto silica gel and purified using a gradient of 30-50% EtOAc/Hexanes to yield the title compound (0.36 g, 53%). LC-ES/MS m/e 283.0 (M+1).

The following list of compounds is prepared essentially according to the preparation of [4-Cyclopropyl-2-(2,6-dichloro-phenyl)-2H-pyrazol-3-yl]-methanol using the appropriate starting materials.

Preparation 18A: [4-Cyclobutyl-2-(2,6-dichloro-phenyl)-2H-pyrazol-3-yl]-methanol (0.42 g, 86%), LC-ES/MS m/e 297.0 (M+1); Preparation 18B: [2-(2-Chloro-6-trifluoromethyl-phenyl)-4-isopropyl-2H-pyrazol-3-yl]-methanol (0.51 g, 87%), LC-ES/MS m/e 265.0 (M+1); Preparation 18C: [2-(3,5-Difluoro-2-trifluoromethyl-phenyl)-4-isopropyl-2H-pyrazol-3-yl]-methanol (0.38 g, 26%), LC-ES/MS m/e 267.0 (M+1); Preparation 18D: [2-(2-Fluoro-6-trifluoromethyl-phenyl)-4-isopropyl-2H-pyrazol-3-yl]methanol (0.19 g, 15%), LC-ES/MS m/e 249.0 (M+1); Preparation 18E: [2-(2,6-Dichloro-4-fluorophenyl)-4-isopropyl-2H-pyrazol-3-yl]-methanol (0.10 g, 39%), LC-ES/MS m/e 302.0 (M+1); Preparation 18F: 4-Isopropyl-2-(2-trifluoromethylsulfanyl-phenyl)-2H-pyrazol-3-yl]-methanol (0.081 g, 63%), LC-ES/MS m/e 317.0 (M+1); Preparation 18G: [4-Isopropyl-2-(2-trifluoromethoxy-phenyl)-2H-pyrazol-3-yl]-methanol (31 g, 49%). Preparation 18H: [4-Cyclopropyl-2-(2-trifluoromethoxy-phenyl)-2H-pyrazol-3-yl]-methanol (0.400, 70%), ES/MS m/e 299.0 (M+1); Preparation 18I: [2-(2-Chloro-6-trifluoromethyl-phenyl)-4-cyclopropyl-2H-pyrazol-3-yl]methanol (0.400, 54%), ES/MS m/e 317.0 (M+1).

Preparation 19

1-(2,6-Dichloro-phenyl)-4-isopropyl-5-[3-methyl-4-(4,4,5,5-tetramethyl-[1,3,2]dioxaborolan-2-yl)-phenoxymethyl]-1H-pyrazole A mixture of tricyclohexylphosphine (10 mg, 0.036 mmol) and palladium bis(dibenzylidene acetone) (8.5 mg, 0.015 mmol) in dioxane (3 mL) is stirred at room temperature for one half hour. To the reaction mixture, 5-(4-bromo-3-methyl-phenoxymethyl)-1-(2,6-dichloro-phenyl)-4-isopropyl-1H-pyrazole (227 mg, 0.500 mmol), pinacolborane (140 mg, 0.550 mmol) and potassium acetate (74 mg, 0.750 mmol) are added and the mixture is heated to 80° C. for 20 hours. The reaction mixture is cooled, diluted with water, and extracted with ether. The combined ether fractions are dried (MgSO$_4$) and evaporated. The residue is purified via flash chromatography (10% CH₂Cl₂/heptane to 0% CH₂Cl₂/heptane) to give the title compound (119 mg, 47%). ES/MS m/e 501.1(M+).

Preparation 20

6-[4-Isopropyl-2-(2-trifluoromethoxy-phenyl)-2H-pyrazol-3-ylmethoxy]-2-methyl-3-nitro-pyridine To an ambient temperature solution of [4-Isopropyl-2-(2-trifluoromethoxy-phenyl)-2H-pyrazol-3-yl]-methanol (2.0 g, 6.66 mmol) in degassed toluene (22 mL) is added 6-Chloro-2-methyl-3-nitro-pyridine (1.15 g, 6.66 mmol), cesium carbonate (3.25 g, 9.99 mmol), 2-(Di-t-butylphosphino)-1,1'-binapthyl (332 mg, 0.833 mmol, 12.5 mol %), and palladium (II) acetate (150 mg, 0.666 mmol, 10 mol %). The reaction mixture is heated to 70° C. overnight. The reaction mixture is filtered through a pad of Celite®, is concentrated under reduced pressure, and is chromatographed (0% to 20% EtOAc/Hex) to yield the title compound (2.73 g, 94%). $^1$H NMR (400 MHz, CDCl₃) δ 8.22 (d, 1H, J=8.8 Hz), 7.64 (s, 1H), 7.52 (dd, 1H, J=7.8, 1.7 Hz), 7.49-7.44 (m, 1H), 7.41-7.34 (m, 2H), 6.51 (d, 1H, J=9.2 Hz), 5.35 (s, 2H), 3.05 (sept, 1H, J=7.0 Hz), 2.72 (s, 3H), 1.29 (d, 6H, J=7.0 Hz).

Preparation 21

6-[4-Isopropyl-2-(2-trifluoromethoxy-phenyl)-2H-pyrazol-3-ylmethoxy]-2-methyl-pyridin-3-ylamine To an ambient temperature solution of 6-[4-Isopropyl-2-(2-trifluoromethoxy-phenyl)-2H-pyrazol-3-ylmethoxy]-2-methyl-3-nitro-pyridine (2.73 g, 6.25 mmol) in EtOH/THF (100/100 mL) is added platinum (II) oxide (142 mg, 0.625 mmol, 10 mol %). The reaction is placed under an atmosphere of hydrogen gas. After 3 h, the reaction is filtered through diatomaceous earth, concentrated, and chromatographed (0% to 30% EtOAc/Hex) to yield the title compound (2.15 g, 85%). $^1$H NMR (400 MHz, CDCl₃) δ 7.60 (s, 1H), 7.53 (dd, 1H, J=7.9, 1.8 Hz), 7.46-7.41 (m, 1H), 7.39-7.31 (m, 2H), 7.08 (d, 1H, J=8.8 Hz), 6.33 (d, 1H, J=8.4 Hz), 5.17 (s, 2H), 3.06 (sept, 1H, J=7.0 Hz), 2.32 (s, 3H), 1.27 (d, 6H, J=7.0 Hz).

Preparation 22

4-[2-(2,6-Dichloro-phenyl)-4-isopropyl-2H-pyrazol-3-ylmethoxy]-2-methyl-benzaldehyde To a −78° C. solution of 5-(4-Bromo-3-methyl-phenoxymethyl)-1-(2,6-dichloro-phenyl)-4-isopropyl-1H-pyrazole (906 mg, 2.0 mmol) in anhydrous THF is added 1.6 M n-butyllithium (1.35 mL). After 30 minutes, N,N-dimethylformamide is added (0.5 mL, 6.4 mmol). After 30 minutes, saturated aqueous ammonium chloride is added. The mixture is extracted with ethyl acetate (2×). The combined ethyl acetate layers are dried (MgSO₄) and concentrated under reduced pressure. The crude residue is purified via flash chromatography (ethyl acetate/heptane gradient) to afford the title compound (110 mg, 14%). LC-ES/MS m/e 403.0 (M+1).

Preparation 23

4-[2-(2,6-Dichloro-phenyl)-4-isopropyl-2H-pyrazol-3-ylmethoxy]-2-methyl-phenylamine To a 0° C. solution of [2-(2,6-dichloro-phenyl)-4-isopropyl-2H-pyrazol-3-yl]-methanol (3.0 g, 10.6 mmol), 4-amino-3-methyl-phenol (2.0 g, 15.8 mmol), and tri-n-butylphosphine (3.2 g, 15.8 mmol) in toluene (30 mL) is added a solution of 1,1'-(Azodicarbonyl)-dipiperidine (4.0 g, 15.8 mmol) in toluene (40 mL). The reaction mixture is allowed to warm to room temperature and is stirred for 3.0 h. The reaction mixture is partitioned between EtOAc (50 mL) and water (60 mL). The organic layer is washed with brine (60 mL), dried (Na₂SO₄), filtered, and concentrated under reduced pressure to a residue. The residue is purified by flash chromatography (EtOAc/Hexane) to afford the title compound as a solid (2.3 g, 56%). LC-ES/MS m/e 390.0 (M+1).

Preparation 24

5-(4-Bromo-3-methyl-phenoxymethyl)-1-(2,6-dichloro-phenyl)-4-isopropyl-1H-pyrazole The title compound is prepared essentially according to the preparation of 4-[2-(2,6-Dichloro-phenyl)-4-isopropyl-2H-pyrazol-3-ylmethoxy]-2-methyl-phenylamine using [2-(2,6-dichloro-phenyl)-4-isopropyl-2H-pyrazol-3-yl]-methanol and 4-bromo-3-methyl-phenol. ES/MS m/e 454.9 (M+1).

Preparation 25

{4-[2-(2,6-Dichloro-phenyl)-4-isopropyl-2H-pyrazol-3-ylmethoxy]-2-methyl-phenyl}-carbamic Acid Tert-butyl Ester A solution of di-tert-butyl dicarbonate (1.55 g, 7.1 mmol) in dichloromethane (3.0 mL) is added to a 0° C. solution of 4-[2-(2,6-dichloro-phenyl)-4-isopropyl-2H-pyrazol-3-ylmethoxy]-2-methyl-phenylamine (2.3 g, 5.9 mmol) and triethylamine (0.72 g, 7.1 mmol) in dichloromethane (20 mL). The reaction mixture is stirred at room temperature for 16.0 h. The reaction mixture is partitioned between dichloromethane (50 mL) and water (50 mL). The organic phase is washed with brine (50 mL), dried (Na₂SO₄), filtered, and concentrated under reduced pressure to a residue. The residue is purified by flash chromatography (EtOAc/Hexane) to afford the title compound as a solid (1.9 g, 66%). LC-ES/MS m/e 490.0 (M+1).

Preparation 26

{4-[2-(2,6-Dichloro-phenyl)-4-isopropyl-2H-pyrazol-3-ylmethoxy]-2-methyl-phenyl}-methyl-carbamic Acid Tert-butyl Ester To a 0° C. solution of {4-[2-(2,6-dichloro-phenyl)-4-isopropyl-2H-pyrazol-3-ylmethoxy]-2-methyl-phenyl}-carbamic acid tert-butyl ester (1.9 g, 3.9 mmol) in DMF (15 mL) is added sodium hydride (60% dispersion in mineral oil, 0.19 g, 4.7 mmol) portionwise. The mixture is stirred at 0° C. for 30 minutes. Iodomethane (0.83 g, 5.9 mmol) is added dropwise. The reaction mixture is then stirred at room temperature for 1.0 h. The reaction is quenched with the addition of saturated ammonium chloride (20 mL) at 0° C. The reaction mixture is partitioned between EtOAc (30 mL) and water (20 mL). The organic phase is washed with brine (30 mL), dried (Na₂SO₄), filtered, and concentrated under reduced pressure to yield the title compound (1.85 g, 95%) as a foamy solid. LC-ES/MS m/e 526.0 (M+23).

Preparation 27

{4-[2-(2,6-Dichloro-phenyl)-4-isopropyl-2H-pyrazol-3-ylmethoxy]-2-methyl-phenyl}-methyl-amine A solution of 4.0 M HCl in 1,4-dioxane (2.8 mL, 11.0 mmol) is added to a solution of {4-[2-(2,6-dichloro-phenyl)-4-isopropyl-2H-pyrazol-3-ylmethoxy]-2-methyl-phenyl}-methyl-carbamic acid tert-butyl ester (1.85 g, 3.7 mmol) in dichloromethane (25.0 mL) at 0° C. The reaction mixture is then stirred at room temperature for 2.0 h. The solvents are removed by evaporation under reduced pressure. The residue is partitioned between EtOAc (50 mL) and 5% aqueous sodium bicarbonate (30 mL). The organic layer is washed with brine (40 mL), dried ($Na_2SO_4$), filtered, and concentrated under reduced pressure to a residue. The residue is purified by flash chromatography (EtOAc/Hexane) to afford the title compound as a foamy solid (1.25 g, 84%). LC-ES/MS m/e 404.0 (M+1).

Preparation 28

(2-Bromo-ethyl)-{4-[2-(2,6-dichloro-phenyl)-4-isopropyl-2H-pyrazol-3-ylmethoxy]-2-methyl-phenyl}-methyl-amine To an ambient temperature solution of {4-[2-(2,6-Dichloro-phenyl)-4-isopropyl-2H-pyrazol-3-ylmethoxy]-2-methyl-phenyl}-methyl-amine (1.12 g, 2.77 mmol) in 1,2-dibromoethane (5 mL) is added triethylamine (1.54 mL, 11.08 mmol). The reaction is heated to 90° C. overnight. EtOAc is added to the reaction mixture. The resultant mixture is washed with brine, dried ($MgSO_4$), and chromatographed (0% to 20% EtOAc/Hex) to yield the title compound (520 mg, 37%). $^1$H NMR (400 MHz, $CDCl_3$) δ 7.70 (s, 1H), 7.43-7.40 (m, 2H), 7.31 (dd, 1H, J=9.0, 7.1 Hz), 6.93 (d, 1H, J=7.3 Hz), 6.61-6.54 (m, 2H), 4.77 (s, 2H), 3.34 (t, 2H, J=6.5 Hz), 3.26 (t, 2H, J=6.7 Hz), 2.99 (sept, 1H, J=7.0 Hz), 2.65 (s, 3H), 2.26 (s, 3H), 1.30 (d, 6H, J=7.0 Hz).

Preparation 29

1-{4-[2-(2,6-Dichloro-phenyl)-4-isopropyl-2H-pyrazol-3-ylmethoxy]-2-methyl-phenyl}-ethanone To a 0° C. suspension of 4'-Hydroxy-2'-methylacetophenone (716 mg, 4.77 mmol), [2-(2,6-Dichloro-phenyl)-4-isopropyl-2H-pyrazol-3-yl]-methanol (1.36 g, 4.77 mmol), tri-n-butylphosphine (1.78 mL, 7.15 mmol) in toluene (20 mL) is added ADDP (1.80 g, 7.15 mmol). The reaction is warmed to room temperature and is stirred overnight. The reaction is concentrated under reduced pressure and the residue is chromatographed (0% to 30% EtOAc/Hex) to yield the title compound (857 mg, 64%). $^1$H NMR (400 MHz, $CDCl_3$) δ 7.70 (s, 1H), 7.65 (d, 1H, J=8.8 Hz), 7.42-7.38 (m, 2H), 7.32-7.27 (m, 1H), 6.64-6.58 (m, 2H), 4.85 (s, 2H), 2.99 (sept, 1H, J=7.0 Hz), 2.50 (s, 3H), 2.49 (s, 3H), 1.30 (d, 6H, J=7.0 Hz).

Preparation 30

2-{4-[2-(2,6-Dichloro-phenyl)-4-isopropyl-2H-pyrazol-3-ylmethoxy]-2-methyl-phenyl}-propan-1-ol To a 0° C. solution of 2-{4-[2-(2,6-Dichloro-phenyl)-4-isopropyl-2H-pyrazol-3-ylmethoxy]-2-methyl-phenyl}-propionaldehyde (753 mg, 1.74 mmol) in THF (17 mL) and MeOH (3 mL) is added sodium borohydride (198 mg, 5.23 mmol) portionwise. The reaction mixture is warmed to room temperature. After 2 h, the reaction is concentrated under reduced pressure and the residue is partitioned between $Et_2O$ (100 mL) and 1N HCl (30 mL). The aqueous layer is extracted with $Et_2O$ (100 mL) and the combined organic layers are washed with brine, dried ($MgSO_4$), filtered, concentrated, and chromatographed (0% to 30% EtOAc/Hex) to yield the title compound (715 mg, 95%). $^1$H NMR (400 MHz, $CDCl_3$) δ 7.71 (s, 1H), 7.43-7.40 (m, 2H), 7.33-7.28 (m, 1H), 7.04 (d, 1H, J=8.4 Hz), 6.64-6.58 (m, 2H), 4.79 (s, 2H), 3.68-3.63 (m, 2H), 3.14-3.16 (m, 1H), 2.99 (sept, 1H, J=7.0 Hz), 2.28 (s, 3H), 1.30 (d, 3H, J=7.0 Hz), 1.21 (d, 6H, J=7.0 Hz).

The following list of compounds is prepared essentially according to the preparation of 2-{4-[2-(2,6-Dichloro-phenyl)-4-isopropyl-2H-pyrazol-3-ylmethoxy]-2-methyl-phenyl}-propan-1-ol using the appropriate starting materials.

Preparation 30A: 1-{4-[2-(2,6-Dichloro-phenyl)-4-isopropyl-2H-pyrazol-3-ylmethoxy]-2-methyl-phenyl}-ethanol, $^1$H NMR (400 MHz, $CDCl_3$) δ 7.70 (s, 1H), 7.41 (d, 2H, J=7.9 Hz), 7.36-7.27 (m, 2H), 6.64 (dd, 1H, J=8.8, 2.6 Hz), 6.55 (d, 1H, J=2.6 Hz), 5.04 (dq, 1H, J=6.6, 3.5 Hz), 4.80 (s, 2H), 3.00 (sept, 1H, J=7.0 Hz), 2.28 (s, 3H), 1.57 (d, 1H, J=3.5 Hz), 1.42 (d, 3H, J=6.6 Hz), 1.30 (d, 6H, J=7.0 Hz); Preparation 30B: {4-[2-(2,6-Dichloro-phenyl)-4-isopropyl-2H-pyrazol-3-ylmethoxy]-2-methyl-phenyl}-methanol (322 mg, 97%), $^1$H NMR (400 MHz, $CDCl_3$) δ 7.71 (s, 1H), 7.43-7.39 (m, 2H), 7.33-7.28 (m, 1H), 7.16 (d, 1H, J=7.9 Hz), 6.62-6.56 (m, 2H), 4.81 (s, 2H), 4.60 (s, 2H), 3.00 (sept, 1H, J=7.0 Hz), 2.31 (s, 3H), 1.31 (d, 6H, J=7.0 Hz); Preparation 30C: 2-{4-[2-(2,6-Dichloro-phenyl)-4-isopropyl-2H-pyrazol-3-ylmethoxy]-2-methyl-phenyl}-ethanol (260 mg, 87%), $^1$H NMR (400 MHz, $CDCl_3$) δ 7.71 (s, 1H), 7.43-7.40 (m, 2H), 7.31 (dd, 1H, J=8.8, 7.5 Hz), 7.00 (d, 1H, J=7.9 Hz), 6.60-6.54 (m, 2H), 4.79 (s, 2H), 3.77 (t, 2H, J=6.8 Hz), 3.00 (sept, 1H, J=6.6 Hz), 2.80 (t, 2H, J=6.8 Hz), 2.25 (s, 3H), 1.30 (d, 6H, J=6.6 Hz).

Preparation 31

1-(2,6-Dichloro-phenyl)-4-isopropyl-5-[4-(2-methoxy-1-methyl-vinyl)-3-methyl-phenoxymethyl]-1H-pyrazole To a room temperature suspension of potassium tert-butoxide (1.36 g, 12.12 mmol) in THF (30 mL) is added (methoxymethyl)triphenyl phosphonium chloride (4.14 g, 12.12 mmol). The reaction mixture is stirred at room temperature for 20 minutes. Solid 1-{4-[2-(2,6-Dichloro-phenyl)-4-isopropyl-2H-pyrazol-3-ylmethoxy]-2-methyl-phenyl}-ethanone (843 mg, 2.02 mmol) is added and the reaction is stirred at room temperature overnight. The reaction is quenched with saturated aqueous $NH_4Cl$ and is concentrated under reduced pressure. The residue is partitioned between $Et_2O$ and water. The aqueous layer is extracted with $Et_2O$ and the combined organic layers are washed with brine, dried ($MgSO_4$), filtered, concentrated under reduced pressure, and chromatographed (0% to 30% EtOAc/Hex) to yield the title compound (836 mg, 93%) as a mix of E/Z isomers. (Major Isomer) $^1$H NMR (400 MHz, $CDCl_3$) δ 7.70 (s, 1H), 7.41 (d, 2H, J=7.9 Hz), 7.33-7.28 (m, 1H), 6.93 (d, 1H, J=8.4 Hz), 6.64-6.52 (m, 2H), 5.83 (q, 1H, J=1.3 Hz), 4.78 (s, 2H), 3.63 (s, 3H), 3.00 (sept, 1H, J=7.0 Hz), 2.22 (s, 3H), 1.83 (d, 3H, J=1.3 Hz), 1.30 (d, 6H, J=7.0 Hz).

Preparation 32

4-[2-(2,6-Dichloro-phenyl)-4-isopropyl-2H-pyrazol-3-ylmethoxy]-2-methyl-benzaldehyde The title compound (1.51 g, 75%) is prepared essentially according to the preparation of 1-(2,6-Dichloro-phenyl)-4-isopropyl-5-[4-(2-methoxy-1-methyl-vinyl)-3-methyl-phenoxymethyl]-1H-pyrazole using 5-(4-bromo-3-methyl-phenoxymethyl)-1-(2,6-dichloro-phenyl)-4-isopropyl-1H-pyrazole. $^1$H NMR (400 MHz, CDCl$_3$) δ 10.09 (s, 1H), 7.73 (s, 1H), 7.68 (d, 1H, J=8.8 Hz), 7.44-7.40 (m, 2H), 7.31 (dd, 1H, J=8.6, 7.3 Hz), 6.71 (dd, 1H, J=8.6, 2.4 Hz), 6.61 (d, 1H, J=2.4 Hz), 4.89 (s, 2H), 3.01 (sept, 1H, J=6.6 Hz), 2.60 (s, 3H), 1.32 (d, 6H, J=6.6 Hz).

Preparation 33

To a 0° C. solution of 1-(2,6-Dichloro-phenyl)-4-isopropyl-5-[4-(2-methoxy-1-methyl-vinyl)-3-methyl-phenoxymethyl]-1H-pyrazole (825 mg, 1.85 mmol) in THF (20 mL) is added concentrated HCl (3 mL) dropwise. After 2 h, the reaction is diluted with water and the pH is adjusted to 7. The aqueous layer is extracted with Et$_2$O (2×200 mL). The combined organic layers are washed with brine, dried (MgSO$_4$), filtered, and concentrated to yield the title compound (764 mg, 96%). $^1$H NMR (400 MHz, CDCl$_3$) δ 9.58 (d, 1H, J=1.3 Hz), 7.70 (s, 1H), 7.43-7.40 (m, 2H), 7.33-7.28 (m, 1H), 6.88 (d, 1H, J=8.4 Hz), 6.66-6.61 (m, 2H), 4.80 (s, 2H), 3.73 (dq, 1H, J=7.0, 1.3 Hz), 2.99 (sept, 1H, J=7.0 Hz), 2.27 (s, 3H), 1.35 (d, 3H, J=7.0 Hz), 1.30 (d, 6H, J=7.0 Hz).

Preparation 34

{4-[2-(2,6-Dichloro-phenyl)-4-isopropyl-2H-pyrazol-3-ylmethoxy]-2-methyl-phenyl}-acetaldehyde The title compound (292 mg, quantitative yield) is prepared essentially according to the preparation of 2-{4-[2-(2,6-Dichloro-phenyl)-4-isopropyl-2H-pyrazol-3-ylmethoxy]-2-methyl-phenyl}-propionaldehyde using 1-(2,6-dichloro-phenyl)-4-isopropyl-5-[4-(2-methoxy-vinyl)-3-methyl-phenoxymethyl]-1H-pyrazole. $^1$H NMR (400 MHz, CDCl$_3$) δ 9.65 (t, 1H, J=2.2 Hz), 7.70 (s, 1H), 7.41 (d, 2H, J=8.4 Hz), 7.31 (dd, 1H, J=8.8, 7.4 Hz), 6.98 (d, 1H, J=7.9 Hz), 6.65-6.58 (m, 2H), 4.80 (s, 2H), 3.60 (d, 2H, J=2.2 Hz), 3.00 (sept, 1H, J=7.0 Hz), 2.18 (s, 3H), 1.31 (d, 6H, J=7.0 Hz).

Preparation 35

4-[2-(2,6-Dichloro-phenyl)-4-isopropyl-2H-pyrazol-3-ylmethoxy]-2-methyl-benzonitrile To an ambient temperature solution of [2-(2,6-Dichloro-phenyl)-4-isopropyl-2H-pyrazol-3-yl]-methanol (2.50 g, 8.76 mmol) in DMF (15 mL) is added 4-Fluoro-2-methyl-benzonitrile 1.18 g, 8.76 mmol), cesium carbonate (5.71 g, 17.53 mmol). The reaction mixture is heated to 80° C. overnight. The reaction mixture is concentrated and the residue is partitioned between Et$_2$O and water. The aqueous layer is extracted with Et$_2$O and the combined organic layers are washed with brine, dried (MgSO$_4$), filtered, concentrated, and chromatographed (0% to 20% EtOAc/Hex) to yield the title compound (2.13 g, 61%). $^1$H NMR (400 MHz, CDCl$_3$) δ 7.72 (s, 1H), 7.46-7.40 (m, 3H), 7.32 (dd, 1H, J=9.0, 7.3 Hz), 6.68-6.62 (m, 2H), 4.85 (s, 2H), 2.99 (sept, 1H, J=7.0 Hz), 2.46 (s, 3H), 1.31 (d, 6H, J=7.0 Hz).

Preparation 36

1-(2,6-Dichloro-phenyl)-4-isopropyl-5-[4-(2-methoxy-vinyl)-3-methyl-phenoxymethyl]-1H-pyrazole To an ambient temperature suspension of potassium tert-butoxide (668 mg, 5.96 mmol) in THF (20 mL) is added (methoxymethyl)triphenyl phosphonium chloride (2.04 g, 5.96 mmol) and is stirred at room temperature for 20 min. Solid 4-[2-(2,6-Dichloro-phenyl)-4-isopropyl-2H-pyrazol-3-ylmethoxy]-2-methyl-benzaldehyde (400 mg, 0.992 mmol) is added and the reaction is stirred at room temperature overnight. The reaction is quenched with sat. aq. NH$_4$Cl and concentrated. The residue is partitioned between Et$_2$O and water. The aqueous layer is extracted with Et$_2$O and the combined organic layers are washed with brine, dried (MgSO$_4$), filtered, concentrated and chromatographed (SiO$_2$ 120 g, 0% to 30% EtOAC/Hex) to yield the title compound (302 mg, 73%) as a mix of E/Z isomers. $^1$H NMR (400 MHz, CDCl$_3$) (major isomer) δ 7.70 (s, 1H), 7.43-7.38 (m, 2H), 7.33-7.26 (m, 1H), 7.08 (d, 1H, J=8.4 Hz), 6.72 (d, 1H, J=12.8 Hz), 6.60-6.52 (m, 2H), 5.82 (d, 1H, J=12.8 Hz), 4.78 (s, 2H), 3.66 (s, 3H), 3.00 (sept, 1H, J=7.0 Hz), 2.22 (s, 3H), 1.30 (d, 6H, J=7.0 Hz).

Preparation 37

1-(4-Methoxy-phenyl)-butane-1,3-dione

To a 0° C. suspension of sodium hydride (853 mg, 21.8 mmol, 60% oil dispersion) in THF (13 mL) is added ethyl acetate (2.03 mL, 20.8 mmol). The reaction is stirred at room temperature for 1 h. A solution of 4-methoxyacetophenone (1.56 g, 10.4 mmol), dibenzo-18-crown-6 (62 mg, 0.016 mmol) and ethanol (2 drops) in THF (13 mL) is added dropwise and the reaction mixture is heated to reflux. After 3 h, the reaction is cooled to room temperature, quenched with saturated aqueous NH$_4$Cl, and concentrated under reduced pressure. The residue is partitioned between EtOAc (200 mL) and water (50 mL). The aqueous layer is extracted with EtOAc (200 mL) and the combined organic layers are washed with brine, dried (MgSO$_4$), filtered, and concentrated. The residue is purified via chromatography (0 to 20% EtOAc/Hexanes) to yield the title compound (1.62 g, 81%). GC-ES/MS m/e 192

Preparation 38

3-Methyl-4-(4,4,5,5-tetramethyl-[1,3,2]dioxaborolan-2-yl)-phenol

A mixture of tricyclohexylphosphine (525 mg, 1.87 mmol), palladium bis(dibenzylidene acetone (460 mg, 0.801 mmol) and dioxane (200 mL) is stirred at room temperature for one half hour. To the reaction mixture are added 4-bromo-3-methyl-phenol (5.00 g, 26.7 mmol), pinacolborane (7.45 g, 40.1 mmol) and potassium acetate (3.93 g, 40.1 mmol). The mixture is heated to 80° C. for 20 hours. The reaction mixture is cooled to room temperature, diluted with water, and extracted with ether. The combined ether fractions are washed with brine, dried (MgSO$_4$), and evaporated. The residue is purified using flash chromatography (0 to 2% MeOH/CH$_2$Cl$_2$), to yield the title compound (1.6 g. 47%). A second purification of impure fractions provided an additional 2.76 g of the title compound for a total of 4.36 g (70%). ES/MS m/e 233.3 (M−1).

Preparation 39

6-Bromo-1H-indole-3-carboxylic Acid Methyl Ester

To a solution of 6-bromoindole-3-carboxylic acid (960 mg, 4.00 mmol) in methanol (9.5 mL) is added (trimethylsilyl) diazomethane (2.0 M solution in hexanes, approximately 9 mL) over two minutes at room temperature. The yellow mixture is concentrated under reduced pressure. The residue is redissolved in methanol and concentrated under reduced pressure several times to give the title compound as a solid (100%). ES/MS m/e 256.0 (M+2).

The following list of compounds is prepared essentially according to the preparation of 6-bromo-1H-indole-3-carboxylic acid methyl ester using the appropriate starting materials.

Preparation 39A: (5-Bromo-1H-indol-3-yl)-acetic acid methyl ester (710 mg, 99%), ES/MS m/e 266.2 (M−2); Preparation 39B: 5-Bromo-1H-indole-3-carboxylic acid methyl ester, ES/MS m/e 255.9 (M+2).

Preparation 40

6-(4-Hydroxy-2-methyl-phenyl)-1H-indole-3-carboxylic Acid Methyl Ester

A mixture of 3-methyl-4-(4,4,5,5-tetramethyl-[1,3,2]dioxaborolan-2-yl)-phenol (213 mg, 0.910 mmol), 6-bromo-1H-indole-3-carboxylic acid methyl ester (193 mg, 0.759 mmol), tetrakis(triphenylphosphine)palladium(0) (57 mg, 0.046 mmol), DMF (2.7 mL), ethanol (1.34 mL) and 2M aqueous potassium carbonate (1.34 mL) is heated to 100° C. for 60 hours. The reaction is cooled to room temperature, diluted with water and acidified with 1 N HCl. The resulting solution is extracted with ethyl acetate. The combined organic layers are dried over anhydrous magnesium sulfate and concentrated. The residue is purified with flash chromatography eluting with 25 to 40% ethyl acetate/heptane to give the title compound (134 mg, 63%). ES/MS m/e 280.3 (M−1).

The following list of compounds is prepared essentially according to the preparation of 6-(4-Hydroxy-2-methyl-phenyl)-1H-indole-3-carboxylic acid methyl ester using the appropriate starting materials.

Preparation 40A: 6-(4-Hydroxy-2-methyl-phenyl)-1H-indole-2-carboxylic acid ethyl ester, ES/MS m/e 296.1 (M+1); Preparation 40B: 5-(4-Hydroxy-2-methyl-phenyl)-1H-indole-3-carboxylic acid methyl ester, ES/MS m/e 252.1 (M−2); Preparation 40C: [5-(4-Hydroxy-2-methyl-phenyl)-1H-indol-3-yl]-acetic acid methyl ester (180 mg, 60%), ES/MS m/e 296.1 (M+1); Preparation 40D: 6-(4-Hydroxy-2-methyl-phenyl)-benzo[b]thiophene-2-carboxylic acid methyl ester, ES/MS m/e 297.3 (M−1); Preparation 40E: (4'-Hydroxy-2'-methyl-biphenyl-4-yl)-acetic acid methyl ester (247 mg, 56%), ES/MS m/e 257.0 (M+1); Preparation 40F: 6-(4-Hydroxy-2-methyl-phenyl)-benzo[b]thiophene-3-carboxylic acid methyl ester; compound with 6-(4-hydroxy-2-methyl-phenyl)-benzo[b]thiophene-2-carboxylic acid methyl ester, ES/MS m/e 297.0 (M−1); Preparation 40G: 6-Bromo-benzo[b]thiophene-2-carboxylic acid methyl ester, $^1$H NMR (400 MHz, CDCl$_3$) δ 7.99 (m, 2H), 7.70 (d, 1H), 7.50 (d, 1H), 3.92 (s, 3H).

Preparation 41

6-Bromo-1-methyl-1H-indole-3-carboxylic Acid Methyl Ester

A mixture of 5-bromo-1H-indole-3-carboxylic acid methyl ester (100 mg, 0.394 mmol), potassium carbonate (163 mg, 1.18 mmol) and DMF is stirred at room temperature and iodomethane (30 μL, 0.47 mmol) is added. After 1.5 hours, additional iodomethane (10 μL) is added and the reaction is stirred for 30 minutes, diluted with dichloromethane, and filtered. The filtrate is concentrated under high vacuum, diluted with ethyl acetate, and concentrated to give the title compound (105 mg, 99%). ES/MS m/e 270.0 (M+2).

Preparation 42

2- and 3-acetyl-6-bromobenzothiophene

To a solution of 6-bromobenzothiophene (20 g, 93.8 mmol) and acetyl chloride (8.84 g, 112.6 mmol) in 120 mL of 1,2-dichloroethane is added dropwise at room temperature, tin tetrachloride (1M in dichloromethane, 112.6 mmol, 112.6 mL) under nitrogen. After the addition is complete, the reaction mixture is stirred at room temperature overnight. The mixture is poured into an ice/water bath and is extracted with dichloromethane. The organic phase is washed with sat. NaHCO$_3$, water, and brine, dried over MgSO$_4$, and evaporated. The crude residue is purified by flash chromatography, using hexane/EtOAc 6:1 as eluent mixture. The title compound (12 g, 50%) is obtained of a mixture 7:3 of the two isomers: 3-acetyl-6-bromobenzothiophene and 2-acetyl-6-bromobenzothiophene. ES/MS m/e 256 (M+2).

Preparation 43

6-Bromobenzothiophene-3-carboxylic acid and 6-Bromobenzothiophene-2-carboxylic Acid To a 0° C. solution of sodium hydroxide (13.64 g, 341 mmol) in water (94 mL, 5.22 mmol) is added slowly bromine (21.92 g, 137.18 mmol). The reaction mixture is stirred at 0° C. for 15 min. To the mixture is added dropwise a solution of 2- and 3-acetyl-6-bromobenzothiophene (10.00 g, 39.19 mmol) in dioxane (75 mL). The reaction mixture is stirred at room temperature for 2 hours followed by the addition of 50 mL of a NaHSO$_3$ (40%) solution and then 10 mL of HCl. An orange solid is visualized. The solid is filtered off and is washed with water and hexanes to give the title compound (7 g, 70%) as a mixture of 6-bromobenzothiophene-3-carboxylic acid and 6-bromobenzothiophene-2-carboxylic acid in a ratio 7:3. ES/MS m/e 258 (M+2).

Preparation 44

6-Bromobenzothiophene-3-carboxylic Acid Methyl Ester and 6-Bromobenzothiophene-2-carboxylic Acid Methyl Ester in a Ratio A solution of the mixture of 6-Bromobenzothiophene-3-carboxylic acid and 6-Bromobenzothiophene-2-carboxylic acid (6.5 g, 25.28 mmol) and sulfuric acid (4.65 g, 47.43 mmol) in MeOH (100 mL) is heated to 65° C. overnight. A light brown solid is visualized. The solution is cooled to room temperature. The solid is filtered off and is washed with MeOH to afford the title compound (5.6 g, 83%) as a mixture of 6-bromobenzothiophene-3-carboxylic acid methyl ester and 6-bromobenzothiophene-2-carboxylic acid methyl ester in a ratio 7:3. ES/MS m/e 272 (M+2).

Preparation 45

3-(4'-Hydroxy-2'-methyl-biphenyl-4-yl)-acrylic Acid Methyl Ester

A mixture of 4-bromo-3-methyl-phenol (460 mg, 2.01 mmol), [4-(E-3-methoxy-3-oxo-1-propen-1-yl)phenyl]boronic acid (486 mg, 2.21 mmol), tetrakis(triphenylphosphine)palladium(0) (232 mg, 0.201 mmol) cesium carbonate (1.31 g, 4.02 mmol) and DMF (4.8 mL) is heated to 80° C. for 4.5 hours. The reaction is cooled to room temperature and diluted with water and acidified with 1 N HCl. The resulting solution is extracted with ether. The combined organic layers are dried over anhydrous magnesium sulfate and are purified via flash chromatography eluting with 15% ethyl acetate/heptane to give the title compound (108 mg, 20%). ES/MS m/e 267.3 (M−1).

The following list of compounds is prepared essentially according to the preparation of 3-(4'-hydroxy-2'-methyl-biphenyl-4-yl)-acrylic acid methyl ester using the appropriate starting material.

Preparation 45A: 6-(4-Hydroxy-2-methyl-phenyl)-1-methyl-1H-indole-3-carboxylic acid methyl ester, LC-ES/MS m/e 296.0 (M+1); Preparation 45B: 3-(4'-Hydroxy-2'-methyl-biphenyl-4-yl)-propionic acid ethyl ester (457 mg, 78%), ES/MS m/e 283.3 (M−1); Preparation 45C: 3-(4'-Hydroxy-2'-methyl-biphenyl-3-yl)-propionic acid methyl ester ES/MS m/e 269.2 (M+1); Preparation 45D: (4'-Hydroxy-2'-methyl-biphenyl-3-yl)-acetic acid methyl ester, ES/MS m/e 255.2 (M−1); Preparation 45E: 3-(4'-Hydroxy-2'-methyl-biphenyl-3-yl)-acrylic acid methyl ester, ES/MS m/e 269.2 (M+1); ); Preparation 45F: 6-(4-Hydroxy-2-methyl-phenyl)-benzo[b]thiophene-3-carboxylic acid methyl ester; compound with 6-(4-hydroxy-2-methyl-phenyl)-benzo[b]thiophene-2-carboxylic acid methyl ester, starting from a 7:3 mixture of 6-bromo-benzo[b]thiophene-3-carboxylic acid methyl ester and 6-bromo-benzo[b]thiophene-2-carboxylic acid methyl ester, MS m/z: 297.0 (M−1).

Preparation 46

Step A

4'-Benzyloxy-biphenyl-3-carboxylic Acid Ethyl Ester

To a solution of ethyl-3-iodobenzoate (2.5 g, 1 equiv) in ethylene glycol dimethyl ether (20 mL) are added 2 M sodium carbonate solution (40 mL), 4-benzyloxybenzene boronic acid (2.5 g, 1.2 equiv) and tetrakistriphenylphosphine palladium(0) (1.05 g, 0.1 equiv). The reaction mixture is heated to reflux for 2 h. The reaction mixture is allowed to cool to room temperature and is diluted with 300 mL 50% sodium bicarbonate solution. The product is extracted three times with methylene chloride. The combined organic layers are dried over magnesium sulfate, filtered, and concentrated under reduced pressure. The residue is purified via flash chromatography eluting with ethyl acetate/hexanes (2:98 to 8:92) to give the desired product (2.3 g, 76%) as a white solid.

Step B

4'-Hydroxy-biphenyl-3-carboxylic Acid Ethyl Ester

To a solution of 4'-Benzyloxy-biphenyl-3-carboxylic acid ethyl ester (2.3 g) in ethanol/ethyl acetate (3:1) (200 mL) is added 5% palladium on carbon (300 mg). The reaction mixture is placed under an atmosphere of hydrogen (55 psi) and is shaken on a Parr apparatus for 2 h. Concentrated hydrochloric acid (0.3 mL) is added to the reaction mixture. The reaction mixture is allowed to proceed for an additional 10 h. Trifluoroacetic acid (1 mL) and 20% palladium hydroxide on carbon (300 mg) are added to the reaction mixture and the reaction is allowed to stir under an atmosphere of hydrogen (60 psi). After an additional 80 h, the reaction mixture is degassed with nitrogen and is filtered though a plug of silica gel, eluting with 500 mL ethyl acetate and 500 mL ethanol. The filtrate is concentrated under reduced pressure and the residue is diluted with 400 mL saturated sodium bicarbonate solution. The product is extracted three times with methylene chloride. The combined organic layers are dried over magnesium sulfate, filtered, and concentrated under reduced pressure to afford the title compound (1.6 g, 95%) as a white solid.

Preparation 47

Step A

2'-Amino-4'-methoxy-biphenyl-4-carboxylic Acid Methyl Ester

To 4'-Methoxy-2'-nitro-biphenyl-4-carboxylic acid methyl ester (4.00 g) suspended in ethanol (150 mL) and ethyl acetate (150 mL) is added 5% palladium on carbon (0.300 g). The reaction mixture is placed under an atmosphere of hydrogen (50 psi) and is shaken on a Parr apparatus. After 18 h, the reaction mixture is degassed with nitrogen and is filtered through a plug of silica gel, eluting with 700 mL ethyl acetate and 600 mL methylene chloride. The filtrate is evaporated to afford the title compound (3.52 g, >99%) as a white solid.

Step B

2'-Bromo-4'-methoxy-biphenyl-4-carboxylic Acid Methyl Ester

To a solution of sodium nitrite (1.40 g) in dimethyl sulfoxide (50 mL) is added 2'-amino-4'-methoxy-biphenyl-4-carboxylic acid methyl ester (2.61 g). After 5 minutes, the reaction mixture is treated with a solution of 4.7 mL hydrobromic acid (48%) in 50 mL dimethyl sulfoxide. The reaction is allowed to stir at room temperature for 2 h. The reaction mixture is diluted with a solution of 20.0 g potassium carbonate dissolved in 400 mL water. The product is extracted five times with methylene chloride. The combined organic layers are dried over magnesium sulfate, filtered, and concentrated under reduced pressure. The residue is purified via flash chromatography eluting with hexanes/ethyl acetate (99:1 to 86:14) to afford the title compound (1.00 g, 31%) as a white solid.

Step C

2'-Bromo-4'-hydroxy-biphenyl-4-carboxylic Acid Methyl Ester

To a 0° C. solution of 2'-bromo-4'-methoxy-biphenyl-4-carboxylic acid methyl ester (0.200 g) in methylene chloride (5 mL) is added boron tribromide (0.176 mL). The reaction mixture is maintained at 0° C. for 2 h. The reaction mixture is slowly quenched with 50 mL methanol, diluted with 150 mL 2N hydrochloric acid, and extracted three times with methylene chloride. The combined organic layers are dried over magnesium sulfate, filtered, and concentrated under reduced pressure to afford the title compound (0.180 g, 94%).

Preparation 48

4'-Hydroxy-2'-methyl-biphenyl-4-carboxylic Acid Methyl Ester

To a solution of 4-Bromo-3-methyl phenol (0.300 g, 1 equiv) in DMF (5 mL) are added 4-methylester phenyl boronic acid (0.58 g, 2 equiv), dppf (0.27 g, 0.3 equiv), palladium acetate (0.036 g, 0.1 equiv), and cesium carbonate (1.04 g, 2 equiv). The reaction mixture is heated to 75° C. for 1 h. The reaction is cooled to room temperature and is diluted with water. The resulting solution is extracted with ethyl acetate. The combined organic layers are combined, washed with brine, dried over sodium sulfate, filtered, and concentrated under reduced pressure. The crude residue is purified via flash chromatography eluting with 3% ethyl acetate in toluene to give the desired product (0.224 g, 58%). ES/MS m/e 241.3 (M−1)

Preparation 49

2-(4-Methoxy-phenyl)-4-methyl-thiazole-5-carboxylic Acid Ethyl Ester

A mixture of 4-methoxy-thiobenzamide (5 g, 30 mmol) and 2-chloro-3-oxo-butyric acid ethyl ester (4.6 mL, 33 mmol) in ethanol is stirred under reflux overnight. The reaction mixture is concentrated and the residue is triturated with ether to give the title compound as a yellow solid (5.8 g, 70%). LC-ES/MS m/e 278 (M+1)

Preparation 50

2-(4-Hydroxy-phenyl)-4-methyl-thiazole-5-carboxylic Acid Ethyl Ester

To a solution of 2-(4-methoxy-phenyl)-4-methyl-thiazole-5-carboxylic acid ethyl ester (550 mg, 2 mmol) in dichloromethane (20 mL) at −80° C. is added $BBr_3$ (5 mL, 1M solution in dichloromethane). The reaction is stirred at ambient temperature overnight. The reaction is quenched by addition of methanol and is concentrated under reduced pressure. The residue is partitioned between EtOAc and 1N HCl. The organic layer is concentrated and the residue is purified by chromatography (0 to 30% EtOAc in hexanes) to give the title compound as a tan solid (500 mg, 95%). LC-ES/MS m/e 264 (M+1), $^1$H NMR (400 MHz, DMSO-d6) δ 10.22 (s, 1H), 7.82 (d, 2H), 6.86 (d, 2H), 4.27 (q, 2H), 2.64 (s, 3H), 1.29 (t, 3H).

Preparation 51

2-(4-Hydroxy-phenyl)-benzo[b]thiophene-6-carboxylic Acid Methyl Ester

The title compound (57 mg, 12%) is prepared essentially according to the preparation of 2-(4-Hydroxy-phenyl)-4-methyl-thiazole-5-carboxylic acid ethyl ester using 2-(4-methoxy-phenyl)-benzo[b]thiophene-6-carboxylic acid methyl ester. LC-ES/MS m/e 283 (M−1).

Preparation 52

Trifluoro-methanesulfonic acid 2-(4-methoxy-phenyl)-benzo[b]thiophen-6-yl Ester To a solution of 2-(4-methoxy-phenyl)-benzo[b]thiophen-6-ol (512 mg, 2 mmol) in dichloromethane (20 mL) at 0° C. is added triethylamine (0.58 mL, 5 mmol) and trifluoromethanesulfonic anhydride (0.67 mL, 4 mmol). The reaction is stirred at ambient temperature overnight. The reaction mixture is concentrated and the residue is redissolved in EtOAc, washed with 1N NaOH followed by 1N HCl. The organic layer is concentrated to give the title compound as a tan solid (800 mg, quant.).

Preparation 53

2-(4-Methoxy-phenyl)-benzo[b]thiophene-6-carboxylic Acid Methyl Ester

A mixture of trifluoro-methanesulfonic acid 2-(4-methoxy-phenyl)-benzo[b]thiophen-6-yl ester (750 mg), palladium acetate (43 mg), 1,4-bis(diphenylphosphino)butane (97 mg), triethylamine (1.4 mL) in MeOH (8 mL) and DMSO (12 mL) is stirred under an atmosphere of carbon monoxide (100 psi) at 80° C. for 4 h. The reaction mixture is filtered through a Celite® pad and the filtrate is concentrated. The residue is purified by column chromatography (0 to 20% EtOAc in hexanes) to give the title compound as a tan solid, (500 mg, 87%). LC-ES/MS m/e 321 (M+Na).

Preparation 54

5-(4-Hydroxy-2-methyl-phenyl)-4-methyl-thiophene-2-carboxylic Acid Methyl Ester

Step A

To a mixture of 4-methoxy-2-methylphenylboronic acid (912 mg, 6 mmol), 5-bromo-4-methyl-thiophene-2-carboxylic acid methyl ester (1.1 g, 5 mmol) and $K_2CO_3$ (1.38 g, 10 mmol) in toluene (30 mL) and water (5 mL) is bubbled $N_2$ for 15 minutes followed by addition of tetrakis(triphenylphosphine) palladium (289 mg, 0.25 mmol). The mixture is stirred at 80° C. under $N_2$ overnight. The reaction mixture is filtered through a Celite® pad eluting with EtOAc. The combined filtrate is concentrated under reduced pressure and the residue is purified by column chromatography (0-15% EtOAc in hexanes) to give 5-(4-methoxy-2-methyl-phenyl)-4-methyl-thiophene-2-carboxylic acid methyl ester (540 mg, 39%). $^1$H NMR (CDCl$_3$): δ 7.63 (s, 1H), 7.15 (d, 1H, J=8.4 Hz), 6.82 (d, 1H, J=2.8 Hz), 6.78 (dd, 1H, J=2.8, J=8.4 Hz), 4.79 (bs, 1H), 3.88 (s, 3H), 3.83 (s, 3H), 2.17 (s, 3H), 2.02 (s, 3H).

Step B

To a solution of 5-(4-methoxy-2-methyl-phenyl)-4-methyl-thiophene-2-carboxylic acid methyl ester (540 mg, 2 mmol) in dichloromethane (30 mL) at 0° C. is added BBr₃ in dichloromethane (1N, 5.0 mL) and the mixture is stirred at ambient temperature overnight. The reaction is quenched by addition of methanol and is evaporated. The residue is purified by column chromatography (0-20% EtOAc in hexanes) to give 5-(4-hydroxy-2-methyl-phenyl)-4-methyl-thiophene-2-carboxylic acid methyl ester (420 mg, 82%). $^1$H NMR (CDCl₃): δ 7.62 (s, 1H), 7.10 (d, 1H, J=7.9 Hz), 6.76 (s, 1H), 6.70 (d, 1H, J=7.9 Hz), 4.79 (bs, 1H), 3.88 (s, 3H), 2.15 (s, 3H), 2.02 (s, 3H).

The following list of compounds is prepared essentially according to the preparation of 5-(4-hydroxy-2-methyl-phenyl)-4-methyl-thiophene-2-carboxylic acid methyl ester using the appropriate starting material.

Preparation 54A: 5-(4-Hydroxy-phenyl)-thiophene-2-carboxylic acid methyl ester, $^1$H NMR (DMSO-d₆): δ 9.87 (s, 1H), 7.74 (d, 1H, J=4.0 Hz), 7.57 (d, 2H, J=8.8 Hz), 7.40 (d, 1H, J=4.0 Hz), 6.83 (d, 2H, J=8.8 Hz), 3.81 (s, 3H); Preparation 54B: 5-(4-Hydroxy-2-methyl-phenyl)-thiophene-2-carboxylic acid methyl ester, $^1$H NMR (DMSO-d₆): δ 9.71 (s, 1H), 7.76 (d, 1H, J=3.5 Hz), 7.26 (d, 1H, J=8.4 Hz), 7.17 (d, 1H, J=4.0 Hz), 6.72 (d, 1H, J=2.6 Hz), 6.67 (dd, 1H, J=2.6, J=8.4 Hz), 3.81 (s, 3H), 2.32 (s, 3H); Preparation 54C: 5-(2-Chloro-4-hydroxy-phenyl)-thiophene-2-carboxylic acid methyl ester, $^1$H NMR (DMSO-d₆): δ 10.33 (s, 1H), 7.78 (d, 1H, J=3.8 Hz), 7.53 (d, 1H, J=8.6 Hz), 7.37 (d, 1H, J=3.8 Hz), 6.96 (s, 1H), 6.84 (d, 1H, J=8.6 Hz), 3.82 (s, 3H); Preparation 54D: 5-(2-Chloro-4-hydroxy-phenyl)-4-methyl-thiophene-2-carboxylic acid methyl ester, $^1$H NMR (DMSO-d₆): δ 10.26 (bs, 1H), 7.68 (s, 1H), 7.25 (d, 1H, J=8.4 Hz), 6.96 (d, 1H, J=2.6 Hz), 6.83 (dd, 1H, J=2.6, 8.4 Hz), 3.82 (s, 3H), 2.03 (s, 3H); Preparation 54E: 2-(4-Hydroxy-2-methyl-phenyl)-4-methyl-thiazole-5-carboxylic acid methyl ester, $^1$H NMR (DMSO-d₆): δ 10.0 (s, 1H), 7.74 (d, 1H, J=8.4 Hz), 6.74 (s, 1H), 6.73 (d, 1H, J=8.4 Hz), 3.81 (s, 3H), 2.67 (s, 1H), 2.50 (s, 3H); Preparation 54F: 2-(4-Hydroxy-2-methyl-phenyl)-thiazole-5-carboxylic acid ethyl ester, $^1$H NMR (DMSO-d₆): δ 8.44 (s, 1H), 7.74 (d, 1H, J=8.4 Hz), 6.76 (s, 1H), 6.75 (d, 1H, J=8.4 Hz), 4.33 (q, 2H), 2.51 (s, 3H), 1.30 (t, 3H); Preparation 54G: 6-(4-Hydroxy-2-methyl-phenyl)-nicotinic acid methyl ester, $^1$H NMR (DMSO-d₆): δ 9.65 (s, 1H), 9.10 (s, 1H), 8.27 (dd, 1H, J=2.2, J=8.4 Hz), 7.62 (dd, 1H, J=0.9, J=8.4 Hz), 7.32 (d, 1H, J=8.8 Hz), 6.71 (s, 1H), 6.69 (t, 1H), 3.89 (s, 3H), 2.31 (s, 3H); Preparation 54H: 4'-Hydroxy-2,2'-dimethyl-biphenyl-4-carboxylic acid methyl ester, (700 mg, 82%), $^1$H NMR (CDCl₃): δ 7.94 (d, 1H, J=1.7 Hz), 7.87 (dd, 1H, J=1.7, J=7.9 Hz), 7.16 (d, 1H, J=7.9 Hz), 6.94 (d, 1H, J=7.9 Hz), 6.77 (d, 1H, J=2.6 Hz), 6.71 (dd, 1H, J=2.6, J=7.9 Hz), 5.0 (bs, 1H), 3.93 (s, 3H), 2.10 (s, 3H), 1.99 (s, 3H).

Preparation 55

2-(4-Hydroxy-phenyl)-4-methyl-thiazole-5-carboxylic Acid Ethyl Ester

Step A

A mixture of 4-methoxy-thiobenzamide (5 g, 30 mmol) and 2-chloro-3-oxo-butyric acid ethyl ester (4.6 mL, 33 mmol) in ethanol is stirred under reflux overnight. The reaction mixture is concentrated and the residue triturated with ether to give 2-(4-methoxy-phenyl)-4-methyl-thiazole-5-carboxylic acid ethyl ester as a yellow solid, 5.8 g (70%). LC-MS: 278 (M+1)

Step B

To a solution of 2-(4-methoxy-phenyl)-4-methyl-thiazole-5-carboxylic acid ethyl ester (550 mg, 2 mmol) in dichloromethane (20 mL) at −80° C. is added BBr₃ (5 mL, 1M solution in dichloromethane). The reaction mixture is stirred at ambient temperature overnight. The reaction is quenched by addition of methanol and is concentrated. The residue is partitioned between EtOAc and 1N HCl. The organic layer is concentrated and purified by chromatography (0 to 30% EtOAc in hexanes) to give the title compound as a tan solid, (500 mg, 95%). LC-MS: 264 (M+1); $^1$H NMR (DMSO-d₆) δ 10.22 (s, 1H), 7.82 (d, 2H), 6.86 (d, 2H), 4.27 (q, 2H), 2.64 (s, 3H), 1.29 (t, 3H).

Preparation 56

4-{[(4-Hydroxy-2-methyl-phenyl)-methyl-amino]-methyl}-benzoic Acid Methyl Ester

To an ambient temperature solution of 4-amino-3-methyl-phenol (1.0 g, 8.12 mmol) in MeOH (77 mL) is added 4-formyl-benzoic acid methyl ester (1.47 g, 8.93 mmol) and decaborane (329 mg, 2.68 mmol). The reaction is stirred at room temperature. After 2 h, formaldehyde (1.23 mL, 16.93 mmol, 37% in water) and decaborane (329 mg, 2.68 mmol) are added and the reaction is stirred overnight. The reaction is concentrated under reduced pressure and the residue is purified via chromatography to yield the title compound (2.07 g, 90%). LC-ES/MS m/e 286.2 (M+1)

Preparation 57

3-{[(4-Hydroxy-2-methyl-phenyl)-methyl-amino]-methyl}-benzoic Acid Methyl Ester

The title compound is prepared essentially as described in the preparation of 4-{[(4-Hydroxy-2-methyl-phenyl)-methyl-amino]-methyl}-benzoic acid methyl ester using 3-formyl-benzoic acid methyl ester (74% yield). LC-ES/MS m/e 286.2 (M+1)

Preparation 58

3-[2-(2-Chloro-4-hydroxy-phenyl)-vinyl]-benzoic Acid Methyl Ester

To a solution of 3-vinylbenzoic acid methyl ester (0.300 g) in dimethylformamide (3 mL) are added 4-bromo-3-methyl phenol (0.35 g), tri(orthotoluoyl)phosphine (0.06 g), Pd(dba)₂ (0.032 g), and triethylamine (0.26 mL). The reaction is heated to 100° C. overnight. Upon cooling to room temperature, the solvent is evaporated under reduced pressure. The residue is dissolved in ethyl acetate. The organic layer is washed with water and brine, dried over sodium sulfate, filtered, and concentrated under reduced pressure. The resulting residue is purified via filter chromatography eluting with 300 mL toluene followed by 250 mL 10% ethyl acetate in toluene to give the title compound (0.210 g). $^1$H NMR (400 MHz, CDCl₃) δ 8.20 (s, 1H), 7.95-7.93 (d, 1H), 7.71-7.69 (d, 1H), 7.53-7.51 (d, 1H), 7.48-7.44 (t, 1H), 7.38-7.34 (d, 1H), 6.96-6.92 (d, 1H), 6.77-6.72 (m, 2H), 5.26 (broad s, 1H), 3.99 (s, 3H), 2.43 (s, 3H).

Preparation 59

2-Allyl-4-methyl-benzoic Acid Methyl Ester

To a solution of 2-bromo-4-methyl-benzoic acid methyl ester (1.330 g, 5.81 mmol) in 5 mL DMF and 50 mL acetonitrile are added allyl tri-n-butyl tin (2.12 g, 6.39 mmol), PdCl$_2$(PPh$_3$)$_2$ (0.203 g, 0.29 mmol), and lithium chloride (0.493 g, 11.6 mmol). The resulting mixture is heated to 120° C. for 8 hours. The reaction is cooled to room temperature and concentrated under reduced pressure. The residue is dissolved in dichloromethane and purified via chromatography eluting with 10% ethyl acetate in hexanes to give 0.980 g (89%) of the desired product. $^1$H NMR (400 MHz, CDCl$_3$) δ 7.79-7.76 (d, 1H), 7.05 (s, 1H), 7.05-7.03 (d, 1H), 6.03-5.92 (m, 1H), 5.01 (dd, 1H), 4.99-4.98 (dd, 1H), 3.84 (s, 3H), 3.72 (dd, 1H), 3.70 (dd, 1H), 2.33 (s, 3H).

Preparation 60

4-Methyl-2-(2-oxo-ethyl)-benzoic Acid Methyl Ester

To a solution of 2-allyl-4-methyl-benzoic acid methyl ester (0.980 g, 5.15 mmol) in acetone (20 mL) and water (2.0 mL) are added N-methyl morpholine oxide (0.89 g, 7.57 mmol) and OsO$_4$ (1 mg). The resulting reaction mixture is stirred at room temperature for three hours. The reaction mixture is diluted with ethyl acetate (50 mL) and is washed with Na$_2$S$_2$O$_3$ (1.0 M, 20 mL). The organic layer are concentrated and the residue is dissolved in THF (25 mL) and water (15 mL). To the solution, NaIO$_4$ (3.24 g, 15.2 mmol) is added and the mixture is stirred at room temperature for two hours. The mixture is filtered and the filtrate is concentrated, diluted with ethyl acetate (60 mL), and washed with Na$_2$S$_2$O$_3$ (1.0 M, 20 mL). The organic layer is dried over sodium sulfate, filtered, and concentrated under reduced pressure. The crude residue is purified via flash chromatography eluting with 30-40% ethyl acetate in hexane to give the title compound (0.260 g, 26%). $^1$H NMR (400 MHz, CDCl$_3$) δ 9.74 (s, 1H), 7.94-7.92 (d, 1H), 7.15-7.13 (d, 1H), 7.00 (s, 1H), 3.99 (s, 2H), 3.81 (s, 3H), 2.35 (s, 3H).

The following list of compounds is prepared essentially according to the preparation of 4-Methyl-2-(2-oxo-ethyl)-benzoic acid methyl ester using the appropriate starting material.

Preparation 60A: 5-Methoxy-2-(2-oxo-ethyl)-benzoic acid methyl ester (29%), $^1$H NMR (400 MHz, CDCl$_3$) δ 9.72 (s, 1H), 7.54 (d, 1H), 7.12-7.10 (d, 1H), 7.14-7.00 (dd, 1H), 3.95 (s, 2H), 3.84 (s, 3H), 3.81 (s, 3H); Preparation 60B: 5-Methyl-2-(2-oxo-ethyl)-benzoic acid methyl ester (29%), $^1$H NMR (400 MHz, CDCl$_3$) δ 9.74 (s, 1H), 7.85 (d, 1H), 7.31-7.29 (dd, 1H), 7.10 (d, 1H), 3.99 (s, 2H), 3.84 (s, 3H), 2.36 (s, 3H); Preparation 60C: 4-Fluoro-2-(2-oxo-ethyl)-benzoic acid methyl ester (67%), $^1$H NMR (400 MHz, CDCl$_3$) δ 9.75 (s, 1H), 8.08-8.04 (dd, 1H), 7.05-7.01 (m, 1H), 6.93-6.90 (dd, 1H), 4.05 (s, 2H), 3.83 (s, 3H); Preparation 60D: 4-Methyl-3-(2-oxo-ethyl)-benzoic acid methyl ester (21%), $^1$H NMR (400 MHz, CDCl$_3$) δ 9.71 (s, 1H), 7.87-7.85 (d, 1H), 7.83 (s, 1H), 7.27-7.25 (d, 1H), 3.88 (s, 3H), 3.74 (s, 2H), 2.29 (s, 1H). Preparation 60E: 4-Fluoro-3-(2-oxo-ethyl)-benzoic acid methyl ester (44%), $^1$H NMR (400 MHz, CDCl$_3$) δ 9.72 (s, 1H), 7.97-7.93 (m, 1H), 7.88-7.86 (d, 1H), 7.12-7.08 (dd, 1H), 3.85 (s, 3H), 3.75 (s, 2H); Preparation 60F: 2-Fluoro-5-(2-oxo-ethyl)-benzoic acid methyl ester (30%), $^1$H NMR (400 MHz, CDCl$_3$) δ 9.74 (t, 1H), 7.77-7.75 (dd, 1H), 7.35-7.31 (m, 1H), 7.13-7.08 (dd, 1H), 3.90 (s, 3H), 3.70 (s, 2H).

Preparation 61

2-Butoxy-5-(2-oxo-ethyl)-benzoic Acid Methyl Ester

Step A

To a solution of 5-bromo-2-hydroxy-benzoic acid methyl ester (1.100 g, 4.76 mmol) in 5 mL DMF are added 1-iodobutane (1.31 g, 7.14 mmol) and potassium carbonate (1.31 g, 9.52 mmol). The resulting mixture is heated to 80° C. for 12 hours. The reaction is cooled to room temperature and quenched with water (30 mL) and extracted with ethyl acetate (30 mL×2). The combined organic layers are dried over sodium sulfate and are concentrated under reduced pressure. The residue is purified via chromatography eluting with 15% ethyl acetate in hexanes to give 1.35 g (99%) of the desired intermediate 5-bromo-2-butoxy-benzoic acid methyl ester. $^1$H NMR (400 MHz, CDCl$_3$) δ 7.85 (d, 1H), 7.50-7.47 (dd, 1H), 6.82-6.80 (d, 1H), 4.00-3.96 (t, 2H), 3.84 (s, 3H), 1.79-1.73 (m, 2H), 1.57-1.46 (m, 2H), 0.96-0.93 (t, 3H).

Step B

The title compound (30%) is prepared essentially according to the preparation of 4-Methyl-2-(2-oxo-ethyl)-benzoic acid methyl ester using 5-bromo-2-butoxy-benzoic acid methyl ester. $^1$H NMR (400 MHz, CDCl$_3$) δ 9.70 (s, 1H), 7.61 (d, 1H), 7.26-7.23 (dd, 1H), 6.94-6.92 (d, 1H), 4.02-3.99 (t, 2H), 3.85 (s, 3H), 3.62 (d, 2H), 1.80-1.76 (m, 2H), 1.52-1.47 (m, 2H), 0.96-0.93 (t, 3H).

Preparation 62

4-Butoxy-3-(2-oxo-ethyl)-benzoic Acid Methyl Ester

The title compound is prepared essentially according to the preparation of 2-Butoxy-5-(2-oxo-ethyl)-benzoic acid methyl ester (52%) using 3-bromo-4-hydroxy-benzoic acid methyl ester. $^1$H NMR (400 MHz, CDCl$_3$) δ 9.67 (d, 1H), 7.98-7.95 (d, 1H), 7.83 (s, 1H), 6.89-6.87 (d, 1H), 4.03-4.01 (t, 2H), 3.86 (s, 3H), 3.65 (d, 2H), 1.76-1.73 (m, 2H), 1.46-1.41 (m, 2H), 0.96-0.92 (t, 3H).

Preparation 63

2-Allyl-5-methoxy-benzoic Acid Methyl Ester

To an ambient temperature solution of 2-Bromo-5-methoxy-benzoic acid methyl ester (750 mg, 3.02 mmol) in benzene (2 mL) are added allyltri-n-butyl tin (1.16 mL, 3.73 mmol) and tetrakis(triphenylphosphine)palladium (0) (174 mg, 0.157 mmol, 5 mol %). The reaction mixture is heated in a sealed tube to 100° C. After 3 h, the reaction is concentrated under reduced pressure and the residue is chromatographed (0% to 10% EtOAc/Hex) to yield the title compound (451 mg, 73%). $^1$H NMR (400 MHz, CDCl$_3$) δ 7.40 (d, 1H, J=2.6 Hz), 7.18 (d, 1H, J=8.4 Hz), 7.00 (dd, 1H, J=8.6, 2.9 Hz), 6.04-5.93 (m, 1H), 5.03-4.94 (m, 2H), 3.88 (s, 3H), 3.82 (s, 3H), 3.70-3.65 (m, 2H).

Preparation 64

5-Methoxy-2-propyl-benzoic Acid Methyl Ester

To an ambient temperature suspension of 10% palladium on carbon (245 mg) in MeOH (5 mL) is added a solution of 2-Allyl-5-methoxy-benzoic acid methyl ester (440 mg, 2.13 mmol) in MeOH (5 mL) in one portion. The reaction is placed under an atmosphere of hydrogen gas and is stirred overnight. The reaction mixture is filtered through Celite® and concentrated to yield the title compound (361 mg, 81%). $^1$H NMR (400 MHz, CDCl$_3$) δ 7.38 (d, 1H, J=3.1 Hz), 7.15 (d, 1H, J=8.4 Hz), 6.97 (dd, 1H, J=8.6, 2.9 Hz), 3.89 (s, 3H), 3.82 (s, 3H), 2.88-2.82 (m, 2H), 1.65-1.53 (m, 2H), 0.95 (t, 3H, J=7.5 Hz).

Preparation 65

5-Hydroxy-2-propyl-benzoic Acid Methyl Ester

To a −78° C. solution of 5-Methoxy-2-propyl-benzoic acid methyl ester (350 mg, 1.68 mmol) in DCM (18 mL) is added boron tribromide (840 μL, 8.40 mmol, 1.0 M in DCM) dropwise. The reaction mixture is warmed to room temperature overnight. The reaction mixture is quenched by the dropwise addition of MeOH and is stirred at room temperature for 30 min. The reaction is concentrated and the residue is partitioned between EtOAc and water. The aqueous layer is extracted with EtOAc and the combined organic layers are washed with brine, dried (MgSO$_4$), filtered, concentrated, and chromatographed (0% to 20% EtOAc/Hex) to yield the title compound (274 mg, 84%) $^1$H NMR (400 MHz, CDCl$_3$) δ 7.34 (d, 1H, J=2.6 Hz), 7.11 (d, 1H, J=8.4 Hz), 6.92 (dd, 1H, J=8.4, 3.1 Hz), 6.92 (dd, 1H, J=8.4, 3.1 Hz), 3.88 (s, 3H), 2.87-2.81 (m, 2H), 1.63-1.52 (m, 2H), 0.94 (t, 3H, J=7.3 Hz).

Preparation 66

4-Hydroxy-2-methyl-benzoic Acid Methyl Ester

The title compound (77%) is prepared essentially according to the preparation of 5-hydroxy-2-propyl-benzoic acid methyl ester using 4-methoxy-2-methyl-benzoic acid methyl ester. $^1$H NMR (400 MHz, CDCl$_3$) δ 7.91-7.86 (m, 1H), 6.72-6.67 (m, 2H), 3.86 (s, 3H), 2.57 (s, 3H).

Preparation 67

4-Methoxy-2-methyl-benzoic Acid Methyl Ester

To an ambient temperature suspension of 4-Methoxy-2-methyl-benzoic acid (1.0 g, 6.02 mmol) in MeOH (10 mL) is added thionyl chloride (1.10 mL, 15.04 mmol) dropwise. The reaction mixture is heated to reflux. After 3 h, the reaction is concentrated and the residue is partitioned between EtOAc and NaHCO$_3$. The aqueous layer is extracted with EtOAc and the combined organic layers are washed with brine, dried (MgSO$_4$), filtered, and concentrated to yield the title compound (877 mg, 81%) $^1$H NMR (400 MHz, CDCl$_3$) δ 7.95-7.91 (m, 1H), 6.77-6.72 (m, 2H), 3.86 (s, 3H), 3.84 (s, 3H).

The following list of compounds is prepared essentially according to the preparation of 4-methoxy-2-methyl-benzoic acid methyl ester using the appropriate starting material.

Preparation 67A: 1-p-Tolyl-cyclopropanecarboxylic acid methyl ester (98%), $^1$H NMR (400 MHz, CDCl$_3$) δ 7.24 (d, 2H, J=7.9 Hz), 7.13 (d, 2H, J=8.4 Hz), 3.62 (s, 3H), 2.34 (s, 3H), 1.60-1.57 (m, 2H), 1.19-1.15 (m, 2H); Preparation 67B: 2-Methyl-2-p-tolyl-propionic acid methyl ester (84%), $^1$H NMR (400 MHz, CDCl$_3$) δ 7.23 (d, 2H, J=8.4 Hz), 7.14 (d, 2H, J=8.4 Hz), 3.65 (s, 3H), 2.33 (s, 3H), 1.57 (s, 6H); Preparation 67C: 2-Bromo-4-methyl-benzoic acid methyl ester, (quantitative), $^1$H NMR (400 MHz, CDCl$_3$) δ 7.73 (d, 1H, J=7.9 Hz), 7.49 (d, 1H, J=0.9 Hz), 7.15 (dd, 1H, J=7.6, 1.7 Hz), 3.91 (s, 3H), 2.36 (s, 3H).

Preparation 68

2-(4-Bromomethyl-phenyl)-2-methyl-propionic Acid Methyl Ester

To a refluxing solution of 2-Methyl-2-p-tolyl-propionic acid methyl ester (892 mg, 4.64 mmol) and N-bromosuccinimide (826 mg, 4.64 mmol) in CCl$_4$ (120 mL) is added 2,2'-Azobisisobutyronitrile (12 mg, 0.073 mmol). After 5 h, the reaction is concentrated and the residue is chromatographed (SiO$_2$ 120 g, 5% to 20% EtOAc/Hex) to yield the title compound (906 mg, 72%) $^1$H NMR (400 MHz, CDCl$_3$) δ 7.38-7.28 (m, 4H), 4.48 (s, 2H), 3.65 (s, 3H), 1.57 (s, 6H).

The following list of compounds is prepared essentially according to the preparation of 2-(4-Bromomethyl-phenyl)-2-methyl-propionic acid methyl ester using the appropriate starting material.

Preparation 68A: 1-(4-Bromomethyl-phenyl)-cyclopropanecarboxylic acid methyl ester (91%), $^1$H NMR (400 MHz, CDCl$_3$) δ 7.36-7.30 (m, 4H), 4.49 (s, 2H), 3.62 (s, 3H), 1.63-1.59 (m, 2H), 1.20-1.16 (m, 2H); Preparation 68B: 2-Bromo-4-bromomethyl-benzoic acid methyl ester (74%), $^1$H NMR (400 MHz, CDCl$_3$) δ 7.78 (d, 1H, J=8.4 Hz), 7.69 (d, 1H, J=1.3 Hz), 7.38 (dd, 1H, J=8.4, 1.8 Hz), 4.42 (s, 2H), 3.93 (s, 3H).

Preparation 69

2-(4-Formyl-phenyl)-2-methyl-propionic Acid Methyl Ester

To an ambient temperature solution of 2-(4-Bromomethyl-phenyl)-2-methyl-propionic acid methyl ester (275 mg, 1.01 mmol) in DMSO (8 mL) is added sodium bicarbonate (127 mg, 1.52 mmol). The reaction mixture is heated to 120° C. After 3 h, the reaction is concentrated and the residue is partitioned between EtOAc and NaHCO$_3$. The aqueous layer is extracted with EtOAc and the combined organic layers are washed with brine, dried (MgSO$_4$), filtered, concentrated, and chromatographed (0% to 20% EtOAc/Hex) to yield the title compound (179 mg, 86%). $^1$H NMR (400 MHz, CDCl$_3$) δ 10.00 (s, 1H), 7.85 (d, 2H, J=8.4 Hz), 7.50 (d, 2H, J=8.4 Hz), 3.67 (s, 3H), 1.61 (s, 6H).

The following list of compounds is prepared essentially according to the preparation of 2-(4-Formyl-phenyl)-2-methyl-propionic acid methyl ester using the appropriate starting material.

Preparation 69A: 1-(4-Formyl-phenyl)-cyclopropanecarboxylic acid methyl ester (89%), $^1$H NMR (400 MHz, CDCl$_3$) δ 10.00 (s, 1H), 7.83 (d, 2H, J=8.4 Hz), 7.51 (d, 2H, J=8.4 Hz), 3.64 (s, 3H), 1.70-1.65 (m, 2H), 1.25-1.21 (m, 2H); Preparation 69B: 2-Bromo-4-formyl-benzoic acid methyl ester (52%), $^1$H NMR (400 MHz, CDCl$_3$) δ 10.02 (s, 1H), 8.14 (d, 1H, J=1.3 Hz), 7.90 (d, 1H, J=7.9 Hz), 7.86 (dd, 1H, J=6.9, 1.0 Hz), 3.97 (s, 3H).

Preparation 70

4-(2-Methoxy-vinyl)-benzoic Acid Methyl Ester

To an ambient temperature suspension of potassium tert-butoxide (2.05 g, 18.27 mmol) in THF (60 mL) is added the (methoxymethyl)triphenyl phosphonium chloride (6.26 g, 18.27 mmol). The reaction mixture is stirred at room temperature for 20 min. Solid methyl 4-formylbenzoate (1.0 g, 6.09 mmol) is added and the reaction is stirred at room temperature overnight. The reaction mixture is quenched with saturated aq. NH₄Cl and concentrated. The residue is partitioned between Et₂O and water. The aqueous layer is extracted with Et₂O and the combined organic layers are washed with brine, dried (MgSO₄), filtered, concentrated, and chromatographed (0% to 30% EtOAC/Hex) to yield the title compound (939 mg, 80%) as a mix of E/Z isomers.

$^1$H NMR (400 MHz, CDCl$_3$) δ 8.04 (d, 1H, J=7.9 Hz), 7.89 (d, 1H, J=7.9 Hz), 7.82 (dd, 1H, J=7.9, 1.3 Hz), 8.04 (dd, 1H, J=7.9, 0.9 Hz), 7.41-7.39 (m, 2H), 7.23-7.17 (m, 1H), 6.99 (d, 1H, J=12.8 Hz), 6.74 (d, 1H, J=12.8 Hz), 6.22 (d, 1H, J=7.0 Hz), 6.06 (d, 1H, J=7.0 Hz), 3.89 (s, 6H), 3.76 (s, 3H), 3.73 (s, 3H).

The following list of compounds is prepared essentially according to the preparation of 4-(2-Methoxy-vinyl)-benzoic acid methyl ester using the appropriate starting material.

Preparation 70A: 3-(2-Methoxy-vinyl)-benzoic acid methyl ester (73%), $^1$H NMR (400 MHz, CDCl$_3$) δ 8.14 (s, 1H), 7.88 (s, 1H), 7.80-7.74 (m, 3H), 7.40-7.27 (m, 3H), 7.09 (d, 2H, J=13.1 Hz), 6.17 (d, 1H, J=7.1 Hz), 5.81 (d, 1H, J=12.7 Hz), 5.23 (d, 1H, J=7.0 Hz), 3.89 (s, 6H), 3.78 (s, 3H), 3.68 (s, 3H); Preparation 70B: 3-(2-Methoxy-vinyl)-benzoic acid methyl ester (60%), $^1$H NMR (400 MHz, CDCl$_3$) δ 8.04 (d, 1H, J=7.9 Hz), 7.89 (d, 1H, J=7.9 Hz), 7.82 (dd, 1H, J=7.9, 1.3 Hz), 8.04 (dd, 1H, J=7.9, 0.9 Hz), 7.41-7.39 (m, 2H), 7.23-7.17 (m, 1H), 6.99 (d, 1H, J=12.8 Hz), 6.74 (d, 1H, J=12.8 Hz), 6.22 (d, 1H, J=7.0 Hz), 6.06 (d, 1H, J=7.0 Hz), 3.89 (s, 6H), 3.76 (s, 3H), 3.73 (s, 3H).

Preparation 71

4-(2-Oxo-ethyl)-benzoic Acid Methyl Ester

To a 0° C. solution of 4-(2-Methoxy-vinyl)-benzoic acid methyl ester (930 mg, 4.84 mmol) in THF (50 mL) is added conc. HCl (7 mL) dropwise. After 2 h, the reaction is diluted with water and the pH is adjusted to 7. The aqueous layer is extracted with Et₂O (2×200 mL). The combined organic layers are washed with brine, dried (MgSO₄), filtered, concentrated, and chromatographed (0% to 30% EtOAC/Hex) to yield the title compound (613 mg, 71%). $^1$H NMR (400 MHz, CDCl$_3$) δ 9.77 (t, 1H, J=2.2 Hz), 8.04 (d, 2H, J=8.4 Hz), 7.30 (d, 2H, J=8.8 Hz), 3.92 (s, 3H), 3.77 (d, 2H, J=2.2 Hz).

The following list of compounds is prepared essentially according to the preparation of 4-(2-Oxo-ethyl)-benzoic acid methyl ester using the appropriate starting material.

Preparation 71A: 3-(2-Oxo-ethyl)-benzoic acid methyl ester (59%), $^1$H NMR (400 MHz, CDCl$_3$) δ 9.78 (t, 1H, J=2.2 Hz), 7.98 (d, 1H, J=7.5 Hz), 7.91 (s, 1H), 7.48-7.39 (m, 2H), 7.48-7.39 (m, 2H), 3.92 (s, 3H), 3.77 (d, 2H, J=2.2 Hz); Preparation 71B: 2-(2-Oxo-ethyl)-benzoic acid methyl ester (62%), $^1$H NMR (400 MHz, CDCl$_3$) δ 9.79 (t, 1H, J=1.3 Hz), 8.13-8.05 (m, 2H), 7.58-7.49 (m, 1H), 7.42-7.37 (m, 1H), 7.31-7.23 (m, 1H), 4.07 (d, 2H, J=1.3 Hz), 3.88 (s, 3H).

Preparation 72

(4-Mercapto-phenyl)-acetic Acid Methyl Ester

To an ambient temperature solution of 4-Mercaptophenylacetic acid (5.0 g, 29.72 mmol) in MeOH (250 mL) is added sulfuric acid (1.25 mL). The reaction mixture is stirred at room temperature overnight. The reaction is concentrated and the residue is partitioned between Et₂O and water. The aqueous layer is extracted with Et₂O and the combined organic layers are washed with brine, dried (MgSO₄), filtered, concentrated, and chromatographed (0% to 30% EtOAC/Hex) to yield the title compound (3.69 g, 68%). $^1$H NMR (400 MHz, CDCl$_3$) δ 7.21 (d, 2H, J=7.9 Hz), 7.12 (d, 2H, J=8.4 Hz), 3.66 (s, 3H), 3.54 (s, 2H).

Preparation 73

1-(4-Benzyloxy-2-methyl-phenyl)-ethanone

To a solution of Hydroxy-2'-methylacetophenone (5.508 g, 0.037 mol) in DMF (10 mL) is added cesium carbonate (23.8 g, 0.073 mol). The reaction is stirred at room temperature for 10 minutes. Benzyl bromide (4.36 mL, 0.037 mol) is added and after 1 hour at room temperature, the reaction is concentrated under reduced pressure. The residue is dissolved in ethyl acetate and water. The layers are separated and the organic phase is washed with brine, dried over magnesium sulfate, filtered, and concentrated under reduced pressure to give the title compound. ES/MS m/e 241.0 (M+1)

Preparation 74

(E/Z)-3-(4-Benzyloxy-2-methyl-phenyl)-but-2-enoic Acid Ethyl Ester

To a solution of triethyl phosphohonacetate (1.25 mL, 0.006 mol) in DMF (5 mL) is added sodium hydride (0.25 g, 0.006 mol). After 30 minutes, 1-(4-benzyloxy-2-methyl-phenyl)-ethanone (0.5 g, 0.002 mol) is added and the reaction is heated to 80° C. overnight. Upon cooling, water is added followed by 1N HCl. The aqueous layer is extracted two times with ethyl acetate and the organic layers are combined, washed with brine, dried over magnesium sulfate, filtered and concentrated under reduced pressure to give the title compound. $^1$H NMR (CDCl$_3$) δ 1.27 (t, 3H), 2.25 (s, 3H), 2.4 (s, 3H), 4.17 (q, 2H), 5.0 (s, 2H), 5.72 (s, 1H), 6.75 (dd, 1H), 6.8 (s, 1H), 6.98 (d, 1H), 7.27-7.45 (m, 5H)

Preparation 75

(+/−)-3-(4-Hydroxy-2-methyl-phenyl)-butyric Acid Ethyl Ester

To a solution of (E/Z)-3-(4-Benzyloxy-2-methyl-phenyl)-but-2-enoic acid ethyl ester in ethyl alcohol is added 10% palladium on carbon. The reaction is placed under 413.8 kPa of hydrogen gas for 6 hours. The catalyst is filtered over diatomaceous earth and the filtrate is concentrated under reduced pressure to give the title compound. ES/MS m/e 221.0 (M−1)

Preparation 76

(+/−)-3-{4-[2-(2,6-Dichloro-phenyl)-4-isopropyl-2H-pyrazol-3-ylmethoxy]-2-methyl-phenyl}-butyric Acid Ethyl Ester To a solution of (+/−)-3-(4-Hydroxy-2-methyl-phenyl)-butyric acid ethyl ester (0.366 g, 0.748 mmol) in DMF (4 mL) is added cesium carbonate (1.1 g, 1.5 mmol). After 5 minutes at room temperature, 5-Chloromethyl-1-(2,6-dichloro-phenyl)-4-isopropyl-1H-pyrazole (0.50 g, 0.748 mmol) is added and the reaction is heated to 50° C. overnight. Upon cooling, water is added followed by 1N HCl. The resulting mixture is extracted two times with ethyl acetate and the organic layers are combined and are washed with brine, dried over magnesium sulfate, filtered, and concentrated under reduced pressure. The residue is purified via flash chromatography eluting with 3-5% ethyl acetate/toluene to give the title compound. $^1$H NMR (CDCl$_3$) δ 1.113-1.163 (m, 6H), 1.26 (d, 6H), 2.399-2.532 (m, 2H), 2.952 (m, 1H), 3.388 (m, 1H), 4.024 (q, 2H), 4.741 (s, 2H), 6.513 (d, 1H), 6.544 (dd, 1H), 6.970 (d, 1H), 7.264 (t, 1H), 7.372 (d, 2H), 7.661 (s, 1H)

Preparation 77

(+/−)-3-{4-[2-(2,6-Dichloro-phenyl)-4-isopropyl-2H-pyrazol-3-ylmethoxy]-2-methyl-phenyl}-butan-1-ol (+/−)-3-{4-[2-(2,6-Dichloro-phenyl)-4-isopropyl-2H-pyrazol-3-ylmethoxy]-2-methyl-phenyl}-butyric acid ethyl ester (0.581 g, 1.19 mmol) is dissolved in THF (15 mL) and methyl alcohol (3 mL). Sodium borohydride is added portionwise until an excess has been added. After stirring at room temperature for 3 days, the reaction is quenched with water followed by 1N HCl. The resulting mixture is extracted two times with ethyl acetate. The organic layers are combined, washed with brine, dried over magnesium sulfate, filtered, and concentrated under reduced pressure. The residue is purified via flash chromatography eluting with 5-10% ethyl acetate:toluene to give the title compound. $^1$H NMR (CDCl$_3$) δ 1.134 (d, 3H), 1.262 (d, 6H), 1.456 (s, 2H), 1.764 (m, 2H), 2.223 (s, 3H), 2.939-3.039 (m, 2H), 3.476-3.539 (m, 2H), 4.747 (s, 2H), 6.516 (d, 1H), 6.559 (dd, 1H), 6.99 (d, 1H), 7.263 (t, 1H), 7.372 (d, 2H), 7.663 (s, 1H)

Preparation 78

(+/−)-3-Nitro-benzenesulfonic acid 3-{4-[2-(2,6-dichloro-phenyl)-4-isopropyl-2H-pyrazol-3-ylmethoxy]-2-methyl-phenyl}-butyl Ester To a solution of (+/−)-3-{4-[2-(2,6-Dichloro-phenyl)-4-isopropyl-2H-pyrazol-3-ylmethoxy]-2-methyl-phenyl}-butan-1-ol (0.245 g, 0.548 mmol) in dichloromethane (10 mL) is added triethylamine (0.15 mL, 1.09 mmol). After 10 minutes, m-nitrobenzene sulfonyl chloride (0.243 g, 1.09 mmol) is added. The reaction is stirred at room temperature for 4 hours and the reaction mixture is concentrated under reduced pressure. The residue is dissolved in ethyl acetate and is washed with water and brine, dried over magnesium sulfate, filtered, and concentrated under reduced pressure to give the title compound. $^1$H NMR (CDCl$_3$) δ 1.1 (d, 3H), 1.28 (d, 6H), 1.62 (s, 2H), 1.85-1.95 (m, 2H), 2.17 (s, 3H), 2.91-3.039 (m, 2H), 3.85-3.95 (m, 1H), 4.04-4.12 (m, 2H), 4.74 (s, 2H), 6.45 (d, 1H), 6.51 (dd, 1H), 6.86 (d, 1H), 7.26 (t, 1H), 7.38 (d, 2H), 7.65 (t, 3H), 8.1 (d, 1H), 8.39 (d, 1H), 8.63 (s, 1H);

Preparation 79

(+/−)-Toluene-4-sulfonic acid 3-{4-[2-(2,6-dichloro-phenyl)-4-isopropyl-2H-pyrazol-3-ylmethoxy]-2-methyl-phenyl}-butyl Ester The title compound is prepared essentially according to the preparation of (+/−)-3-Nitro-benzenesulfonic acid 3-{4-[2-(2,6-dichloro-phenyl)-4-isopropyl-2H-pyrazol-3-ylmethoxy]-2-methyl-phenyl}-butyl ester using the appropriate starting material. $^1$H NMR (CDCl$_3$) δ 1.057 (d, 6H), 1.264 (d, 6H), 1.825 (q, 2H), 2.145 (s, 3H), 2.394 (s, 3H), 2.969 (q, 2H), 3.813 (m, 1H), 3.935 (m, 1H), 4.744 (s, 2H), 6.477 (d, 1H), 6.494 (dd, 1H), 6.864 (d, 1H), 7.26 (t, 3H), 7.373 (d, 2H), 7.682 (d, 3H);

Preparation 80

4-[1-(4-Hydroxy-2-methyl-phenyl)-ethylamino]-benzoic Acid Methyl Ester

A mixture of methyl-4-amino benzoate (260 mg, 1.72 mmol) and 4'-hydroxy-2'-methyl acetophenone in glacial acetic acid (8 mL) is heated to 50° C. for 50 minutes. The mixture is cooled to room temperature and sodium triacetoxy borohydride (750 mg, 3.54 mmol) is added. After 20 hours, more sodium triacetoxy borohydride (750 mg, 3.54 mmol) is added. Again after 24 hours, more sodium triacetoxy borohydride (750 mg, 3.54 mmol) is added. After seven hours, the mixture is concentrated and the residue is partitioned between ethyl acetate and saturated sodium bicarbonate. The layers are separated and the aqueous layer is extracted with ethyl acetate (2×). The combined ethyl acetate layers are dried (MgSO$_4$) and concentrated under reduced pressure. The residue is purified by flash chromatography to provide the title compound (84 mg, 17%). 1H-NMR (DMSO-d$_6$, 400 MHz), δ 9.06 (s, 1H), 7.55 (d, J=9.2 Hz, 2H), 7.02 (d, 8.4 Hz, 1H), 6.87 (d, 6.8 Hz, 1H), 6.51-6.39 (m, 4H), 4.53 (m, 1H), 3.66 (s, 3H), 2.25 (s, 3H), 1.31 (d, 6.4 Hz, 3H).

Preparation 81

3-(4-Hydroxy-2-methyl-benzylamino)-benzoic Acid Ethyl Ester

Step A

A mixture of 2-methyl-4-benzyloxy benzaldehyde (1.22 g, 5.39 mmol) and ethyl-3-amino benzoate (912 mg, 5.52 mmol) in glacial acetic acid (40 mL) is stirred for 30 minutes. To the mixture, sodium triacetoxy borohydride (1.25 g, 5.90 mmol) is added. After 20 hours the mixture is concentrated and the residue is partitioned between ethyl acetate and saturated sodium bicarbonate. The layers are separated and the aqueous layer is extracted with ethyl acetate (2×). The combined ethyl acetate layers are dried (MgSO$_4$) and concentrated. The residue is purified by flash chromatography to provide benzyl intermediate (1.6 g, 80%).

Step B

To a solution of the benzyl intermediate from step A (471 mg, 1.25 mmol) in ethyl acetate (20 mL) under nitrogen is added 10% palladium on carbon (80 mg). The mixture is evacuated and is stirred under hydrogen overnight. The mixture is filtered over Celite® and concentrated under reduced pressure to provide the title product as a solid (300 mg, 84%). ES/MS m/e 284.3 (M−1).

Preparation 82

4-(4-Hydroxy-2-methyl-benzylamino)-benzoic Acid Methyl Ester

The title compound (546 mg, 91%) is prepared essentially according to the procedure for 3-(4-Hydroxy-2-methyl-benzylamino)-benzoic acid ethyl ester using 2-methyl-4-benzyloxy benzaldehyde and methyl-4-amino benzoate. ES/MS m/e 270.3 (M−1)

Preparation 83

4-Formyl-2-pent-1-ynyl-benzoic Acid Methyl Ester

To a room temperature solution of 2-Bromo-4-formyl-benzoic acid methyl ester (500 mg, 2.05 mmol) in degassed DMF (5 mL) are added triethylamine (2.0 mL, 14.35 mmol), dichlorobis(triphenylphosphine)palladium (II) (144 mg, 0.205 mmol, 10 mol %), copper (I) iodide (20 mg, 0.103 mmol, 5 mol %), and 1-Pentyne (406 μL, 4.10 mmol). The reaction mixture is heated to 80° C. in a sealed tube. After 2 h, the reaction is concentrated and the residue is chromatographed (0% to 10% EtOAc/Hex) to yield the title compound (279 mg, 59%). $^1$H NMR (400 MHz, CDCl$_3$) δ 10.03 (s, 1H), 8.02-7.98 (m, 2H), 7.80 (dd, 1H, J=7.9, 1.8 Hz), 3.95 (s, 3H), 2.48 (t, 2H, J=7.0 Hz), 1.73-1.63 (m, 2H), 1.09 (t, 3H, J=7.5 Hz).

Preparation 84

4-Formyl-2-methyl-benzoic Acid Methyl Ester

Under a N$_2$ atmosphere, a 1 L Parr autoclave is charged with palladium (II) acetate (2.19 g, 0.0097 mol) and butyl-1-diadamantylphosphine (10.42 g, 0.291 mol) in toluene (100 mL). To this mixture are added (4-bromo-2-methyl-benzoic acid methyl ester (222 g, 0.969 mol) and tetramethylethylenediamine (97.1 mL, 0.63 equiv) in toluene (325 mL). The autoclave is sealed and removed from N$_2$ atmosphere. To the autoclave, a constant pressure of SynGas® (equal CO/H$_2$ mix, 75 psi) is placed. The reaction is stirred for 18 hours at 85° C. The crude mixture is filtered through a Celite® pad and is washed with CH$_2$Cl$_2$ until clear. The solvent is removed under reduced pressure to produce a red oil (86%) that will crystallize upon standing. $^1$H NMR (400 MHz, CDCl$_3$) δ 2.6 (3H, s), 3.85 (3H, s), 7.65-8.0 (3H, m), 10.0 (1H, s).

The following list of compounds is prepared essentially according to the preparation of 4-formyl-2-methyl-benzoic acid methyl ester using the appropriate starting material.

Preparation 84A: 2-Benzyloxy-4-formyl-benzoic acid methyl ester (384 mg, 86%), LC-ES/MS m/e 293.0 (M+23); Preparation 84B: 4-Formyl-2-trifluoromethyl-benzoic acid methyl ester (1.29 g, 92%), LC-ES/MS m/e 233.3 (M+1); Preparation 84C: 3-Formyl-5-trifluoromethyl-benzoic acid methyl ester (0.5 g, 78%), $^1$HNMR (CDCl$_3$) (ppm): 3.95 (3H, s), 8.25 (1H, s), 8.5 (1H, s), 8.7 (1H, s), 10.1 (1H, s).

Preparation 85

(4-Iodo-3-methyl-phenyl)-methanol

To a solution of 4-Iodo-3-methyl-benzoic acid (5.2 g, 20 mmol) in THF (30 mL) is added 2.0 M borane-dimethyl sulfide complex in THF (40.0 mL, 80 mmol) dropwise. The mixture is stirred overnight. The reaction mixture is quenched carefully at 0° C. with methanol (20 mL) and the mixture is evaporated to dryness under reduced pressure. The residue is partitioned between EtOAc (80 mL) and water (60 mL). The organic phase is washed with brine (60 mL), dried (Na$_2$SO$_4$), filtered, and concentrated under reduced pressure to a residue. The residue is purified by flash chromatography (gradient EtOAc/Hexane) to afford the title compound as white solid (4.7 g, 95%). $^1$HNMR (CDCl$_3$) (ppm): 2.4 (3H, s), 4.55 (2H, s), 6.8-7.75 (3H, m).

The following list of compounds is prepared essentially according to the preparation of (4-iodo-3-methyl-phenyl)-methanol using the appropriate starting material.

Preparation 85A: (4-Iodo-3-trifluoromethyl-phenyl)-methanol (2.1 g, 92%), $^1$HNMR (CDCl$_3$) (ppm): 2.18 (1H, s), 4.8 (2H, s), 7.4-8.0 (3H, m); Preparation 85B: (3-Iodo-5-trifluoromethyl-phenyl)-methanol (2.1 g, 92%), $^1$HNMR (CDCl$_3$) (ppm): 2.7 (1H, s), 4.65 (2H, s), 7.5-7.85 (3H, m).

Preparation 86

4-Hydroxymethyl-2-methyl-benzoic Acid Methyl Ester

To a 50 mL hastalloy Parr pressure reactor are added palladium acetate (0.161 g, 0.7 mmol, 1,4 bis-(diphenylphosphino)butane (DPPB) (0.363 g, 0.85 mmol), (4-Iodo-3-methyl-phenyl)-methanol (1.80 g, 7.25 mmol), dry methanol (10.0 mL), dry triethylamine (5.25 mL, 37.7 mmol) and dry acetonitrile (15.0 mL). The reaction vessel is evacuated and filled with nitrogen (4×). Next, the reaction vessel is evacuated and filled with carbon monoxide (4×). The reaction vessel is pressurized with carbon monoxide (100 psig, 690 KPa), sealed, and agitated at 100° C. for 4 hours while the carbon monoxide pressure is maintained at 100 psig. The reaction is cooled to ambient temperature and the carbon monoxide is vented from the reaction vessel. After filtration, the filtrate is concentrated to a residue. The residue is partitioned between EtOAc (50 mL) and water (50 mL). The organic phase is washed with brine (50 mL), dried (Na$_2$SO$_4$), filtered, and concentrated under reduced pressure to a residue. The residue is purified by flash chromatography to afford the title compound as syrup (1.18 g, 90%). LC-ES/MS m/e 181.3 (M+1).

The following list of compounds is prepared essentially according to the preparation of 4-hydroxymethyl-2-methyl-benzoic acid methyl ester using the appropriate starting material.

Preparation 86A: 2-Benzyloxy-4-hydroxymethyl-benzoic acid methyl ester (450 mg, 40%), LC-ES/MS m/e 273.0 (M+1); Preparation 86B: 4-Methyl-naphthalene-1-carboxylic acid methyl ester (3.85 g, 85%), LC-ES/MS m/e 201.0 (M+1); Preparation 86C: 4-Hydroxymethyl-2-trifluoromethyl-benzoic acid methyl ester (1.42 g, 87%), LC-ES/MS m/e 235.0 (M+1); Preparation 86D: 3-Hydroxymethyl-5-trifluoromethyl-benzoic acid methyl ester (0.65 g, 24%), $^1$HNMR (CDCl$_3$) (ppm): 3.05 (1H, br s), 3.9 (3H, s), 4.7 (2H, s), 7.75 (1H, s), 8.1 (2H, s); Preparation 86E: 2-Benzoyl-4-methyl-benzoic acid methyl ester (67 g, 49%), LC-ES/MS m/e 255.3 (M+1).

Preparation 87

4-Formyl-2-methyl-benzoic Acid Methyl Ester

To a 0° C. solution of 4-hydroxymethyl-2-methyl-benzoic acid methyl ester (0.49 g, 2.7 mmol) in methylene chloride (8.0 mL) are added sodium bicarbonate (0.46 g, 5.4 mmol) and Dess-Martin periodinane (0.14 g, 3.3 mmol) sequentially. The mixture is stirred at room temperature for 1.0 h and is quenched with water (2.0 mL). The mixture is partitioned between CH$_2$Cl$_2$ (30 mL) and water (30 mL). The organic phase is washed with brine (30 mL), dried (Na$_2$SO$_4$), filtered, and concentrated under reduced pressure to a residue. The residue is purified by flash chromatography to afford the title compound as syrup (0.35 g, 72%). $^1$HNMR (CDCl$_3$) (ppm): 2.6 (3H, s), 3.85 (3H, s), 7.65-8.0 (3H, m), 10.0 (1H, s).

The following list of compounds is prepared essentially according to the preparation of 4-formyl-2-methyl-benzoic acid methyl ester using the appropriate starting material.

Preparation 87A: 2-Bromo-4-formyl-benzoic acid methyl ester (440 mg, 61%), LC-ES/MS m/e 261.0 (M+18); Preparation 87B: 2-Butoxy-4-formyl-benzoic acid methyl ester (240 mg, 90%), LC-ES/MS m/e 237.3 (M+1); Preparation 87C: 2-Butyrylamino-4-formyl-benzoic acid methyl ester (550 mg, 87%), LC-ES/MS m/e 250.3 (M+1), 248.3 (M−1); Preparation 87D: 4-Formyl-2-(propane-1-sulfonylamino)-benzoic acid methyl ester (447 mg, 82%), LC-ES/MS m/e 303.3 (M+18), 284.3 (M−1).

Preparation 88

3-Benzyloxy-4-iodo-benzoic Acid Methyl Ester

The mixture of 3-hydroxy-4-iodo-benzoic acid methyl ester (1.2 g, 4.3 mmol), potassium carbonate (1.78 g, 13 mmol), acetone (15.0 mL), benzyl bromide (1.5 g, 8.6 mmol), and TBAI (0.05 g) is heated to 50° C. overnight. The solvent is removed under reduced pressure. The residue is partitioned between EtOAc (30 mL) and water (30 mL). The organic phase is washed with brine (20 mL), dried ($Na_2SO_4$), filtered, and concentrated under reduced pressure to a residue. The residue is purified by flash chromatography to afford the title compound as white solid (1.58 g, 99%). LC-ES/MS m/e 386.0 (M+18).

Preparation 89

3-Benzyloxy-4-iodo-phenyl)-methanol

The mixture of 3-benzyloxy-4-iodo-benzoic acid methyl ester (1.58 g, 4.3 mmol), lithium hydroxide (0.52 g, 21 mmol), THF (10 mL), MeOH (10 mL) and water (10 mL) is stirred at room temperature for 2.0 h and is acidified with 1.0 M HCl. The mixture is partitioned between EtOAc (30 mL) and water (30 mL). The organic phase is washed with brine (20 mL), dried ($Na_2SO_4$), filtered, and concentrated under reduced pressure to give the intermediate product. The intermediate product is dissolved in THF (20 mL), and is treated with 2.0 M borane-dimethyl sulfide complex in THF (10 mL, 20 mmol) overnight. The reaction mixture is quenched carefully at 0° C. with methanol (10 mL) and is evaporated to dryness under reduced pressure. The residue is partitioned between EtOAc (30 mL) and water (30 mL). The organic phase is washed with brine (30 mL), dried ($Na_2SO_4$), filtered, and concentrated under reduced pressure to a residue. The residue is purified by flash chromatography to afford the title compound as white solid (1.32 g, 90%). LC-ES/MS m/e 358.0 (M+18).

Preparation 90

2-Isopropoxy-4-methyl-benzoic Acid Methyl Ester

To a mixture of 2-hydroxy-4-methyl-benzoic acid methyl ester (1.0 g, 6.0 mmol), triphenylphosphine (1.9 g, 7.2 mmol), and isopropanol (0.72 g, 12.0 mmol) in THF (10.0 mL) is added DIAD (1.45 g, 7.2 mmol) dropwise at 0° C. The mixture is stirred at room temperature overnight. The mixture is evaporated to dryness under reduced pressure. The residue is partitioned between EtOAc (50 mL) and water (50 mL). The organic phase is washed with brine (50 mL), dried ($Na_2SO_4$), filtered, and concentrated under reduced pressure to a residue. The residue is purified by flash chromatography to afford the title compound as white solid (1.4 g, 96%). LC-ES/MS m/e 209.0 (M+1).

The following list of compounds is prepared essentially according to the preparation of 2-isopropoxy-4-methyl-benzoic acid methyl ester using the appropriate starting material.

Preparation 90A: 2-Butoxy-4-methyl-benzoic acid methyl ester (1.0 g, 74%), LC-ES/MS m/e 223.3 (M+1); Preparation 90B: 2-Butoxy-5-methyl-benzoic acid methyl ester (0.85 g, 64%), LC-ES/MS m/e 223.3 (M+1); Preparation 90C: 5-Butoxy-isophthalic acid dimethyl ester (2.1 g, 83%), LC-ES/MS m/e 284.0 (M+1).

Preparation 91

4-Bromomethyl-2-isopropoxy-benzoic Acid Methyl Ester

The mixture of 2-isopropoxy-4-methyl-benzoic acid methyl ester (1.0 g, 4.8 mmol), dibenzoyl peroxide (100 mg), and NBS (0.85 g, 4.8 mmol) in $CCl_4$ (20 mL) is heated at 70° C. overnight. The solid is filtered off and the filtrate is concentrated to a residue. The residue is purified by flash chromatography to afford the title compound as white solid (0.7 g, 51%). LC-ES/MS m/e 287.0 (M+1).

The following list of compounds is prepared essentially according to the preparation of 4-bromomethyl-2-isopropoxy-benzoic acid methyl ester using the appropriate starting material.

Preparation 91A: 4-Bromomethyl-2-butoxy-benzoic acid methyl ester (0.6 g, 52%), LC-ES/MS m/e 301.0 (M+1); Preparation 91B: 5-Bromomethyl-2-butoxy-benzoic acid methyl ester (0.44 g, 65%), LC-ES/MS m/e 301.0 (M+1); Preparation 91C: 3-Bromomethyl-5-methyl-benzoic acid methyl ester (2.73 g, 62%), LC-ES/MS m/e 260.0 (M+18); Preparation 91D: 6-Bromomethyl-nicotinic acid methyl ester (575 mg, 43%), LC-ES/MS m/e 230.0 (M+1); Preparation 91E: 4-Bromomethyl-2,3-difluoro-benzoic acid methyl ester (1.95 g, 76%), LC-ES/MS m/e 282.0 (M+18); Preparation 91F: 4-Bromomethyl-3-trifluoromethyl-benzoic acid methyl ester (0.7 g, 89%), $^1$HNMR ($CDCl_3$) (ppm): 3.85 (3H, s), 4.6 (2H, s), 7.4-8.3 (3H, m); Preparation 91G: 2-Bromo-4-methyl-benzoic acid (4.3 g, 63%), LC-ES/MS m/e 292.7 (M−1); Preparation 91H: 4-Bromomethyl2-butyrylamino-benzoic acid methyl ester (2.9 g, 98%). LC-ES/MS m/e 314.0 (M+1); Preparation 91I: 4-Bromomethyl-naphthalene-1-carboxylic acid methyl ester (1.44 g, 86%), LC-ES/MS m/e 281.0 (M+1); Preparation 91J: 2-Benzoyl-4-bromomethyl-benzoic acid methyl ester (450 mg, 51%), LC-ES/MS m/e 333.0 (M+1); Preparation 91K: 4-Bromomethyl-2-(propane-1-sulfonylamino)-benzoic acid methyl ester (3.75 g, 91%), LC-ES/MS m/e 350.0 (M+1), 367.0 (M+18).

Preparation 92

2,3-Difluoro-4-methyl-benzoic Acid Methyl Ester

To a solution of 2,3-difluoro-4-methyl-benzoic acid (5.0 g, 29 mmol) in $CH_2Cl_2$ (20 mL) and MeOH (20 mL) is added 2.0 M $TMSCHN_2$ in hexane (17.5 mL, 34.9 mmol) at 0° C. The reaction mixture is stirred for 1.0 h. The reaction mixture is concentrated to a residue and the residue is purified by flash chromatography to afford the title compound as an oil (5.7 g, 100%). LC-ES/MS m/e 208.3 (M+23).

Preparation 93

4-Methyl-3-trifluoromethyl-benzoic Acid Methyl Ester

The title compound (580 mg, 95%) is prepared essentially according to the preparation of 2,3-difluoro-4-methyl-benzoic acid methyl ester using 4-methyl-3-trifluoromethyl acid. LC-ES/MS m/e 236.3 (M+18).

Preparation 94

2-Bromo-4-hydroxymethyl-benzoic Acid Methyl Ester

The mixture of 2-bromo-4-methyl-benzoic acid (9.5 g, 32.3 mmol), THF (30.0 mL), and 5.0 M NaOH (26 mL, 129 mmol) is stirred at room temperature overnight. The mixture is acidified with 5.0 M HCl and is extracted with EtOAc (80 mL). The organic phase is washed with brine (60 mL) and is dried ($Na_2SO_4$). After filtration, the filtrate is concentrated under reduced pressure to a residue. The residue is dissolved in $CH_2Cl_2$ (50 mL) and MeOH (50 mL) and is treated with 2.0 M $TMSCHN_2$ in hexane (30 mL, 60 mmol) at 0° C. for 1.0 h. The reaction mixture is concentrated to a residue and the residue is purified by flash chromatography to afford the title compound as a solid (2.3 g, 29%). LC-ES/MS m/e 247.0 (M+1).

The following list of compounds is prepared essentially according to the preparation 2-bromo-4-hydroxymethyl-benzoic acid methyl ester using the appropriate starting material.

Preparation 94A: 2-Butoxy-4-hydroxymethyl-benzoic acid methyl ester (270 mg, 68%), LC-ES/MS m/e 239.3 (M+1); Preparation 94B: 4-Hydroxymethyl-2-(propane-1-sulfonylamino)-benzoic acid methyl ester (580 mg, 19%), LC-ES/MS m/e 305.0 (M+18), 286.3 (M−1); Preparation 94C: 2-Butyrylamino-4-hydroxymethyl-benzoic acid methyl ester (640 mg, 28%), LC-MS: 252.3 (M+1).

Preparation 95

2-Bromo-4-[1,3]dioxin-2-yl-benzoic Acid Methyl Ester

The mixture of 2-bromo-4-formyl-benzoic acid methyl ester (440 mg, 1.8 mmol), ethylene glycol (1.1 g, 18 mmol) and p-toluene sulfonic acid (30 mg) in THF (10 mL) is stirred at room temperature overnight. The reaction mixture is partitioned between EtOAc (30 mL) and water (30 mL). The organic phase is washed with brine (30 mL), dried ($Na_2SO_4$), filtered, and concentrated under reduced pressure to a residue. The residue is purified by flash chromatography to afford the title compound as syrup (380 mg, 73%). LC-ES/MS m/e 287.0 (M+1).

Preparation 96

4-[1,3]Dioxin-2-yl-2-pentyl-benzoic Acid Methyl Ester

To a degassed solution of 2-bromo-4-[1,3]dioxin-2-yl-benzoic acid methyl ester (380 mg, 1.3 mmol) in THF (10 mL) are added $PdCl_2(dppf)_2$ (108 mg, 0.13 mmol) and n-pentyl zinc bromide (0.5 M in THF, 8.0 mL, 4.0 mmol). The mixture is heated to 50° C. overnight. After cooling to room temperature, the mixture is partitioned between EtOAc (30 mL) and water (30 mL). The organic phase is washed with brine (30 mL), dried ($Na_2SO_4$), filtered, and concentrated under reduced pressure to a residue. The residue is purified by flash chromatography to afford the title compound as syrup (360 mg, 98%). LC-ES/MS m/e 279.3 (M+1).

Preparation 97

4-Formyl-2-pentyl-benzoic Acid Methyl Ester

To a solution of 4-[1,3]Dioxin-2-yl-2-pentyl-benzoic acid methyl ester (360 mg, 1.3 mmol) in THF (5.0 mL) is added concentrated HCl (0.55 mL, 6.5 mmol). The reaction is stirred for 2.0 h. The reaction mixture is partitioned between EtOAc (20 mL) and water (20 mL). The organic phase is washed with brine (20 mL), dried ($Na_2SO_4$), filtered, and concentrated under reduced pressure to a residue. The residue is purified by flash chromatography to afford the title compound as syrup (236 mg, 98%). LC-ES/MS m/e 235.3 (M+1).

Preparation 98

2-Butyrylamino-4-methyl-benzoic Acid Methyl Ester

To a 0° C. solution of 2-amino-4-methyl-benzoic acid methyl ester (1.5 g, 9.0 mmol) and triethylamine (1.4 g, 13.5 mmol) in methylene chloride (30.0 mL) is added butyryl chloride (1.2 g, 10.8 mmol) dropwise. The mixture is stirred at 0° C. for 30 min and is quenched with saturated sodium bicarbonate (10 mL). The organic phase is washed with brine (20 mL), dried ($Na_2SO_4$), filtered, and concentrated under reduced pressure to a residue. The residue is purified by flash chromatography to afford the title compound as syrup (2.2 g, 100%). LC-ES/MS m/e 236.3 (M+1).

The following compound is prepared essentially according to the preparation of 2-butyrylamino-4-methyl-benzoic acid methyl ester using the appropriate starting material.

Preparation 98A: 4-Methyl-2-(propane-1-sulfonylamino)-benzoic acid methyl ester (3.2 g, 93%), LC-ES/MS m/e 272.3 (M+1), 289.2 (M+18).

Preparation 99

4-Iodo-3-trifluoromethyl-benzoic Acid

To a 0° C. suspension of 4-Amino-3-trifluoromethyl benzoic acid (1.8 g, 8.8 mmol) in conc. HCl (30.0 mL) is added a solution of sodium nitrite (0.76 g, 11.0 mmol) in water (15 mL) dropwise. The mixture is stirred at 0-10° C. for 30 min. A solution of potassium iodide (14.6 g, 88 mmol) in water (25 mL) is added dropwise. The mixture is stirred at room temperature for 1.0 h. The reaction mixture is extracted with EtOAc (80 mL), washed with brine (80 mL), dried ($Na_2SO_4$), filtered, and concentrated under reduced pressure to a residue. The residue is purified by flash chromatography to afford the title compound as solid (2.4 g, 86%). LC-ES/MS: 339.3 (M+23), 315.0 (M−1).

Preparation 100

3-Iodo-5-trifluoromethyl-benzoic Acid

The title compound (3.86 g, 78%) is prepared essentially according to the procedure of 4-iodo-3-trifluoromethyl-benzoic acid using the appropriate starting material. LC-ES/MS m/e 315.0 (M−1).

Preparation 101

5-Butoxy-isophthalic Acid Monomethyl Ester

A suspension of 5-butoxy-isophthalic acid dimethyl ester (2.0 g, 7.5 mmol) in THF/MeOH/water (5.0 mL each) is treated with lithium hydroxide (0.22 g, 9.0 mmol) at room temperature for 1.0 h. The reaction mixture is acidified with 1.0 M HCl and the product is extracted with EtOAc (30 mL), washed with brine (30 mL), dried ($Na_2SO_4$), filtered, and concentrated under reduced pressure to a residue. The residue is purified by flash chromatography to afford the title compound as solid (1.0 g, 53%). LC-ES/MS m/e 270.3 (M+18), 251.3 (M−1).

Preparation 102

(3-Butoxy-5-hydroxymethyl-phenyl)-methanol

A solution of 5-Butoxy-isophthalic acid monomethyl ester (1.0 g, 4.0 mmol) in THF (20 mL) is treated with 2.0 M borane-dimethyl sulfide complex in hexane (10 mL, 20 mmol). The mixture is stirred at room temperature for 48 h. The mixture is quenched carefully with methanol (10 mL) and is concentrated to dryness. The residue is purified by flash chromatography to afford the title compound as a solid (0.78 g, 88%). LC-ES/MS m/e 211.3 (M+1).

Preparation 103

3-Butoxy-5-formyl-benzoic Acid

Step A (3-Butoxy-5-hydroxymethyl-phenyl)-methanol (780 mg, 3.7 mmol) is oxidized to the aldehyde (740 mg, 97%) with the procedure essentially as described in the synthesis of 4-formyl-2-methyl-benzoic acid methyl ester. LC-ES/MS m/e 206.1 (M+1).

Step B

The aldehyde intermediate from step A (740 mg, 3.6 mmol) is dissolved in DMF (5.0 mL) and is treated with oxone (2.2 g, 3.6 mmol) at room temperature for 2.0 h. The reaction is quenched with 10% sodium bisulfite (10 mL) and the product is extracted with EtOAc (40 mL), washed with brine (30 mL), dried ($Na_2SO_4$), filtered, and concentrated under reduced pressure to a residue. The residue is purified by flash chromatography to afford the title compound as white solid which is contaminated with the over-oxidized bis-acid side product (800 mg, 100%). LC-ES/MS m/e 221.3 (M−1).

Preparation 104

(4-Hydroxy-2-methyl)-carbamic Acid Benzyl Ester

To a suspension of 4-amino-3-methyl-phenol (10.8 g, 88 mmol) in THF (80 mL) and saturated sodium bicarbonate (50 mL) is added benzyl chloroformate (18.0 g, 105 mmol) dropwise. The reaction mixture is stirred for 1.0 h. The two phases are separated and the organic phase is concentrated to a residue. The residue is partitioned between EtOAc (100 mL) and 5% HCl (50 mL). The organic phase is washed with brine (100 mL), dried ($Na_2SO_4$), filtered, and concentrated under reduced pressure to a residue. The residue is purified by flash chromatography to afford the title compound as a brown solid (21.0 g, 93%). LC-ES/MS m/e 258.3 (M+1), 256.0 (M−1).

Preparation 105

[4-(tert-Butyl-dimethyl-silanyloxy)-2-methyl-phenyl]-carbamic Acid Benzyl Ester To a solution of (4-hydroxy-2-methyl)-carbamic acid benzyl ester (21.0 g, 81.7 mmol) and imidazole (6.7 g, 98 mmol) in DMF (100 mL) is added a solution of tert-butyldimethylsilyl chloride (14.8 g, 98 mmol) in DMF (20 mL) at 0° C. After the addition, the mixture is stirred at room temperature for 30 min. The solvent is removed under reduced pressure to give a residue, which is partitioned between EtOAc (100 mL) and 5% HCl (50 mL). The organic phase is washed with brine (100 mL), dried ($Na_2SO_4$), filtered, and concentrated under reduced pressure to a residue. The residue is purified by flash chromatography to afford the title compound as yellowish solid (28.8 g, 95%). LC-ES/MS m/e 372.3 (M+1).

Preparation 106

[4-(tert-Butyl-dimethyl-silanyloxy)-2-methyl-phenyl]-methyl-carbamic Acid Benzyl Ester To a solution of [4-(tert-butyl-dimethyl-silanyloxy)-2-methyl-phenyl]-carbamic acid benzyl ester (18 g, 48.5 mmol) in DMF (100 mL) is added sodium hydride (60% dispersion in oil, 2.3 g, 58 mmol) in portions at 0° C. The mixture is stirred at room temperature for 30 min, followed by the addition of iodomethane (8.2 g, 58 mmol). The mixture is stirred at room temperature overnight. The solvent is removed under reduced pressure to give a residue, which is partitioned between EtOAc (100 mL) and water (100 mL). The organic phase is washed with brine (100 mL), dried ($Na_2SO_4$), filtered, and concentrated under reduced pressure to a residue. The residue is purified by flash chromatography to afford the title compound as oil (14.0 g, 75%). LC-ES/MS m/e 386.0 (M+1).

Preparation 107

[4-(tert-Butyl-dimethyl-silanyloxy)-2-methyl-phenyl]-methyl-amine

The mixture of [4-(tert-butyl-dimethyl-silanyloxy)-2-methyl-phenyl]-methyl-carbamic acid benzyl ester (14.0 g, 36.0 mmol) and palladium on carbon (10 wt %, 0.5 g) in methanol (100.0 mL) is stirred under an atmosphere of hydrogen at room temperature overnight. The reaction mixture is filtered and the filtrate is concentrated under reduced pressure to a residue. The residue is purified by flash chromatography to afford the title compound as oil (7.4 g, 81%). LC-ES/MS m/e 252.3 (M+1).

Preparation 108

4-({[4-(tert-Butyl-dimethyl-silanyloxy)-2-methyl-phenyl]-methyl-amino}-methyl)-2-methyl-benzoic Acid Methyl Ester A mixture of [4-(tert-butyl-dimethyl-silanyloxy)-2-methyl-phenyl]-methyl-amine (643 mg, 2.6 mmol, 1.2 eq) and 4-formyl-2-methyl-benzoic acid methyl ester (380 mg, 2.1 mmol), acetic acid (252 mg, 4.2 mmol, 2.0 eq.), sodium triacetoxyborohydride (890 mg, 4.2 mmol, 2.0 eq.) in 1,2-dichloroethane is stirred at room temperature overnight. The mixture is concentrated under reduced pressure and the resulting residue is partitioned between EtOAc (50 mL) and 5% NaHCO3 (40 mL). The organic. phase is washed with brine (50 mL), dried (Na₂SO₄), filtered, and concentrated under reduced pressure to a residue. The residue is purified by flash chromatography eluting with a gradient of EtOAc/Hexane to afford the title compound as a syrup (1.0 g, 95%). LC-ES/MS m/e 414.3 (M+1).

Preparation 109

2-Butoxy-4-({[4-(tert-butyl-dimethyl-silanyloxy)-2-methyl-phenyl]-methyl-amino}-methyl)-benzoic Acid Methyl Ester The title compound is prepared essentially according to the preparation of 4-({[4-(tert-butyl-dimethyl-silanyloxy)-2-methyl-phenyl]-methyl-amino}-methyl)-2-methyl-benzoic acid methyl ester starting from [4-(tert-butyl-dimethyl-silanyloxy)-2-methyl-phenyl]-methyl-amine and 2-butoxy-4-formyl-benzoic acid methyl ester. The title compound is obtained as syrup after workup and is used without further purification. LC-ES/MS m/e 472.3 (M+1).

Preparation 110

4-{[(4-Hydroxy-2-methyl-phenyl)-methyl-amino]-methyl}-2-methyl-benzoic Acid Methyl Ester To a solution of 4-({[4-(tert-butyl-dimethyl-silanyloxy)-2-methyl-phenyl]-methyl-amino}-methyl)-2-methyl-benzoic acid methyl ester (1.0 g, 2.1 mmol) in THF (20.0 mL) is added 1.0 M TBAF/THF (3.2 mL, 3.2 mmol) at room temperature. The reaction mixture is stirred for 1.0 h. The mixture is partitioned between EtOAc (30 mL) and water (30 mL). The organic phase is washed with brine (30 mL), dried (Na₂SO₄), filtered, and concentrated under reduced pressure to a residue. The residue is purified by flash chromatography to afford the title compound as oil (0.45 g, 62%). LC-ES/MS m/e 300.3 (M+1), 298.3 (M−1).

Preparation 111

2-Butoxy-4-{[(4-hydroxy-2-methyl-phenyl)-methyl-amino]-methyl}-benzoic Acid Methyl Ester The title compound (200 mg, 55%) is prepared essentially according to the preparation of 4-{[(4-hydroxy-2-methyl-phenyl)-methyl-amino]-methyl}-2-methyl-benzoic acid methyl ester using the appropriate starting material. LC-ES/MS m/e 358.3 (M+1).

Preparation 112

6-Bromo-benzo[d]isothiazole-3-carboxylic Acid

The title compound is prepared essentially according to WO 2005/092890 Procedure 3 using the appropriate starting material. ES/MS m/e 255.0 (M−1).

Preparation 113

6-(4-Hydroxy-2-methyl-phenyl)-benzo[d]isothiazole-3-carboxylic Acid

To a degassed solution of 6-Bromo-benzo[d]isothiazole-3-carboxylic acid (0.42 g, 1.54 mmol), 3-Methyl-4-(4,4,5,5-tetramethyl-[1,3,2]dioxaborolan-2-yl-phenol (0.54, 2.31 mmol), 2-Dicyclohexylphosphino-2',6'-dimethoxy-1,1'-biphenyl (0.064 g, 0.154 mmol), and potassium phosphate (0.71 g, 3.1 mmol) in dioxane (8 mL) and water (4 mL) is added Pd(OAc)₂ (6.5 mg, 0.03 mmol). The reaction is degassed again and heated to 80 degrees for 18 h. The reaction is cooled to room temperature and concentrated. The residue is diluted with EtOAc and 1N HCl. The layers are separated and concentrated. The crude material is diluted with 20 mL of MeOH and 2 mL H₂SO₄ and heated to reflux for 2 h. The reaction mixture is concentrated onto silica and purified by flash chromatography (20-50% EtOAc in Hexanes) to yield the title compound (0.12 g, 26%). ES/MS m/e 300.0 (M+1).

The following compound is prepared essentially according to the preparation of 6-(4-Hydroxy-2-methyl-phenyl)-benzo[d]isothiazole-3-carboxylic acid using the appropriate starting material Preparation 113A: 6-(4-Hydroxy-2-methyl-phenyl)-1-methyl-1H-indazole-3-carboxylic acid (0.53 g, 75%), ES/MS m/e 297.0 (M+1).

Preparation 114

6-Bromo-1H-indazole-3-carboxylic Acid Methyl Ester

The title compound is prepared essentially according to WO 2005/092890 Procedure 4 using the appropriate starting material. ES/MS m/e 254.0 (M+1).

Preparation 115

6-Bromo-1methyl-1H-indazole-3-carboxylic Acid Methyl Ester

The title compound is prepared essentially according to WO 2005/080389 Procedure 1d using the appropriate starting material. ES/MS m/e 268.0 (M+1).

Preparation 116

Benzo[b]thiophene-5-carboxylic Acid Ethyl Ester

A saturated solution of HCl in ethanol (15 mL) is added to benzothiophene-5-carboxylic acid (1 g, 5.44 mmol) and stirred at 80° C. overnight. The solvent is removed under reduced pressure. Diethyl ether and saturated sodium bicarbonate are added. The aqueous layer is discarded. The organic layer is washed with saturated sodium bicarbonate and water, dried (Na₂SO₄), filtered, and concentrated under reduced pressure to yield the title compound as a pale brown oil (1.0 g, 89%). ¹H NMR (CDCl₃): δ 8.54 (s, 1H), 8.01 (d, 1H, J=8.1 Hz), 7.92 (d, 1H, J=8.1 Hz), 7.51 (d, 1H, J=5.4 Hz), 7.42 (d, 1H, J=5.4 Hz), 4.42 (c, 2H, J=6.8 Hz), 1.43 (t, 3H, J=6.8 Hz).

Preparation 117

2-(4-Methoxy-2-methyl-phenyl)-benzo[b]thiophene-5-carboxylic Acid Ethyl Ester

Cesium carbonate (9.70 mmol; 3.19 g) is dried in a resealable tube at 150° C. in vacuo for 2 h and cooled to room temperature. Copper(I) iodide (9.70 mmol; 1.86 g), Pd(OAc)₂ (0.24 mmol; 55 mg), triphenylphosphine (0.485 mmol; 128.50 mg), 2-bromo-5-methoxytoluene (9.70 mmol; 2.14 mL), benzo[b]thiophene-5-carboxylic acid ethyl ester (4.85 mmol; 1 g) and anhydrous DMF (24 mL) are added under nitrogen atmosphere and the mixture is stirred at 140° C. After 24 h, Pd(OAc)$_2$ (0.24 mmol; 55 mg) and triphenylphosphine (0.485 mmol; 128.50 mg) are added and the mixture is stirred for 24 more hours. The mixture is allowed to reach room temperature and water and ethyl acetate are added. The suspension is filtered through Celite® and washed with ethyl acetate. The organic layer is separated and the aqueous layer is extracted with ethyl acetate. The organic layers are combined, washed with water, dried (Na$_2$SO$_4$), filtered and concentrated under reduced pressure. The residue is chromatographed (0-10% EtOAc in hexanes) to obtain the title compound (960 mg, 61%) as a colorless waxy solid. LC-ES/MS m/e 326 (M).

Preparation 118

2-(4-Hydroxy-2-methyl-phenyl)-benzo[b]thiophene-5-carboxylic Acid Ethyl Ester

A 0° C. solution of boron tribromide (1M in dichloromethane, 1.29 mmol; 1.29 mL) is added under nitrogen atmosphere to a solution of 2-(4-methoxy-2-methyl-phenyl)-benzo[b]thiophene-5-carboxylic acid ethyl ester (1.07 mmol; 350 mg) in anhydrous dichloromethane (4.00 mL) and the mixture is stirred at room temperature for 4 h. Water and ethyl acetate are added. The aqueous layer is separated and the organic layer is dried (Na$_2$SO$_4$), filtered, and concentrated under reduced pressure. The residue is dissolved in ethanol (5 mL) and acetyl chloride (3.48 mmol, 0.25 mL) is added. The mixture is stirred at reflux for 5 h. The solvent is removed and the residue is chromatographed (5-20% EtOAc in hexanes) to yield the title compound (145 mg, 40%) as a white solid. LC-ES/MS m/e 313 (M+1).

Preparation 119

Benzo[b]thiophene-7-carboxylic Acid

A solution of 7-bromobenzothiophene (9.38 mmol; 2 g) in 10 mL of anhydrous THF is added slowly to a suspension of activated magnesium (14.08 mmol; 345.6 mg) in 2 mL of anhydrous THF at 65° C. and stirred for 1 h under a nitrogen atmosphere. The mixture is allowed to reach room temperature and a stream of carbon dioxide is bubbled into the mixture for 5 minutes. After 1 h, 1N HCl is added until the mixture reaches pH 1. The aqueous layer is extracted with ethyl acetate. The organic layers are combined, dried (Na$_2$SO$_4$), filtered, and concentrated under reduced pressure. Petroleum ether is added and the resulting solid is collected by filtration to obtain the title compound (1.05 g, 63%) as a white solid. $^1$H NMR (CDCl$_3$): δ 8.26 (d, 1H, J=6.5 Hz), 8.10 (dd, 1H, J=7.3 Hz, 1 Hz), 7.61 (d, 1H, J=5.6 Hz), 7.51 (t, 1H, J=7.3 Hz), 7.44 (d, 1H, J=5.6 Hz).

Preparation 120

Benzo[b]thiophene-7-carboxylic Acid Ethyl Ester

Acetyl chloride (14.8 mmol; 1.05 mL) is added to a solution of benzo[b]thiophene-7-carboxylic acid (4.94 mmol; 880 mg) in ethanol (20 mL) and the mixture is stirred at reflux for 24 h. The solvent is removed. Ethyl acetate is added to the residue and the resulting solution is washed with water, dried (Na$_2$SO$_4$), filtered and concentrated to obtain the title compound (880 mg, 92%) as colorless oil. $^1$H NMR (CDCl$_3$): δ 8.12 (dd, 1H, J=7.2 Hz, 0.6 Hz), 8.03 (dd, 1H, J=7.6 Hz, 1.2 Hz), 7.58 (d, 1H, J=5.6 Hz), 7.46 (t, 1H, J=7.6 Hz), 7.41 (t, 1H, J=5.2 Hz), 4.50 (c, 2H, J=7.3 Hz), 1.47 (t, 3H, J=7.3 Hz).

Preparation 121

2-(4,4,5,5-Tetramethyl-[1,3,2]dioxaborolan-2-yl)-benzo[b]thiophene-7-carboxylic Acid Ethyl Ester In a resealable tube are placed bis(pinacolato)diboron (433.17 μmol; 110.00 mg), di-mu-chlorobis((1,2,5,6-eta)-1,5-cyclooctadiene)diiridium (6.50 μmoles; 4.41 mg), 4,4'-di-tert-butyl-2,2'-dipyridyl (13.00 μmoles; 3.49 mg). The tube is purged with nitrogen followed by anhydrous octane (2.60 mL). Benzo[b]thiophene-7-carboxylic acid ethyl ester (1.73 mmoles; 357.39 mg) is added. The mixture is stirred at 90° C. for 16 h. Diethyl ether is added to mixture and it is washed with HCl (1M) and water. The organic layer is dried (Na$_2$SO$_4$), filtered, and concentrated. Hexane is added. The resulting solid is filtered off and the solvent is removed to obtain 470 mg of a 1:1 mixture of starting material and desired compound. The mixture is used in the next step without further purification. LC-ES/MS m/e 333 (M+1).

Preparation 122

2-(4-Hydroxy-2-methyl-phenyl)-benzo[b]thiophene-7-carboxylic Acid Ethyl Ester

A solution of 2-(4,4,5,5-tetramethyl-[1,3,2]dioxaborolan-2-yl)-benzo[b]thiophene-7-carboxylic acid ethyl ester (1.04 mmoles; 345.00 mg) in anhydrous DMF (2.5 mL) is added, under nitrogen atmosphere, via syringe pump (3 mL/2 h) to a suspension at 80° C. of 4-bromo-3-methylphenol (1.04 mmoles; 194.23 mg), Cesium carbonate (2.08 mmoles; 683.53 mg), Pd(OAc)$_2$ (103.84 μmoles; 23.55 mg), 1,1'-bis(diphenylphosphino)ferrocene (311 μmoles; 176 mg) in anhydrous DMF (1.6 mL). The mixture is stirred at 80° C. for 1 h and allowed to reach room temperature. The reaction is poured into a mixture of ethyl acetate and HCl (1M), filtered through Celite® and washed with ethyl acetate. The organic layer is separated and the aqueous layer is extracted with ethyl acetate (2×20 mL). The organic layers are combined, washed with water, dried (Na$_2$SO$_4$), filtered and concentrated. The residue is chromatographed (10-40% EtOAc in hexanes) to obtain the title compound (143 mg, 44%) as a white solid. LC-ES/MS m/e 311 (M−1).

Preparation 123

3-Fluoro-4'-hydroxy-2'-methyl-biphenyl-4-carboxylic Acid Methyl Ester

A solution of 3-methyl-4-(4,4,5,5-tetramethyl-[1,3,2]dioxaborolan-2-yl)-phenol (0.241 g, 1.03 mmol) and 4-bromo-2-fluoro-benzoic acid methyl ester (0.240 g, 1.03 mmol) in 1,4-dioxane (20 mL) is evacuated and re-filled with N$_2$ 3 times. To this solution, Pd(PPh$_3$)$_4$ (0.010 g) and aqueous Na$_2$CO$_3$ (1.0 mL, 2.0 M) are added. The resulting mixture is heated at 90° C. for 24 hours under N$_2$. The reaction mixture is cooled to room temperature and neutralized with HCl (1.0 M, 3.0 mL) and concentrated. The residue is extracted with ethyl acetate (30 mL×2), and the combined organic layers are dried over sodium sulfate and concentrated. The residue is purified via silica gel chromatography eluting with 25-30% ethyl acetate in hexanes to give the title compound (0.211 g, 79%). $^1$H NMR (400 MHz, CDCl$_3$): δ 7.95-7.91 (t, 1H), 7.10-7.04 (m, 3H), 6.74-6.69 (m, 2H), 3.93 (s, 3H), 2.21 (s, 3H).

The following list of compounds is prepared essentially as described in the preparation of 3-Fluoro-4'-hydroxy-2'-methyl-biphenyl-4-carboxylic acid methyl ester using the appropriate starting material.

Preparation 123A: 3,5-Difluoro-4'-hydroxy-2'-methyl-biphenyl-4-carboxylic acid methyl ester (0.230 g, 77%), $^1$H NMR (400 MHz, CDCl$_3$): δ 7.18-7.16 (d, 1H), 6.88 (s, 1H), 6.86 (s, 1H), 6.73 (s 1H), 6.71-6.68 (dd, 1H), 3.95 (s, 3H), 2.22 (s, 3H).

Preparation 124

3-methyl-4'-hydroxy-2'-methyl-biphenyl-4-carboxylic Acid Methyl Ester

Step A

A solution of 4-bromo-2-methyl-benzoic acid (1.08 g, 5.02 mmol) in methanol (20 mL) is treated with H$_2$SO$_4$ (0.20 mL). The mixture is stirred at 80° C. for 16 hours and cooled to room temperature. The mixture is neutralized with aqueous Na$_2$CO$_3$ and concentrated, the residue is extracted with ethyl acetate (30 mL×2) and the combined organic layers are dried over sodium sulfate and concentrated to provide 4-bromo-2-methyl-benzoic acid methyl ester (1.25 g, 97%). $^1$H NMR (400 MHz, CDCl$_3$): δ 7.78 (d, 1H), 7.40 (s, 1H), 7.35 (d, 1H), 3.82 (s, 3H), 2.57 (s, 3H).

Step B

A solution of 3-methyl-4-(4,4,5,5-tetramethyl-[1,3,2]dioxaborolan-2-yl)-phenol (0.241 g, 1.03 mmol) and 4-bromo-2-methyl-benzoic acid methyl ester (0.236 g, 1.03 mmol) in 1,4-dioxane (20 mL) is evacuated and re-filled with N$_2$ 3 times. To this solution, Pd(PPh$_3$)$_4$ (0.010 g) and aqueous Na$_2$CO$_3$ (1.0 mL, 2.0 M) are added. The resulting mixture is heated at 90° C. for 24 hours under N$_2$. The reaction mixture is cooled to room temperature, neutralized with HCl (1.0 M, 3.0 mL), and concentrated. The residue is extracted with ethyl acetate (30 mL×2) and the combined organic layers are dried over sodium sulfate and concentrated. The residue is purified via silica gel chromatography eluting with 25-30% ethyl acetate in hexanes to give the title compound (0.199 g, 75%). $^1$H NMR (400 MHz, CDCl$_3$): δ 7.95-7.91 (d, 1H), 7.18 (s, 1H), 7.18 (d, 1H), 7.08 (d, 1H), 6.75 (d, 1H), 6.72 (d, 1H), 3.90 (s, 3H), 2.61 (s, 3H).

The following list of compounds is prepared essentially as described in the preparation of 3-methyl-4'-hydroxy-2'-methyl-biphenyl-4-carboxylic acid methyl ester using the appropriate starting material.

Preparation 124A: 3-Chloro-4'-hydroxy-2'-methyl-biphenyl-4-carboxylic acid methyl ester (0.089 g, 63%), $^1$H NMR (400 MHz, CDCl$_3$): δ 7.86-7.83 (d, 1H), 7.37 (s, 1H), 7.23-7.20 (d, 1H), 7.06-7.04 (d, 1H), 6.74 (s, 1H), 6.72-6.70 (d, 1H), 3.94 (s, 3H), 2.20 (s, 3H).

Preparation 125

3-Butoxy-4'-hydroxy-2'-methyl-biphenyl-4-carbaldehyde

Step A

A solution of 4-bromo-2-hydroxy-benzonitrile (0.89 g, 4.45 mmol) in THF (50 mL) and 1-butanol (2.0 mL) is slowly added to NaH (0.356 g, 8.90 mmol). The mixture is stirred at room temperature for one hour and quenched with water (10 mL). The mixture is concentrated, and the residue is extracted with ethyl acetate (20 mL×2). The combined organic layers are dried over sodium sulfate and concentrated to provide 4-bromo-2-butoxy-benzonitrile (0.65 g, 57%). $^1$H NMR (400 MHz, CDCl$_3$): δ 7.37-7.34 (d, 1H), 7.11-7.08 (d, 1H), 7.08 (s, 1H), 4.04-4.01 (t, 2H), 1.80 (tt, 2H), 1.50 (tt, 2H), 0.95 (t, 3H).

Step B

A solution of 4-bromo-2-butoxy-benzonitrile (0.58 g, 2.28 mmol) in toluene (20 mL) at −78° C. is added DIBAH (1.0 M, 4.56 mL). The mixture is stirred overnight and allowed to warm to room temperature. The reaction is quenched with MeOH (5 mL), and the mixture is poured into NH$_4$Cl (aq., 30 mL). The mixture is stirred for 5 minutes, treated with H$_2$SO$_4$ (10%, 10 mL), and stirred for 10 minutes. The mixture is extracted with ethyl acetate (30 mL×2), and the combined organic layers are dried over sodium sulfate and concentrated to provide 4-bromo-2-butoxy-benzaldehyde (0.41 g, 70%). ES/MS m/e 257.0; 259.0 (M+1).

Step C

A solution of 3-methyl-4-(4,4,5,5-tetramethyl-[1,3,2]dioxaborolan-2-yl)-phenol (0.210 g, 0.898 mmol) and 4-bromo-2-butoxy-benzaldehyde (0.210 g, 0.817 mmol) in 1,4-dioxane (20 mL) is evacuated and re-filled with N$_2$ 3 times. To this solution, Pd(PPh$_3$)$_4$ (0.010 g) and aqueous Na$_2$CO$_3$ (1.0 mL, 2.0 M) are added. The resulting mixture is heated at 90° C. for 24 hours under N$_2$. The reaction mixture is cooled to room temperature, neutralized with HCl (1.0 M, 3.0 mL), and concentrated. The residue is extracted with ethyl acetate (30 mL×2), and the combined organic layers are dried over sodium sulfate and concentrated. The residue is purified via silica gel chromatography eluting with 25-30% ethyl acetate in hexanes to give the title compound (0.198 g, 85%). ES/MS m/e 283.0 (M−1).

Preparation 126

6-(4-Hydroxy-2-methyl-phenyl)-benzo[d]isoxazole-3-carboxylic Acid Ethyl Ester

Step A

A solution of (4-bromo-2-nitro-phenyl)-acetic acid (5.00 g, 19.2 mmol) in methanol (100 mL) is treated with conc. HCl (1.0 mL). The mixture is stirred at 85° C. for 16 hours and cooled to room temperature. The mixture is neutralized with aqueous Na$_2$CO$_3$ and concentrated. The residue is extracted with ethyl acetate (50 mL×2), and the combined organic layers are dried over sodium sulfate and concentrated to provide (4-bromo-2-nitro-phenyl)-acetic acid methyl ester as a brown solid (5.27 g, 100%).

Step B

A solution of (4-bromo-2-nitro-phenyl)-acetic acid methyl ester (0.99 g, 3.61 mmol) in ethanol (8 mL) at room temperature is treated with isoamyl nitrite (0.60 mL, 4.47 mmol). A solution of NaOEt in ethanol (1.9 M, 2.0 ml) is added, and the mixture is stirred at 60° C. for 2 hours and at room temperature for 16 hours. The mixture is neutralized with HCl (1.0 M, 4.0 mL) and concentrated. The residue is extracted with ethyl acetate (20 mL×2) and the combined organic layers are dried over sodium sulfate and concentrated. The residue is purified via silica gel chromatography eluting with 25% ethyl acetate in hexanes to give 6-bromo-benzo[d]isoxazole-3-carboxylic acid ethyl ester (0.36 g, 37%). ES/MS m/e 269.8; 271.8 (M+1).

Step C

A solution of 3-methyl-4-(4,4,5,5-tetramethyl-[1,3,2]dioxaborolan-2-yl)-phenol (0.624 g, 2.67 mmol) and 6-bromo-benzo[d]isoxazole-3-carboxylic acid ethyl ester (0.360 g, 1.33 mmol) in 1,4-dioxane (20 mL) is evacuated and re-filled with $N_2$ 3 times. To this solution, $Pd_2(dba)_3$ (0.010 g), tricyclohexyl phosphine (PCy3, 10 mg), and aqueous $K_3PO_4$ (1.5 mL, 1.30 M) are added. The resulting mixture is heated at 50° C. for 2 hours under $N_2$. The reaction mixture is cooled to room temperature and filtered through a pad of celite. The filtrate is concentrated, and the residue is purified via silica gel chromatography eluting with 25% ethyl acetate in hexanes to give the title compound (0.366 g, 93%). ES/MS m/e 298.0 (M+1); 296.0 (M−1).

Preparation 127

2-Methyl-6-(4,4,5,5-tetramethyl-[1,3,2]dioxaborolan-2-yl)-benzofuran-3-carboxylic Acid Methyl Ester Step A A solution of 2-iodo-5-methoxy-phenol (39 g, 156 mmol) in dimethylformamide (300 mL) and N,N,N',N'-tetramethylguanidine (150 mL) is treated with copper(I) Iodide (1.89 g, 9.82 mmol) and bis(triphenylphosphine)palladium(II) chloride (1.9 g; 2.71 mmol; 1.900 g). The mixture is cooled to −78° C., and propyne (100 g; 2.50 moles) is bubbled through the mixture for 1 hour. The reaction mixture is stirred and allowed to warm to room temperature gradually over 6 hours. After stirred for 2 days, the reaction mixture is quenched with water (800 mL) and extracted with EtOAc (500 mL). The organic layers is dried over $Na_2SO_4$, filtered and concentrated. The crude product is purified by flash chromatography (eluted with 10% EtOAc/Hexanes) and the appropriate fractions are concentrated. The material is dried in vacuo to afford 6-methoxy-2-methyl-benzofuran (17.5 g, 69%). $^1$H NMR (400 MHz, $CDCl_3$): δ 7.31-7.29 (d, 1H), 6.95 (s, 1H), 6.81-6.79 (d, 1H), 6.26 (s, 1H), 3.81 (s, 3H), 2.40 (s, 3H).

Step B

A solution of 6-methoxy-2-methyl-benzofuran (17.4 g, 107 mmol) in dichloromethane (200 mL) at 0° C. is treated with boron tribromide (1.0 M, 107 mL). The mixture is stirred at 0° C. for 60 minutes and quenched with water (50 mL). The organic layer is dried over $Na_2SO_4$, filtered, and concentrated. The crude product is purified by flash chromatography eluted with 25% EtOAc/Hexanes, and the appropriate fractions are concentrated. The material is dissolved in dichloromethane (150 mL) and triethylamine (17.0 mL, 122 mmol) at 0° C. is treated with acetic acid anhydride (7.22 mL, 76.35 mmol). The reaction is stirred for 16 hours and allowed to warm to room temperature. The reaction is quenched with MeOH (10 mL) and concentrated. The residue is purified by silica gel chromatography with 25% EtOAc/Hexanes to provide acetic acid 2-methyl-benzofuran-6-yl ester (9.50 g, 82%). $^1$H NMR (400 MHz, $CDCl_3$): δ 7.40-7.38 (d, 1H), 7.15 (s, 1H), 6.91-6.88 (d, 1H), 6.32 (s, 1H), 2.41 (s, 3H), 2.29 (s, 3H).

Step C

To a slurry of aluminum trichloride (20.0 g, 150 mmol) in dichloromethane (200 mL) is added oxalyl chloride (13.0 mL, 150 mmol) and the mixture is stirred at 0° C. for 30 minutes. A solution of acetic acid 2-methyl-benzofuran-6-yl ester (9.50 g; 49.9 mmol) in dichloromethane (50 mL) is added over 10 minutes. The ice-bath is removed and the reaction is stirred at room temperature for 2 hours. The reaction mixture is cooled to 0° C. and quenched with MeOH (50 mL). The mixture is concentrated to a residue, dissolved in methanol (250 mL), and treated with potassium carbonate (8.28 g, 59.9 mmol). The mixture is stirred at room temperature for 16 hours, filtered through a pad of celite, and concentrated. The residue is diluted with water (100 mL) and extracted with EtOAc (250 mL×2). The combined organic layers are dried over $Na_2SO_4$, filtered, and concentrated. The crude product is purified by flash chromatography (eluted with 25% EtOAc/Hexanes), and the appropriate fractions are concentrated. The material is dried in vacuo to afford 6-hydroxy-2-methyl-benzofuran-3-carboxylic acid (9.56 g, 93%). ES/MS m/e 207.0 (M+1); 205.0 (M−1).

Step D

A solution of 6-hydroxy-2-methyl-benzofuran-3-carboxylic acid methyl ester (9.5 g, 46.07 mmol) in dichloromethane (100 mL) and triethylamine (12.8 mL, 92.14 mmol) at 0° C. is treated with trifluoromethanesulfonic anhydride (8.54 L, 50.68 mmol). The reaction mixture is stirred at 0° C. for 60 minutes and quenched with MeOH (10 mL). The mixture is concentrated to a residue, which is purified by silica gel chromatography with 20% EtOAc/Hexanes to provide the 2-methyl-6-trifluoromethanesulfonyloxy-benzofuran-3-carboxylic acid methyl ester (14.1 g, 90%). $^1$H NMR (400 MHz, $CDCl_3$): δ 7.99-7.96 (d, 1H), 7.37 (s, 1H), 7.21-7.18 (d, 1H), 3.93 (s, 3H), 2.76 (s, 3H).

Step E

A solution of 2-methyl-6-trifluoromethanesulfonyloxy-benzofuran-3-carboxylic acid methyl ester (3.25 g, 9.61 mmol) and bis(pinacolato)diboron (3.05 g, 12.0 mmol) in acetonitrile (50 mL) is de-gassed by vacuum/re-fill nitrogen three times. Tricyclohexylphosphine (108 mg, 0.384 mmol) and $Pd(OAc)_2$ (43 mg, 0.192 mmol) and cesium fluoride (2.92 g, 19.2 mmol) are added, and the mixture is heated at 85° C. for 16 hours. The reaction mixture is cooled to room temperature and filtered through a pad of Celite®. The filtrate is concentrated to a residue, which is purified by silica gel chromatography with 15% EtOAc/Hexanes to provide 2-methyl-6-(4,4,5,5-tetramethyl-[1,3,2]dioxaborolan-2-yl)-benzofuran-3-carboxylic acid methyl ester (1.96 g, 65%). ES/MS m/e 317.0 (M+1).

Preparation 128

[6-(4,4,5,5-Tetramethyl-[1,3,2]dioxaborolan-2-yl)-benzo[b]thiophen-3-yl]-acetic Acid Methyl Ester Step A To a solution of 3-methoxy-benzenethiol (5.75 g, 41.0 mmol) and potassium carbonate (11.45 g, 82.02 mmol) in acetonitrile (150 mL) is added butanoic acid, 4-chloro-3-oxo-, ethyl ester (6.12 mL, 45.11 mmol) at 0° C. The mixture is stirred at room temperature for 2 hours and filtered through a pad of Celite®. The filtrate is concentrated and purified by silica gel chromatography with 25-30% EtOAc/Hexanes to provide 4-(3-methoxy-phenylsulfanyl)-3-oxo-butyric acid ethyl ester (10.9 g, 99%) ES/MS m/e 267.0 (M−1).

Step B 4-(3-methoxy-phenylsulfanyl)-3-oxo-butyric acid ethyl ester (10.9 g, 40.62 mmol) is added to methanesulfonic acid (26.6 mL, 406 mmol), and the mixture is stirred at room temperature for 30 minutes. The mixture is poured into ice-water (300 g) and extracted with EtOAc (100 mL×2). The combined organic layers are dried over $Na_2SO_4$, filtered, and concentrated. The crude product is purified by flash chromatography (eluted with 20% EtOAc/Hexanes), and the appropriate fractions are concentrated. The material is dried in vacuo to afford 4-methoxy-benzo[b]thiophen-3-yl)-acetic acid ethyl ester (6.00 g, 59%). ES/MS m/e 251.0 (M+1)

Step C

A solution of (6-methoxy-benzo[b]thiophen-3-yl)-acetic acid ethyl ester (3.81 g, 15.22 mmol) in dichloromethane (50 mL) at −78° C. is added boron tribromide (38.1 mL, 38.1 mmol) dropwise. The mixture is stirred and allowed to warm to room temperature overnight. The mixture is cooled to 0° C. and quenched with water (100 mL). The organic layer is separated, and the aqueous layer is extracted with EtOAc (50 mL). The combined organic layers are dried over $Na_2SO_4$, filtered, and concentrated. The crude product is purified by flash chromatography eluting with 30-40% EtOAc/Hexanes. The appropriate fractions are pooled and concentrated under reduced pressure. The material is dried in vacuo to afford (6-hydroxy-benzo[b]thiophen-3-yl)-acetic acid ethyl ester (3.35 g, 93%). ES/MS m/e 237.0 (M+1); 235.0 (M−1).

Step D

To a solution of (6-hydroxy-benzo[b]thiophen-3-yl)-acetic acid ethyl ester (3.31 g, 14.0 mmol) in dichloromethane (50 mL) at −78° C. are added triethylamine (3.90 mL, 28.0 mmol) and trifluoromethanesulfonic anhydride (2.60 mL, 15.4 mmol). The mixture is stirred and allowed to warm to room temperature for 30 minutes. The reaction is quenched with MeOH (5.0 mL) and concentrated under reduced pressure. The residue is purified by silica gel chromatography with 20% EtOAc/Hexanes to provide (6-trifluoromethanesulfonyloxy-benzo[b]thiophen-3-yl)-acetic acid ethyl ester (5.05 g, 98%). ES/MS m/e 366.8 (M−1).

Step E

A solution of (6-trifluoromethanesulfonyloxy-benzo[b]thiophen-3-yl)-acetic acid ethyl ester (2.21 g, 6.00 mmol) and bis(pinacolato)diboron (1.90 g, 7.50 mmol) in acetonitrile (25 mL) is evacuated and refilled with $N_2$ three times. $Pd(OAc)_2$ (27 mg, 0.12 mmol), tricyclohexylphosphine (67 mg, 0.24 mmol), and cesium fluoride (1.82 g, 12.00 mmol) are added. The mixture is stirred at 95° C. for 1 hour and quenched with water (5 mL). The mixture is filtered through a pad of Celite®, and the filtrate is concentrated under reduced pressure. The residue is extracted with EtOAc (20 mL×2). The combined organic layers are dried over $Na_2SO_4$, filtered, and concentrated under reduced pressure. The crude product is purified by flash chromatography eluting with 20% EtOAc/Hexanes. The appropriate fractions are pooled and concentrated under reduced pressure. The material is dried in vacuo to afford [6-(4,4,5,5-tetramethyl-[1,3,2]dioxaborolan-2-yl)-benzo[b]thiophen-3-yl]-acetic acid ethyl ester (1.56 g, 75%). ES/MS m/e (M+18): 364.0; (M+1):347.0

Preparation 129

Trifluoro-methanesulfonic Acid 2-benzoyl-4-methyl-phenyl Ester

Triethylamine (3.56 g, 35 mmol) is added to a solution of (2-Hydroxy-5-methyl-phenyl)-phenyl-methanone (5.0 g, 23.5 mmol) in dichloromethane (40 mL). The mixture is cooled to 0° C. and trifluoromethane sulfonic anhydride (7.97 g, 28.2 mmol) is added dropwise. The mixture is stirred at 0° C. for 1.0 h, quenched with sat. $NaHCO_3$ (20 mL), diluted with dichloromethane (30 mL). The layers are separated and the organic layer is washed with water (30 mL) and brine (30 mL), dried ($Na_2SO_4$), and concentrated in vacuo. The residue is purified via column chromatography ($SiO_2$, gradient EtOAc/Hex) to give the title compound (8.18 g, 100%) as an oil. LC-ES/MS: 345.0 (M+1), 362.0 (M+18).

Preparation 130

(3-Fluoro-4-nitro-phenoxy)-triisopropyl-silane

A mixture of 3-fluoro-4-nitro-phenol (4.94 g, 31.4 mmol), triisopropylsilyl chloride (6.40 mL, 29.9 mmol), and imidazole (4.85 g, 70.7 mmol) in 70 mL of dichloromethane is stirred for 1.5 hours. Dichloromethane (100 mL) is added and the mixture is washed with water and brine, dried ($MgSO_4$), and concentrated under reduced pressure. The residue is purified on silica gel (120 g) eluting with a gradient of ethyl acetate in heptane (0 to 80%) to provide the title compound (8.55 g, 87%) as an oil. ES/MS m/e 314.3.0 (M+1).

Preparation 131

2-Fluoro-4-triisopropylsilanyloxy-phenylamine

A flask with a mixture of (3-fluoro-4-nitro-phenoxy)-triisopropyl-silane (6.74 g, 21.5 mmol) in ethyl acetate (200 mL) is evacuated and filled with nitrogen three times. Palladium 10% by weight on carbon (550 mg) is added. The flask is evacuated and filled with nitrogen three times and then it is evacuated and filled with hydrogen from a balloon. The mixture is stirred under hydrogen atmosphere (balloon) over night. The mixture is filtered over diatomaceoud earth and concentrated to provide the title compound (6.2 g, 100%) as an oil. LC-ES/MS m/e 284.2 (M+1).

The following compound is prepared essentially according to the preparation of 2-fluoro-4-triisopropylsilanyloxy-phenylamine utilizing the appropriate starting material.

Preparation 131A: 4-Amino-3-fluoro-phenol (1.7 g, 96%), $^1$H NMR (400 MHz, DMF-$d_7$) δ 8.75 (s, 1H), 6.78 (m, 1H), 6.40 (m, 1H), 6.50 (m, 1H), 4.38 (s, 2H).

Preparation 132

(2-Fluoro-4-triisopropylsilanyloxy-phenyl)-carbamic Acid Tert-butyl Ester

A mixture of 2-fluoro-4-triisopropylsilanyloxy-phenylamine (6.2 g, 21.9 mmol) and di-t-butyldicarbonate (4.65 g, 20.7 mmol) in THF (100 mL) is stirred over night at 75° C. The mixture is concentrated under reduced pressure and purified on silica (120 g) eluting with 100% dichloromethane to provide 6.5 g of oil. The oil is purified on silica (120 g) eluting with a gradient of dichloromethane in heptane (10% to 70%) to provide the title compound (6.1 g, 73%) as a colorless oil. MS (ES) m/z 383.3.0 (M−1).

Preparation 133

(2-Fluoro-6-methyl-4-triisopropylsilanyloxy-phenyl)-methyl-amine

To a solution of (2-fluoro-4-triisopropylsilanyloxy-phenyl)-carbamic acid tert-butyl ester (5.64 g, 14.7 mmol) in tetrahydrofuran (100 mL) at −78° C. is added tert-butyllithium (17.5 mL, 29.8 mmol). After one hour, methyl iodide (1.83 mL, 29.4 mmol) is added. Additional tert-butyllithium (17.5 mL, 29.8 mmol) is added followed by additional methyl iodide (1.83 mL, 29.4 mmol). The mixture is then allowed to slowly warm to room temperature over night. Aqueous saturated ammonium chloride is added and the layers are separated. The organic layer is dried (MgSO$_4$) and concentrated to a mixture of oil and solids. The crude is partitioned between dichloromethane and water. The aqueous layer is extracted with dichloromethane (3×). The combined dichloromethane layers are dried (MgSO$_4$) and concentrated. The resulting residue is purified on 120 g silica with 100% dichloromethane to provide 3.8 g of oil. The oil is treated with cold 4M HCl in dioxane solution. After one hour, the mixture is concentrated and partitioned between ethyl acetate and saturated aqueous sodium bicarbonate. The aqueous layer is extracted with ethyl acetate (2×). The combined ethyl acetate layers are dried (MgSO$_4$) and concentrated. The residue is purified on 120 g silica with 10% ethyl acetate in heptane (3×) to provide 350 mg (7.6%) of the title compound as an oil. LC-ES/MS m/e 312.2 (M+1).

Preparation 134

4-{[(2-Fluoro-6-methyl-4-triisopropylsilanyloxy-phenyl)-methyl-amino]-methyl}-2-methyl-benzoic Acid Methyl Ester A mixture of (2-fluoro-6-methyl-4-triisopropylsilanyloxy-phenyl)-methyl-amine (326 mg, 1.05 mmol) and 4-formyl-2-methyl-benzoic acid methyl ester (320 mg, 1.80 mmol) in 4 mL acetic acid is stirred for 2.5 hours at room temperature. Sodium triacetoxyborohydride (773 mg, 3.65 mmol) is added and stirred. Upon completion of the reaction, the mixture is concentrated and partitioned between ethyl acetate and saturated aqueous sodium bicarbonate. The aqueous layer is extracted with ethyl acetate (3×). The combined ethyl acetate layers are dried (MgSO$_4$) and concentrated. The residue is purified on 40 g silica with ethyl acetate in heptane gradient (10% to 20%) to provide 457 mg (92%) of the titled compound as an oil. MS (ES) m/z 475.3 (M+1).

The following list of compounds are prepared essentially according to the preparation of 4-{[(2-fluoro-6-methyl-4-triisopropylsilanyloxy-phenyl)-methyl-amino]-methyl}-2-methyl-benzoic acid methyl ester utilizing the appropriate starting materials.

Preparation 134A: 4-[(2-Fluoro-4-hydroxy-phenylamino)-methyl]-2-methyl-benzoic acid methyl ester (1.9 g, 93%), starting from 4-amino-3-fluoro-phenol (900 mg, 7.08 mmol) and 4-formyl-2-methyl-benzoic acid methyl ester (1.23 g, 6.90 mmol), MS (ES) m/z 290.0 (M+1); Preparation 134B: 4-[(4-Hydroxy-phenylamino)-methyl]-2-methyl-benzoic acid methyl ester (2.10 g, 80%), starting from 4-amino-phenol (1.06 g, 9.71 mmol) and 4-formyl-2-methyl-benzoic acid methyl ester (1.92 g, 10.8 mmol), LC-ES/MS m/e 272.2 (M+1); Preparation 134C: 4-[(2-Chloro-4-hydroxy-phenylamino)-methyl]-2-methyl-benzoic acid methyl ester (420 mg, 41%), starting from 4-amino-3-chloro-phenol hydrochloride (665 mg, 3.69 mmol) and 4-formyl-2-methyl-benzoic acid methyl ester (595 mg, 3.34 mmol) to provide the title compound as a solid. LC-ES/MS m/e 306.2 (M+1).

Preparation 135

4-{[(2-Fluoro-4-hydroxy-6-methyl-phenyl)-methyl-amino]-methyl}-2-methyl-benzoic Acid Methyl Ester A mixture of 4-{[(2-fluoro-6-methyl-4-triisopropylsilanyloxy-phenyl)-methyl-amino]-methyl}-2-methyl-benzoic acid methyl ester (457 mg, 0.965 mmol) and tetrabutylammonium fluoride (2.0 mL of 1M in THF, 2.0 mmol) in THF (10 mL) is stirred at 0° C. for 20 minutes and then 2.0 mL of 1M HCl is added and the mixture is concentrated. The residue is portioned between ethyl acetate and brine. The layers are separated and the brine layer is extracted with ethyl acetate. The combined ethyl acetate layers are dried (MgSO$_4$) and concentrated. The residue is purified on 40 g silica with ethyl acetate in heptane gradient (10% to 70%) to provide 233 mg (76%) of the titled compound as a glass. LC-ES/MS m/e 318.2 (M+1).

Preparation 136

4-{[(2-Fluoro-4-hydroxy-phenyl)-methyl-amino]-methyl}-2-methyl-benzoic Acid Methyl Ester A mixture of 4-[(2-fluoro-4-hydroxy-phenylamino)-methyl]-2-methyl-benzoic acid methyl ester (1.89 g, 6.53 mmol) and 2.0 mL of 37% formaldehyde in 20 mL of acetic acid is stirred for 40 minutes. Sodium triacetoxyborohydride (2.80 g, 13.2 mmol) is added. Upon completion, the mixture is concentrated and partitioned between ethyl acetate and saturated aqueous sodium bicarbonate. The aqueous layer is extracted with ethyl acetate (3×). The combined ethyl acetate layers are dried (MgSO$_4$) and concentrated. The residue is purified on 120 g silica with ethyl acetate in heptane gradient (10% to 60%) to provide 1.0 g (51%) of the titled compound as a white solid. LC-ES/MS m/e 304.0 (M+1).

The following list of compounds are prepared essentially according to the preparation of 4-{[(2-fluoro-4-hydroxy-phenyl)-methyl-amino]-methyl}-2-methyl-benzoic acid methyl ester using the appropriate starting material.

Preparation 136A: 4-{[(4-Hydroxy-phenyl)-methyl-amino]-methyl}-2-methyl-benzoic acid methyl ester (120 mg, 52%), starting from 4-[(4-hydroxy-phenylamino)-methyl]-2-methyl-benzoic acid methyl ester (220 mg, 0.855 mmol), 4-formyl-2-methyl-benzoic acid methyl ester (1.92 g, 10.8 mmol), and 0.5 mL of 37% formaldehyde, LC-ES/MS m/e 272.2 (M+1); Preparation 136B: 4-{[(2-Chloro-4-hydroxy-phenyl)-methyl-amino]-methyl}-2-methyl-benzoic acid methyl ester (250 mg, 61%), starting from 4-[(2-Chloro-4-hydroxy-phenylamino)-methyl]-2-methyl-benzoic acid methyl ester (390 mg, 1.28 mmol) and 0.5 mL of 37% formaldehyde, LC-ES/MS m/e 320.2 (M+1).

Preparation 137

6-Bromo-benzo[d]isothiazole-3-carboxylic Acid

The title compound is prepared essentially according to Procedure 3 in WO 2005/092890. ES/MS m/e 255.0 (M−1).

Preparation 138

6-(4-Hydroxy-2-methyl-phenyl)-benzo[d]isothiazole-3-carboxylic Acid

To a degassed solution of 6-bromo-benzo[d]isothiazole-3-carboxylic acid (0.42 g, 1.54 mmol), 3-Methyl-4-(4,4,5,5-tetramethyl-[1,3,2]dioxaborolan-2-yl-phenol (0.54, 2.31 mmol), 2-Dicyclohexylphosphino-2',6'-dimethoxy-1,1'-biphenyl (0.064 g, 0.154 mmol), and potassium phosphate (0.71 g, 3.1 mmol) in dioxane (8 mL) and water (4 mL) is added Pd(OAc)$_2$ (6.5 mg, 0.03 mmol). The reaction is degassed again and heated to 80° C. for 18 h. The reaction is cooled to room temperature and concentrated under reduced pressure. The material is diluted with EtOAc and 1N HCl. The layers are separated and concentrated under reduced pressure. The crude material is diluted with 20 mL of MeOH and 2 mL H$_2$SO$_4$ and heated to reflux for 2 h. The reaction is concentrated onto silica and purified using a gradient of 20 to 50% EtOAc in Hexanes to yield the title compound (0.12 g, 26% yield). ES/MS m/e 300.0 (M+1).

Preparation 139

6-Bromo-1-methyl-1H-indole-3-carboxylic Acid Methyl Ester

A mixture of 5-bromo-1H-indole-3-carboxylic acid methyl ester (100 mg, 0.394 mmol), potassium carbonate (163 mg, 1.18 mmol) and DMF is stirred at room temperature. Iodomethane (30 μL, 0.47 mmol) is added. After 1.5 hours, additional iodomethane (10 μL) is added and the reaction is stirred for 30 minutes and diluted with dichloromethane and filtered. The filtrate is concentrated under high vacuum, diluted with ethyl acetate and concentrated to give 105 mg (99%) of the title compound.

MS m/z: 270.0 (M+2).

The following compound is prepared essentially according to the preparation of 6-bromo-1-methyl-1H-indole-3-carboxylic acid methyl ester utilizing the appropriate starting material.

Preparation 139A: 6-Bromo-1-isopropyl-1H-indole-3-carboxylic acid methyl ester, starting from 6-bromo-1H-indole-3-carboxylic acid methyl ester and isopropyl bromide, $^1$H NMR (400 MHz, CDCl$_3$) δ 8.02 (d, 1H), 7.88 (s, 1H), 7.52 (s, 1H), 7.33 (d, 1H), 4.60 (m, 1H), 3.88 (s, 3H), 1.55 (d, 6H).

Preparation 140

6-(4-Hydroxy-2-methyl-phenyl)-1-methyl-1H-indole-3-carboxylic Acid Methyl Ester

A mixture of 3-methyl-4-(4,4,5,5-tetramethyl-[1,3,2]dioxaborolan-2-yl)-phenol (2.36 g, 10.1 mmol), 6-bromo-1H-indole-3-carboxylic acid methyl ester (1.8 g, 6.71 mmol), tetrakis(triphenylphosphine)palladium(0) (300 mg, 0.26 mmol), DMF (27 mL), ethanol (13.5 mL) and 2M aqueous potassium carbonate (13.5 mL) is heated to 85° C. for 4 hours. The reaction is cooled to room temperature and diluted with water and acidified with 1 N HCl. The resulting solution is extracted with ethyl acetate. The combined organic layers are washed with brine and dried over anhydrous magnesium sulfate and concentrated. The residue is purified with flash chromatography eluting with 25→40% ethyl acetate/heptane to give 1.73 mg (87%) of the title compound.

The following compound is prepared essentially according to the preparation of 6-(4-hydroxy-2-methyl-phenyl)-1-methyl-1H-indole-3-carboxylic acid methyl ester using the appropriate starting material.

Preparation 140A: 6-(4-Hydroxy-phenyl)-1-isopropyl-1H-indole-3-carboxylic acid methyl ester, starting from 6-bromo-1-isopropyl-1H-indole-3-carboxylic acid methyl ester, ES/MS m/e 324.1 (M+1).

Preparation 141

2-(4-Chloro-2-nitro-phenyl)-3-hydroxy-but-2-enoic Acid Methyl Ester

A mixture of sodium hydride (60% in mineral oil, 2.6 g, 65 mmol) and DMF (52 mL) is stirred in an ice bath and methylacetoacetate (6.46 mL, 60 mmol) is added over ten minutes via syringe. The mixture is stirred in the ice bath for 10 minutes, stirred at ambient temperature for 20 minutes, and finally cannulated over five minutes into cold, (ice bath) neat 2-chloro-5-fluoronitrobenzene (5.00 g, 28.5 mmol). The ice bath is removed after 40 minutes and the mixture is allowed to stir overnight at ambient temperature. The mixture is acidified with 2N HCl, and diluted with water and ether. The ether layer is dried over MgSO$_4$ and concentrated to provide 6.52 g (84%) of the title compound. MS m/e 270.0 (M−1).

Preparation 142

6-Chloro-2-methyl-1H-indole-3-carboxylic Acid Methyl Ester

A mixture of 2-(4-chloro-2-nitro-phenyl)-3-hydroxy-but-2-enoic acid methyl ester (4.66 g, 17.2 mmol), iron (5.76 g, 103 mmol) and glacial acetic acid (16 mL) is heated at 115° C. for 1 h and allowed to cool. The reaction mixture is diluted with water and ethyl acetate. The ethyl acetate layer is washed with brine and dried over MgSO$_4$. The mixture of the title compound and a small amount of impurity is used in the next reaction without additional purification. ES/MS m/e 224.0 (M+1).

Preparation 143

6-Chloro-1,2-dimethyl-1H-indole-3-carboxylic Acid Methyl Ester

A mixture of 6-chloro-2-methyl-1H-indole-3-carboxylic acid methyl ester (2.76 g, 12.3 mmol), potassium carbonate (6.80 g, 49.2 mmol), iodomethane (1.07 mL, 17.2 mmol) and DMF (36 mL) is stirred overnight at room temperature. The mixture is diluted with ethyl acetate, washed twice with water, washed with brine and dried (MgSO$_4$) and concentrated. The residue is triturated in 25 mL of 1:3 ethyl acetate-heptane and filtered to provide 1.63 g (55%) of pure title product. Additional material can be obtained through further trituration of the mother liquor. ES/MS m/e 238.0 (M+1).

Preparation 144

6-(4-Hydroxy-2-methyl-phenyl)-1,2-dimethyl-1H-indole-3-carboxylic Acid Methyl Ester A flask containing a mixture of 6-chloro-1,2-dimethyl-1H-indole-3-carboxylic acid methyl ester (1.60 g, 6.73 mmol), 3-methyl-4-(4,4,5,5-tetramethyl-[1,3,2]dioxaborolan-2-yl)-phenol (3.15 g, 13.5 mmol), aqueous tribasic potassium phosphate (1.27 M, 9.0 mL, 11 mmol), tricyclohexylphosphine (53 mg, 0.19 mmol) and tris(dibenzylideneacetone)dipalladium (0) (73 mg, 0.080 mmol) and dioxane (22 mL) is evacuated and filled with nitrogen several times. The reaction mixture is heated to 100° C. for 18 h. The mixture is allowed to cool and is filtered thru celite, washing with ethyl acetate. The filtrate is concentrated and partitioned with 1 N HCl and ethyl acetate. The ethyl acetate layer is washed with brine, dried over $MgSO_4$ and concentrated. The residue is triturated in THF-heptane to provide 1.83 g (88%) of the title compound as a white solid. MS m/e 310.0 (M+1).

Preparation 145

2- and 3-acetyl-6-bromobenzothiophene

To a solution of 6-bromobenzothiophene (20 g, 93.8 mmol) and acetyl chloride (8.84 g, 112.6 mmol) in 1,2-dichloroethane (120 mL) is added dropwise at room temperature, tin tetrachloride (1M in dichloromethane, 112.6 mmol, 112.6 mL) under nitrogen. After the addition is completed, the reaction mixture is stirred at room temperature overnight. The mixture is poured onto an ice/water bath and extracted with dichloromethane. The organic phase is washed with sat. $NaHCO_3$, water and brine, dried over $MgSO_4$ and evaporated. The crude residue is purified by flash chromatography on silica gel eluting with hexane/EtOAc 6:1 as eluent mixture. The title compound (12 g, 50%) is obtained as a 7:3 mixture of the two isomers: 3-acetyl-6-bromobenzothiophene and 2-acetyl-6-bromobenzothiophene. ES/MS m/e 256 (M+2).

Preparation 146

6-Bromobenzothiophene-3-carboxylic Acid and 6-Bromobenzothiophene-2-carboxylic Acid To a 0° C. solution of sodium hydroxide (13.64 g, 341 mmol) in water (94 mL) is added slowly bromine (21.92 g, 137.18 mmol). The reaction mixture is stirred at 0° C. for 15 minutes. To the reaction mixture is added dropwise a solution of the mixture of 3-acetyl-6-bromobenzothiophene and 2-acetyl-6-bromobenzothiophene (10.00 g, 39.19 mmol) in dioxane (75 mL). The reaction mixture is stirred at room temperature for 2 hours. After 2 h, 50 mL of a $NaHSO_3$ (40%) solution is added followed by 10 mL of HCl to give an orange solid. The solid is filtered off, and washed with water followed by hexanes to give 7 g (70%) of the mixture of both acids: 6-Bromobenzothiophene-3-carboxylic acid and 6-Bromobenzothiophene-2-carboxylic acid in a ratio 7:3. ES/MS m/e 258 (M+2).

Preparation 147

6-Bromobenzothiophene-3-carboxylic Acid Methyl Ester and 6-Bromobenzothiophene-2-carboxylic Acid Methyl Ester A solution of the mixture of 6-Bromobenzothiophene-3-carboxylic acid and 6-Bromobenzothiophene-2-carboxylic acid (6.5 g, 25.28 mmol) and sulfuric acid (4.65 g, 47.43 mmol) in MeOH (100 mL) is heated to 65° C. overnight. A light brown solid is visualized. The solution is cooled to room temperature and the solid formed is filtered off and washed with MeOH to give 5.6 g (83%) of the mixture of: 6-Bromobenzothiophene-3-carboxylic acid methyl ester and 6-Bromobenzothiophene-2-carboxylic acid methyl ester in a ratio 7:3. ES/MS m/e 272 (M+2).

Preparation 148

6-(4-Hydroxy-2-methyl-phenyl)-benzo[b]thiophene-3-carboxylic Acid Methyl Ester; Compound with 6-(4-hydroxy-2-methyl-phenyl)-benzo[b]thiophene-2-carboxylic Acid Methyl Ester The title compound is prepared essentially according to the preparation of 6-(4-hydroxy-2-methyl-phenyl)-1-methyl-1H-indole-3-carboxylic acid methyl ester, utilizing a 7:3 mixture of 6-bromo-benzo[b]thiophene-3-carboxylic acid methyl ester and 6-bromo-benzo[b]thiophene-2-carboxylic acid methyl ester. ES/MS m/e 297.0 (M−1).

Preparation 149

2-Isopropoxy-4-methyl-benzoic Acid Methyl Ester

Disopropyl azodicarboxylate (8.7 mL, 44 mmol) is added to a stirred solution of methyl 2-hydroxy-4-methylbenzoate (4.85 g, 29.2 mmol), isopropanol (3.3 mL, 44 mmol), triphenylphosphene (11.5 g, 43.8 mmol) and THF (50 mL) at room temperature. The exothermic reaction is cooled in an ice bath and is allowed to stir overnight at room temperature. The mixture is diluted with ethyl acetate and water, and the organic phase is washed with brine and dried over $MgSO_4$. The crude residue is purified by flash chromatography (20 to 40% EtOAc/heptane) to afford the title compound (4.95 g, 81%) as an oil. ES/MS m/e 209.3 (M+1).

Preparation 150

4-Bromomethyl-2-isopropoxy-benzoic Acid Methyl Ester

A mixture of 2-isopropoxy-4-methyl-benzoic acid methyl ester (1.00 g, 4.8 mmol), N-bromosuccinimide (0.940 g, 5.28 mmol), 2,2'-azo-bis-isobutyronitrile (50 mg, 0.30 mmol) and carbon tetrachloride (20 mL) is stirred under a bright lamp for 3 h. The mixture is concentrated and the residue is purified via flash chromatography (0 to 50% EtOAc-heptane) to provide the title compound (0.85 g, 62%) as an orange oil. ES/MS m/e 288.7 (M+1).

The following compound is prepared essentially according to the preparation of 4-bromomethyl-2-isopropoxy-benzoic acid methyl ester using the appropriate starting material.

Preparation 150A: 4-Bromomethyl-2-methoxy-benzoic acid methyl ester, starting from 2-isopropoxy-4-methyl-benzoic acid methyl ester and methanol, MS m/z: 261.0 (M+2).

Preparation 151

(4-Hydroxy-2-methyl-phenyl)-carbamic Acid Tert-butyl Ester

Di-tert-butyl dicarbonate (21.3 g, 97.4 mmol) is added to a solution of 4-amino-m-cresol (10.0 g, 81.2 mmol), triethylamine (13.6 mL, 97.4 mmol) and methylene chloride (150 mL) at room temperature and the contents are stirred for 2 h. The mixture is washed with saturated aqueous citric acid and brine, and is dried over anhydrous sodium sulfate. The crude product is purified by flash chromatography (20 to 40% EtOAc/heptane) to afford the title compound (5.9 g, 33%) as a white solid. ES/MS m/e 222.0 (M−1).

Preparation 152

{4-[4-Cyclopropyl-2-(2-trifluoromethoxy-phenyl)-2H-pyrazol-3-ylmethoxy]-2-methyl-phenyl}-carbamic Acid Tert-butyl Ester Tri-n-butylphosphine (1.9 mL, 7.5 mmol) and azodicarboxylic acid dipiperidine (1.90 g, 7.54 mmol) are added to a mixture of [4-cyclopropyl-2-(2-trifluoromethoxy-phenyl)-2H-pyrazol-3-yl]-methanol (1.50 g, 5.03 mmol), (4-hydroxy-2-methyl-phenyl)-carbamic acid tert-butyl ester (1.35 g, 6.03 mmol) and toluene at room temperature. After 1 h, additional tri-n-butylphosphine (0.6 mL) is added and the mixture is stirred for 2 h. The mixture is concentrated and the residue is purified by flash chromatography (20 to 50% EtOAc/heptane) to give the title compound (1.92 g, 76%). LC-ES/MS m/e 504.2 (M+1).

Preparation 153

{4-[4-Cyclopropyl-2-(2-trifluoromethoxy-phenyl)-2H-pyrazol-3-ylmethoxy]-2-methyl-phenyl}-methyl-carbamic Acid Tert-butyl Ester Sodium hydride (60% in mineral oil, 183 mg, 4.58 mmol) is added to a solution of {4-[4-cyclopropyl-2-(2-trifluoromethoxy-phenyl)-2H-pyrazol-3-ylmethoxy]-2-methyl-phenyl}-carbamic acid tert-butyl ester (1.92 g, 3.81 mmol) and DMF (15 mL) in an ice bath. The mixture is stirred for 30 minutes and iodomethane (0.36 mL, 5.7 mmol) is added. The bath is removed and the mixture is stirred for 1 h and quenched with a mixture if ice and ammonium chloride. The mixture is diluted with ethyl acetate and water. The organic layer is washed with brine and dried over MgSO$_4$ to provide 1.94 g (98%) of the title compound as an oil. LC-ES/MS m/e 518.2 (M+1).

Preparation 154

{4-[4-Cyclopropyl-2-(2-trifluoromethoxy-phenyl)-2H-pyrazol-3-ylmethoxy]-2-methyl-phenyl}-methyl-amine HCl/dioxane (4 N, 3.7 mL) is added to a solution of {4-[4-cyclopropyl-2-(2-trifluoromethoxy-phenyl)-2H-pyrazol-3-ylmethoxy]-2-methyl-phenyl}-methyl-carbamic acid tert-butyl ester (1.92 g, 3.71 mmol) in methylene chloride (40 mL) at room temperature. After 2 h of stirring, the mixture is concentrated and worked up with ethyl acetate and saturated aqueous sodium bicarbonate. The organic layers are washed with brine and dried over sodium sulfate to provide 1.50 g (97%) of the title compound as an oil. MS m/e 418.0 (M+1).

Preparation 155

4-Formyl-3-formylamino-benzoic Acid Methyl Ester

Methyl indole-6-carboxylate (1.0 g, 5.7 mmol) is dissolved in methanol (50 mL) and is cooled to −78° C. Ozone is bubbled through until the starting material fully consumed. Dimethyl sulfide (4.0 mL) and chloroform (25 mL) are added and the reaction mixture is stirred overnight at room temperature. The solvents are removed in vacuo and the crude product is recrystallized from chloroform to give pure product (0.57 g, 48%).

EXAMPLES

Example 1

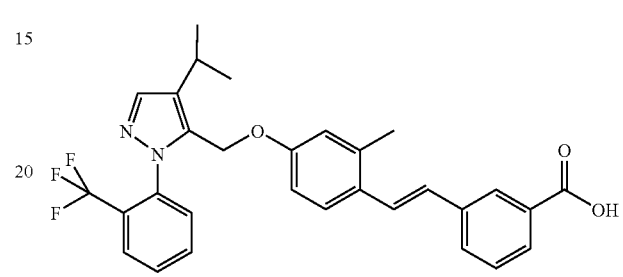

Step A 3-(2-{4-[4-Isopropyl-2-(2-trifluoromethyl-phenyl)-2H-pyrazol-3-ylmethoxy]-2-methyl-phenyl}-vinyl)-benzoic Acid Methyl Ester To a suspension of 3-[2-(4-hydroxy-2-methyl-phenyl)-vinyl]-benzoic acid methyl ester (107 mg, 0.4 mmol) and potassium carbonate (138 mg, 1 mmol) in CH$_3$CN (4 mL) is added 5-bromomethyl-4-isopropyl-1-(2-trifluoromethyl-phenyl)-1H-pyrazole in CH$_3$CN (4 mL, approximately 0.1 mmol/mL). The reaction mixture is stirred at 80° C. for 5 hours and filtered through a Celite® pad eluting with EtOAc. The combined filtrate is concentrated and purified by column chromatography (0 to 20% EtOAc in hexanes) to give the desired product, 136 mg (64%).

LC-ES/MS m/e 535 (M+1).

Step B 3-(2-{4-[4-Isopropyl-2-(2-trifluoromethyl-phenyl)-2H-pyrazol-3-ylmethoxy]-2-methyl-phenyl}-vinyl)-benzoic Acid To a solution of 3-(2-{4-[4-isopropyl-2-(2-trifluoromethyl-phenyl)-2H-pyrazol-3-ylmethoxy]-2-methyl-phenyl}-vinyl)-benzoic acid methyl ester (136 mg, 0.25 mmol) in 1,4-dioxane (7 mL) is added 2N LiOH/H$_2$O (3 mL). The reaction mixture is stirred at 50° C. overnight. The solvent is evaporated and the residue is partitioned between EtOAc and 1N HCl. The layers are separated and the organic phase is washed with water and concentrated to give the title compound (129 mg, 97%). LC-ES-MS m/e 521 (M+1), 100%.

The compounds listed in table 1 are prepared essentially according to the preparation of 3-(2-{4-[4-Isopropyl-2-(2-trifluoromethyl-phenyl)-2H-pyrazol-3-ylmethoxy]-2-methyl-phenyl}-vinyl)-benzoic acid methyl ester using the appropriate starting material.

TABLE 1

| Ex | Chemical Name | Physical Data |
|---|---|---|
| 2 | 4'-[2-(2,6-Dichloro-phenyl)-4-isopropyl-2H-pyrazol-3-ylmethoxy]-2,2'-dimethyl-biphenyl-4-carboxylic acid | LC-MS: 509 (M + 1), |
| 3 | 5-{4-[2-(2,6-Dichloro-phenyl)-4-isopropyl-2H-pyrazol-3-ylmethoxy]-2-methyl-phenyl}-4-methyl-thiophene-2-carboxylic acid | LC-MS: 515 (M + 1), |
| 4 | 5-{4-[2-(2,6-Dichloro-phenyl)-4-isopropyl-2H-pyrazol-3-ylmethoxy]-2-methyl-phenyl}-thiophene-2-carboxylic acid | LC-MS: 501 (M + 1), |
| 5 | 2-{4-[2-(2,6-Dichloro-phenyl)-4-isopropyl-2H-pyrazol-3-ylmethoxy]-2-methyl-phenyl}-4-methyl-thiazole-5-carboxylic acid | LC-MS: 516 (M + 1 |
| 6 | 5-{4-[4-Isopropyl-2-(2-trifluoromethoxy-phenyl)-2H-pyrazol-3-ylmethoxy]-2-methyl-phenyl}-thiophene-2-carboxylic acid | LC-MS: 517 (M + 1), |
| 7 | 2-{4-[4-Isopropyl-2-(2-trifluoromethoxy-phenyl)-2H-pyrazol-3-ylmethoxy]-2-methyl-phenyl}-4-methyl-thiazole-5-carboxylic acid | LC-MS: 532 (M + 1), |
| 8 | 5-{4-[2-(2,6-Dichloro-phenyl)-4-isopropyl-2H-pyrazol-3-ylmethoxy]-phenyl}-thiophene-2-carboxylic acid | LC-MS: 487 (M + 1), |
| 9 | 2-{4-[2-(2,6-Dichloro-phenyl)-4-isopropyl-2H-pyrazol-3-ylmethoxy]-phenyl}-4-methyl-thiazole-5-carboxylic acid | LC-MS: 502 (M + 1 |
| 10 | 4'-[4-Isopropyl-2-(2-trifluoromethyl-phenyl)-2H-pyrazol-3-ylmethoxy]-2'-methyl-biphenyl-4-carboxylic acid | LC-MS: 495 (M + 1 |
| 11 | 4'-[2-(2,6-Dichloro-phenyl)-5-methyl-4-propyl-2H-pyrazol-3-ylmethoxy]-2'-methyl-biphenyl-4-carboxylic acid | LC/MS (ES+): 509.0 |
| 12 | 4'-[2-(2,6-Dichloro-phenyl)-4,5-dimethyl-2H-pyrazol-3-ylmethoxy]-2'-methyl-biphenyl-4-carboxylic acid | LC/MS (ES+): 481.0 |
| 13 | 4'-[2-(2,6-Dichloro-phenyl)-4-isopropyl-2H-pyrazol-3-ylmethoxy]-3-fluoro-2'-methyl-biphenyl-4-carboxylic acid | LC-ES/MS m/e 514.8 (M + 1), 512.8 (M − 1) |
| 14 | 4'-[2-(2,6-Dichloro-phenyl)-4-isopropyl-2H-pyrazol-3-ylmethoxy]-3-methyl-2'-methyl-biphenyl-4-carboxylic acid | LC-ES/MS m/e 510.8 (M + 1), 509.0 (M − 1) |
| 15 | 4'-[2-(2,6-Dichloro-phenyl)-4-isopropyl-2H-pyrazol-3-ylmethoxy]-3,5-difluoro-2'-methyl-biphenyl-4-carboxylic acid | LC-ES/MS m/e 532.8 (M + 1) |
| 16 | 4'-[2-(2,6-Dichloro-phenyl)-4-isopropyl-2H-pyrazol-3-ylmethoxy]-3-chloro-2'-methyl-biphenyl-4-carboxylic acid | LC-ES/MS m/e 531.0 (M + 1) |
| 17 | 6-{4-[2-(2,6-Dichloro-phenyl)-4-isopropyl-2H-pyrazol-3-ylmethoxy]-2-methyl-phenyl}-benzo[d]isoxazole-3-carboxylic acid | LC-ES/MS m/e 536.0; 538.0 (M + 1) |

Example 18

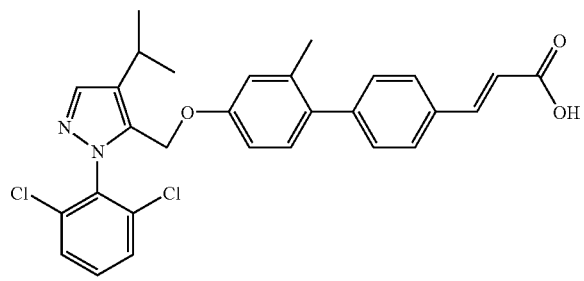

Step A

3-{4'-[2-(2,6-Dichloro-phenyl)-4-isopropyl-2H-pyrazol-3-ylmethoxy]-2'-methyl-biphenyl-4-yl}-acrylic Acid Ethyl Ester To a mixture of (108 mg, 0.403 mmol) 3-(4'-hydroxy-2'-methyl-biphenyl-4-yl)-acrylic acid methyl ester, [2-(2,6-dichloro-phenyl)-4-isopropyl-2H-pyrazol-3-yl]-methanol (126 mg, 0.443 mmol) and toluene (2.1 mL) is added 1,1'-(azodicarbonyl)dipiperidine (112 mg, 0.443 mmol) followed by tri-n-butylphosphine (109 µL, 0.443 mmol). The reaction is kept overnight at room temperature. The reaction mixture is diluted with hexane and the solid is filtered. The concentrated filtrate is purified via flash chromatography eluting with 15% ethyl acetate/heptane) to give 183 mg (85%) of the ester.

Step B

3-{4'-[2-(2,6-Dichloro-phenyl)-4-isopropyl-2H-pyrazol-3-ylmethoxy]-2'-methyl-biphenyl-4-yl}-acrylic Acid A mixture of 3-{4'-[2-(2,6-dichloro-phenyl)-4-isopropyl-2H-pyrazol-3-ylmethoxy]-2'-methyl-biphenyl-4-yl}-acrylic acid methyl ester (510 mg, 0.928 mmol), 5 N sodium hydroxide (928 µL, 4.64 mmol), methanol (15 mL) and THF (12 mL) is stirred overnight at room temperature. The reaction mixture is diluted with water and most of the THF and methanol is evaporated. The remaining aqueous portion is washed with ether and the ether layer is discarded. The aqueous layer is acidified with 1 N HCl and extracted with ether. The combined ether layers are washed with brine, dried over anhydrous magnesium sulfate, and concentrated. The residue is purified using flash chromatography with 5% MeOH/CH$_2$Cl$_2$ and triturated in ether-hexane to give 146 mg (30%) of the title compound. ES/MS m/e ($^{35}$Cl) 521.3 (M+1)

The compounds listed in table 2 are prepared essentially according to the preparation of 3-{4'-[2-(2,6-Dichloro-phenyl)-4-isopropyl-2H-pyrazol-3-ylmethoxy]-2'-methyl-biphenyl-4-yl}-acrylic acid ethyl ester using the appropriate starting material.

TABLE 2

| Ex | Chemical Name | Physical Data |
|---|---|---|
| 19 | 4'-[2-(2,6-Dichloro-phenyl)-4-isobutyl-5-methyl-2H-pyrazol-3-ylmethoxy]-2'-methyl-biphenyl-4-carboxylic acid | LC-ES/MS m/e 523 (M + 1) |
| 20 | 4'-[2-(2,6-Dichloro-phenyl)-4-isopropyl-2H-pyrazol-3-ylmethoxy]-2'-methyl-biphenyl-3-carboxylic acid | LC-MS: 493.3 (M − 1). |
| 21 | 6-{4-[2-(2,6-Dichloro-phenyl)-4-isopropyl-2H-pyrazol-3-ylmethoxy]-2-methyl-phenyl}-nicotinic acid | LC-MS: 496 (M + 1), |
| 22 | 4'-[2-(2,6-Dichloro-phenyl)-4-methyl-2H-pyrazol-3-ylmethoxy]-2'-methyl-biphenyl-4-carboxylic acid | LC-MS: 467 (M + 1), |
| 23 | 4'-[2-(2,6-Difluoro-phenyl)-4-isopropyl-2H-pyrazol-3-ylmethoxy]-2'-methyl-biphenyl-4-carboxylic acid | LC/MS (ES+): 463.3, |
| 24 | 4'-[2-(2,6-Dichloro-phenyl)-4-ethyl-5-methyl-2H-pyrazol-3-ylmethoxy]-2'-methyl-biphenyl-4-carboxylic acid | LC/MS (ES+): 495.0 |
| 25 | 3-[({4-[2-(2,6-Dichloro-phenyl)-4-isobutyl-5-methyl-2H-pyrazol-3-ylmethoxy]-2-methyl-phenyl}-methyl-amino)-methyl]-benzoic acid | LC-ES/MS m/e 544 (M + 1). |
| 26 | 4-[({4-[4-Isopropyl-2-(2-trifluoromethoxy-phenyl)-2H-pyrazol-3-ylmethoxy]-2-methyl-phenyl}-methyl-amino)-methyl]-benzoic acid | LC-MS: 552.0 (M − 1). |
| 27 | 4-[({4-[2-(2,6-Dichloro-phenyl)-4-isopropyl-2H-pyrazol-3-ylmethoxy]-2-methyl-phenyl}-methyl-amino)-methyl]-benzoic acid | LC-MS: 538 (M + 1), |
| 28 | 3-[({4-[2-(2,6-Dichloro-phenyl)-4-isopropyl-2H-pyrazol-3-ylmethoxy]-2-methyl-phenyl}-methyl-amino)-methyl]-benzoic acid | LC-MS: 538 (M + 1), |
| 29 | 3-[({4-[2-(2,6-Dichloro-phenyl)-4-methyl-2H-pyrazol-3-ylmethoxy]-2-methyl-phenyl}-methyl-amino)-methyl]-benzoic acid | LC-MS: 510 (M + 1), |
| 30 | 4-[({4-[2-(2,6-Dichloro-phenyl)-4-methyl-2H-pyrazol-3-ylmethoxy]-2-methyl-phenyl}-methyl-amino)-methyl]-benzoic acid | LC-MS: 510 (M + 1), |
| 31 | 3-[({4-[4-Isopropyl-2-(2-trifluoromethyl-phenyl)-2H-pyrazol-3-ylmethoxy]-2-methyl-phenyl}-methyl-amino)-methyl]-benzoic acid | LC-MS: 538 (M + 1), |
| 32 | 4-[({4-[4-Isopropyl-2-(2-trifluoromethyl-phenyl)-2H-pyrazol-3-ylmethoxy]-2-methyl-phenyl}-methyl-amino)-methyl]-benzoic acid | LC-MS: 538 (M + 1), |
| 33 | 3-[({4-[4-Isopropyl-2-(2-trifluoromethoxy-phenyl)-2H-pyrazol-3-ylmethoxy]-2-methyl-phenyl}-methyl-amino)-methyl]-benzoic acid | LC-MS: 554 (M + 1), |
| 34 | 3-[({4-[2-(2,6-Difluoro-phenyl)-4-isopropyl-2H-pyrazol-3-ylmethoxy]-2-methyl-phenyl}-methyl-amino)-methyl]-benzoic acid | LC/MS (ES+): 506.2 |
| 35 | 4-[({4-[2-(2,6-Difluoro-phenyl)-4-isopropyl-2H-pyrazol-3-ylmethoxy]-2-methyl-phenyl}-methyl-amino)-methyl]-benzoic acid | LC/MS (ES+): 506.2 |
| 36 | 3-[({4-[2-(2,6-Dichloro-phenyl)-4-isobutyl-5-methyl-2H-pyrazol-3-ylmethoxy]-2-methyl-phenyl}-methyl-amino)-methyl]-benzoic acid | LC/MS (ES+): 566.0, |
| 37 | 4-[({4-[2-(2,6-Dichloro-phenyl)-4-isobutyl-5-methyl-2H-pyrazol-3-ylmethoxy]-2-methyl-phenyl}-methyl-amino)-methyl]-benzoic acid | LC-ES/MS m/e 566.0 (M + 1) |
| 38 | 3-[({4-[2-(2,6-Dichloro-phenyl)-4-ethyl-5-methyl-2H-pyrazol-3-ylmethoxy]-2-methyl-phenyl}-methyl-amino)-methyl]-benzoic acid | LC-ES/MS m/e 538.0 (M + 1) |
| 39 | 4-[({4-[2-(2,6-Dichloro-phenyl)-4-ethyl-5-methyl-2H-pyrazol-3-ylmethoxy]-2-methyl-phenyl}-methyl-amino)-methyl]-benzoic acid | LC-ES/MS m/e 538.0 (M + 1) |
| 40 | 3-[({4-[2-(2,6-Dichloro-phenyl)-5-methyl-4-propyl-2H-pyrazol-3-ylmethoxy]-2-methyl-phenyl}-methyl-amino)-methyl]-benzoic acid | LC-ES/MS m/e 552.0 (M + 1) |
| 41 | 4-[({4-[2-(2,6-Dichloro-phenyl)-5-methyl-4-propyl-2H-pyrazol-3-ylmethoxy]-2-methyl-phenyl}-methyl-amino)-methyl]-benzoic acid | LC-ES/MS m/e 552.0 (M + 1) |
| 42 | 3-(2-{4-[2-(2,6-Dichloro-phenyl)-4-isopropyl-2H-pyrazol-3-ylmethoxy]-2-methyl-phenyl}-vinyl)-benzoic acid | LC-ES/MS m/e 521 (M + 1) |
| 43 | 3-(2-{4-[4-Isopropyl-2-(2-trifluoromethoxy-phenyl)-2H-pyrazol-3-ylmethoxy]-2-methyl-phenyl}-vinyl)-benzoic acid | LC-ES/MS m/e 537 (M + 1) |
| 44 | 3-(2-{4-[2-(2,6-Dichloro-phenyl)-4-ethyl-5-methyl-2H-pyrazol-3-ylmethoxy]-2-methyl-phenyl}-vinyl)-benzoic acid | LC-ES/MS m/e 521 (M + 1) |
| 45 | 3-(2-{4-[2-(2,6-Dichloro-phenyl)-4-methyl-2H-pyrazol-3-ylmethoxy]-2-methyl-phenyl}-vinyl)-benzoic acid | LC-ES/MS m/e 493 (M + 1) |

TABLE 2-continued

| Ex | Chemical Name | Physical Data |
|---|---|---|
| 46 | 3-(2-{4-[2-(2,6-Dichloro-phenyl)-5-methyl-2H-pyrazol-3-ylmethoxy]-2-methyl-phenyl}-vinyl)-benzoic acid | LC-ES/MS m/e 493 (M + 1) |
| 47 | 3-(2-{4-[2-(2,6-Difluoro-phenyl)-4-isopropyl-2H-pyrazol-3-ylmethoxy]-2-methyl-phenyl}-vinyl)-benzoic acid | LC-ES/MS m/e 489.0 (M + 1) |
| 48 | 3-(2-{4-[2-(2,6-Dichloro-phenyl)-4-isobutyl-5-methyl-2H-pyrazol-3-ylmethoxy]-2-methyl-phenyl}-vinyl)-benzoic acid | LC-ES/MS m/e 549.0 (M + 1) |
| 49 | 3-(2-{4-[2-(2,6-Dichloro-phenyl)-5-methyl-4-propyl-2H-pyrazol-3-ylmethoxy]-2-methyl-phenyl}-vinyl)-benzoic acid | LC-ES/MS m/e 535.0 (M + 1) |
| 50 | 3-(2-{4-[2-(2,6-Dichloro-phenyl)-4,5-dimethyl-2H-pyrazol-3-ylmethoxy]-2-methyl-phenyl}-vinyl)-benzoic acid | LC-ES/MS m/e 507.0 (M + 1) |
| 51 | 3-[({4-[2-(2,6-Dichloro-4-fluorophenyl)-4-isopropyl-2H-pyrazol-3-ylmethoxy]-phenyl}-methyl-amino)-methyl]-benzoic acid | LC-ES/MS m/e 554.0 (M − 1) |
| 52 | 3-[({4-[4-Isopropyl-2-(2-trifluoromethylsulfanyl-phenyl)-2H-pyrazol-3-ylmethoxy]-2-methyl-phenyl}-methyl-amino)-methyl]benzoic acid | LC-ES/MS m/e 568.0 (M − 1) |
| 53 | 3-{4'-[2-(2,6-Dichloro-phenyl)-4-isopropyl-2H-pyrazol-3-ylmethoxy]-2'-methyl-biphenyl-3-yl}-propionic acid | LCMS (ES+): 523.3 |
| 54 | {4'-[2-(2,6-Dichloro-phenyl)-4-isopropyl-2H-pyrazol-3-ylmethoxy]-2'-methyl-biphenyl-4-yl}-acetic acid | LCMS (ES+): 509.0 |
| 55 | {4'-[2-(2,6-Dichloro-phenyl)-4-isopropyl-2H-pyrazol-3-ylmethoxy]-2'-methyl-biphenyl-3-yl}-acetic acid | LCMS (ES+): 509.0 |
| 56 | 3-{4'-[2-(2,6-Dichloro-phenyl)-4-isopropyl-2H-pyrazol-3-ylmethoxy]-2'-methyl-biphenyl-3-yl}-acrylic acid | LCMS (ES+): 521.3 |
| 57 | 6-{4-[2-(2,6-Dichloro-phenyl)-4-isopropyl-2H-pyrazol-3-ylmethoxy]-2-methyl-phenyl}-1H-indole-3-carboxylic acid | LCMS (ES+): 534.0 |
| 58 | 6-{4-[2-(2,6-Dichloro-phenyl)-4-isopropyl-2H-pyrazol-3-ylmethoxy]-2-methyl-phenyl}-1H-indole-2-carboxylic acid | LCMS (ES+): 536.0 |
| 59 | 5-{4-[2-(2,6-Dichloro-phenyl)-4-isopropyl-2H-pyrazol-3-ylmethoxy]-2-methyl-phenyl}-1H-indole-3-carboxylic acid | LCMS (ES+): 534.3 |
| 60 | 6-{4-[4-Isopropyl-2-(2-trifluoromethoxy-phenyl)-2H-pyrazol-3-ylmethoxy]-2-methyl-phenyl}-1-methyl-1H-indole-3-carboxylic acid | LCMS (ES+): 564.3 |
| 61 | (5-{4-[2-(2,6-Dichloro-phenyl)-4-isopropyl-2H-pyrazol-3-ylmethoxy]-2-methyl-phenyl}-1H-indol-3-yl)-acetic acid | LCMS (ES+): 548.0 |
| 62 | 6-{4-[2-(2,6-Dichloro-phenyl)-4-isopropyl-2H-pyrazol-3-ylmethoxy]-2-methyl-phenyl}-benzo[b]thiophene-3-carboxylic acid | LCMS (ES+): 548.0 |
| 63 | 6-{4-[2-(2,6-Dichloro-phenyl)-4-isopropyl-2H-pyrazol-3-ylmethoxy]-2-methyl-phenyl}-benzo[b]thiophene-2-carboxylic acid | LCMS (ES+): 551.0 |
| 64 | 6-{4-[4-Isopropyl-2-(2-trifluoromethoxy-phenyl)-2H-pyrazol-3-ylmethoxy]-2-methyl-phenyl}-benzo[b]thiophene-3-carboxylic acid | LCMS (ES+): 567.0 |
| 65 | 6-{4-[4-Isopropyl-2-(2-trifluoromethoxy-phenyl)-2H-pyrazol-3-ylmethoxy]-2-methyl-phenyl}-benzo[b]thiophene-2-carboxylic acid | LCMS (ES+): 567.0 |
| 66 | 4'-[4-Isopropyl-2-(2-trifluoromethoxy-phenyl)-2H-pyrazol-3-ylmethoxy]-2'-methyl-biphenyl-4-carboxylic acid | LC-MS: 509.0 (M − 1). |
| 67 | 3-[({4-[4-Cyclopropyl-2-(2,6-dichloro-phenyl)-2H-pyrazol-3-ylmethoxy]-phenyl}methyl-amino)-methyl]-benzoic acid | LC-ES/MS m/e 534.0 (M − 1). |
| 68 | 3-[({4-[4-Cyclobutyl-2-(2,6-dichloro-phenyl)-2H-pyrazol-3-ylmethoxy]-phenyl}methyl-amino)-methyl]-benzoic acid | LC-ES/MS m/e 548.0 (M − 1). |
| 69 | 3-[({4-[2-(2-Chloro-6-trifluoromethyl-phenyl)-4-isopropyl-2H-pyrazol-3-ylmethoxy}-phenyl}-methyl-amino)-methyl]benzoic acid | LC-ES/MS m/e 516.0 (M − 1) |
| 70 | 3-[({4-[2-(3,5-Difluoro-2-trifluoromethyl-phenyl)-4-isopropyl-2H-pyrazol-3-ylmethoxy]-phenyl}-methyl-amino)-methyl]-benzoic acid | LC-ES/MS m/e 518.0 (M − 1). |
| 71 | 3-[({4-[2-(2-Fluoro-6-trifluoromethyl-phenyl)-4-isopropyl-2H-pyrazol-3-ylmethoxy]-phenyl}-methyl-amino)-methyl]-benzoic acid | LC-ES/MS m/e 500.0 (M − 1) |
| 72 | 4-{4-[2-(2,6-Dichloro-phenyl)-4-isopropyl-2H-pyrazol-3-ylmethoxy]-2-methyl-benzylamino}-benzoic acid | LC-MS: 522.2 (M − 1). |

TABLE 2-continued

| Ex | Chemical Name | Physical Data |
|---|---|---|
| 73 | 4-(1-{4-[2-(2,6-Dichloro-phenyl)-4-isopropyl-2H-pyrazol-3-ylmethoxy]-2-methyl-phenyl}-ethylamino)-benzoic acid | LC-MS: 536.3 (M − 1). |
| 74 | 3-{4'-[2-(2,6-Dichloro-phenyl)-4-isopropyl-2H-pyrazol-3-ylmethoxy]-2'-methyl-biphenyl-4-yl}-propionic acid | LCMS (ES+): 523.3 |
| 75 | 4-[({4-[2-Cyclopropyl-2-(2,6 dichloro-phenyl)-2H-pyrazol-3-ylmethoxy}-2-methyl-phenyl}-methyl-amino)-methyl]-2-methyl-benzoic acid | LC-ES/MS m/e 550.0 (M + 1) |
| 76 | 3-[({4-[2-(Chloro-6-trifluoromethyl-phenyl)-4-cyclopropyl-2H-pyrazol-3-ylmethoxy]-2-methoxy]-2-methyl-phenyl}-methyl-amino)-methyl]-benzoic acid | LC-ES/MS m/e 570.0 (M + 1) |
| 77 | 6-{4-[4-Cyclopropyl-2-(2,6-dichloro-phenyl)-2H-pyrazol-3-ylmethoxy]-2-methyl-phenyl}benzo[d]isothiazole-3-carboxylic acid | LC-ES/MS m/e 550.0 (M + 1) |
| 78 | 6-{4-[4-Cyclopropyl-2-(2-trifluoromethoxy-phenyl)-2H-pyrazol-2-ylmethoxy]-2-methyl-phenyl}-benzo[d]isothiazole-3-carboxyllic acid | LC-ES/MS m/e 566.0 (M + 1) |
| 79 | 6-{4-[4-Cyclopropyl-2-(2,6-dichloro-phenyl)-2H-pyrazol-3-ylmethoxy]-2-methyl-phenyl}-1-methyl-1H-indazole-3-carboxylic acid | LC-ES/MS m/e 547.0 (M + 1) |
| 80 | 4-[({4-[4-Isopropyl-2-(2-trifluoromethoxy-phenyl)-2H-pyrazol-3-ylmethoxy]-2-methyl-phenyl}-methyl-amino)-methyl]-benzoic acid | LC-ES/MS m/e 552.0 (M − 1). |
| 81 | 4-[({4-[2-(2,6-Dichloro-phenyl)-4-isopropyl-2H-pyrazol-3-ylmethoxy]-2-methyl-phenyl}-methyl-amino)-methyl]-benzoic acid | LC-ES/MS m/e 538 (M + 1) |
| 82 | 4-[({4-[4-Cyclopropyl-2-(2-trifluoromethoxy-phenyl)-2H-pyrazol-3-ylmethoxy]-2-methyl-phenyl}-methyl-amino)-methyl]-benzoic acid | LC-ES/MS m/e 552 (M + 1) |
| 83 | 6-{4-[4-Isopropyl-2-(2-trifluoromethoxy-phenyl)-2H-pyrazol-3-ylmethoxy]-2-methyl-phenyl}-1-methyl-1H-indole-3-carboxylic acid | LC-ES/MS m/e 564.3 (M + 1) |
| 84 | 6-{4-[4-Cyclopropyl-2-(2,6-dichloro-phenyl)-2H-pyrazol-3-ylmethoxy]-2-methyl-phenyl}-1-methyl-1H-indole-3-carboxylic acid | LC-ES/MS m/e 546.0 (M + 1) |
| 85 | 6-{4-[2-(2,6-Dichloro-phenyl)-4-isopropyl-2H-pyrazol-3-ylmethoxy]-2-methyl-phenyl}-benzo[b]thiophene-3-carboxylic acid | LC-ES/MS m/e 548.0 (M + 1) |
| 86 | 6-{4-[4-Cyclopropyl-2-(2,6-dichloro-phenyl)-2H-pyrazol-3-ylmethoxy]-2-methyl-phenyl}-benzo[b]thiophene-3-carboxylic acid | LC-ES/MS m/e 549.0 (M + 1) |
| 87 | 4-[({4-[4-Isopropyl-2-(2-trifluoromethoxy-phenyl)-2H-pyrazol-3-ylmethoxy]-2-methyl-phenyl}-methyl-amino)-methyl]-2-methyl-benzoic acid | LC-ES/MS m/e 568.3 (M + 1), 566.3 (M − 1) |

Example 88

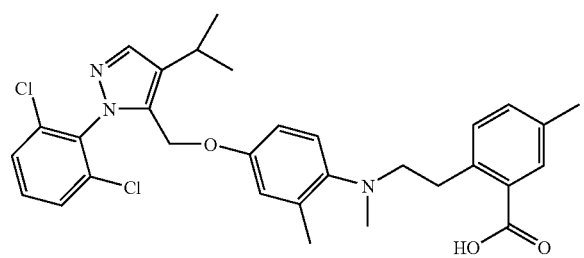

2-[2-({4-[2-(2,6-Dichloro-phenyl)-4-isopropyl-2H-pyrazol-3-ylmethoxy]-2-methyl-phenyl}-methyl-amino)-ethyl]-5-methyl-benzoic Acid

Step A

To a solution of {4-[2-(2,6-dichloro-phenyl)-4-isopropyl-2H-pyrazol-3-ylmethoxy]-2-methyl-phenyl}-methyl-amine (168 mg, 0.416 mmol) in 10 mL 1,2-dichloroethane are added 4-methyl-2-(2-oxo-ethyl)-benzoic acid methyl ester (80 mg, 0.416 mmol) and AcOH (10 mg). The reaction mixture is allowed to stir at room temperature for 15 min and is treated with sodium triacetoxyborohydride (176 mg, 0.832 mmol). The reaction mixture is allowed to stir at room temperature for 2 h and is quenched with water (5 mL). The mixture is concentrated and is extracted twice with ethyl acetate (30 mL). The combined organic layers are dried over sodium sulfate, concentrated under reduced pressure, and purified by flash chromatography eluting with hexanes/ethyl acetate (60:40) to afford the intermediate methyl ester (0.125 g, 52%).

Step B

To a solution of the intermediate methyl ester from Step A (122 mg, 0.210 mmol) in 2.0 mL THF and 1.0 mL MeOH is added sodium hydroxide (2.0 mL, 2.0M in water). The reaction mixture is allowed to stir at 60° C. for 2 h. The reaction mixture is neutralized with HCl (2.0 mL, 2.0 M in water) and the organic solvent is removed under reduced pressure. The resulting residue is extracted twice with ethyl acetate (10 mL). The combined organic layers are dried over sodium sulfate and are concentrated under reduced pressure to afford the title compound (0.110 g, 92%). ES/MS m/e ($^{35}$Cl) 566.3 (M+1)

Example 89

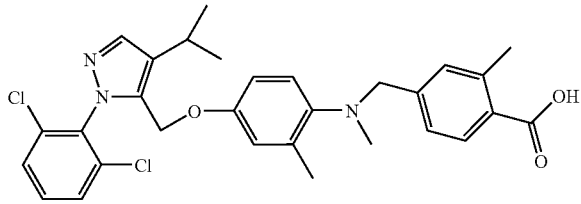

4-[({4-[2-(2,6-Dichloro-phenyl)-4-isopropyl-2H-pyrazol-3-ylmethoxy]-2-methyl-phenyl}-methyl-amino)-methyl]-2-methyl-benzoic Acid The title compound is prepared essentially according to the preparation of 2-[2-({4-[2-(2,6-Dichloro-phenyl)-4-isopropyl-2H-pyrazol-3-ylmethoxy]-2-methyl-phenyl}-methyl-amino)-ethyl]-5-methyl-benzoic acid using the appropriate starting material. LC-ES/MS m/e 552.0 (M+1), 550.0 (M−1)

The compounds listed in table 3 are prepared essentially according to the preparation of 2-[2-({4-[2-(2,6-Dichloro-phenyl)-4-isopropyl-2H-pyrazol-3-ylmethoxy]-2-methyl-phenyl}-methyl-amino)-ethyl]-5-methyl-benzoic acid using the appropriate starting material.

TABLE 3

| Ex | Chemical Name | Physical Data |
|---|---|---|
| 90 | 3-[({4-[2-(2,6-Dichloro-phenyl)-4-isopropyl-2H-pyrazol-3-ylmethoxy]-2-methyl-phenyl}-ethyl-amino)-methyl]-benzoic acid | LC/MS (Es+): 552.0, |
| 91 | 3-[({4-[2-(2,6-Dichloro-phenyl)-4-isopropyl-2H-pyrazol-3-ylmethoxy]-2-methyl-phenyl}-propyl-amino)-methyl]-benzoic acid | LC/MS (Es+): 566.0, |
| 92 | 3-[({4-[2-(2,6-Dichloro-phenyl)-4-isopropyl-2H-pyrazol-3-ylmethoxy]-2-methyl-phenyl}-isobutyl-amino)-methyl]-benzoic acid | LC/MS (ES+): 580.3 |
| 93 | 2-{4-[({4-[2-(2,6-Dichloro-phenyl)-4-isopropyl-2H-pyrazol-3-ylmethoxy]-2-methyl-phenyl}-methyl-amino)-methyl]-phenyl}-2-methyl-propionic acid | LC/MS (Es+): 580.3 |
| 94 | 1-{4-[({4-[2-(2,6-Dichloro-phenyl)-4-isopropyl-2H-pyrazol-3-ylmethoxy]-2-methyl-phenyl}-methyl-amino)-methyl]-phenyl}-cyclopropanecarboxylic acid | LC/MS (ES+): 578.3 |
| 95 | 2-[2-({4-[2-(2,6-Dichloro-phenyl)-4-isopropyl-2H-pyrazol-3-ylmethoxy]-2-methyl-phenyl}-methyl-amino)-ethyl]-benzoic acid | LC/MS (Es+): 552.0, |
| 96 | 3-[2-({4-[2-(2,6-Dichloro-phenyl)-4-isopropyl-2H-pyrazol-3-ylmethoxy]-2-methyl-phenyl}-methyl-amino)-ethyl]-benzoic acid | LC/MS (Es+): 552.0 |
| 97 | 4-[2-({4-[2-(2,6-Dichloro-phenyl)-4-isopropyl-2H-pyrazol-3-ylmethoxy]-2-methyl-phenyl}-methyl-amino)-ethyl]-benzoic acid | LC/MS (ES+): 552.0 |
| 98 | 2-[2-({4-[2-(2,6-Dichloro-phenyl)-4-isopropyl-2H-pyrazol-3-ylmethoxy]-2-methyl-phenyl}-methyl-amino)-ethyl]-4-fluoro-benzoic acid | LC-MS: 570.3 (M + 1), |
| 99 | 2-[2-({4-[2-(2,6-Dichloro-phenyl)-4-isopropyl-2H-pyrazol-3-ylmethoxy]-2-methyl-phenyl}-methyl-amino)-ethyl]-5-methoxy-benzoic acid | LC-MS: 582.5 (M + 1), |
| 100 | 4-Chloro-2-[2-({4-[2-(2,6-dichloro-phenyl)-4-isopropyl-2H-pyrazol-3-ylmethoxy]-2-methyl-phenyl}-methyl-amino)-ethyl]-benzoic acid | LC-MS: 588.3 (M + 1), |
| 101 | 2-[2-({4-[2-(2,6-Dichloro-phenyl)-4-isopropyl-2H-pyrazol-3-ylmethoxy]-2-methyl-phenyl}-methyl-amino)-ethyl]-4-methyl-benzoic acid | LC-MS: 566.5 (M + 1), |
| 102 | 3-[2-({4-[2-(2,6-Dichloro-phenyl)-4-isopropyl-2H-pyrazol-3-ylmethoxy]-2-methyl-phenyl}-methyl-amino)-ethyl]-4-methyl-benzoic acid | LC-MS: 566.0 (M + 1), |
| 103 | 2-Butoxy-5-[2-({4-[2-(2,6-dichloro-phenyl)-4-isopropyl-2H-pyrazol-3-ylmethoxy]-2-methyl-phenyl}-methyl-amino)-ethyl]-benzoic acid | LC-MS: 624.3 (M + 1), |
| 104 | 4-Butoxy-3-[2-({4-[2-(2,6-dichloro-phenyl)-4-isopropyl-2H-pyrazol-3-ylmethoxy]-2-methyl-phenyl}-methyl-amino)-ethyl]-benzoic acid | LC-MS: 624.3 (M + 1), |
| 105 | 3-[2-({4-[2-(2,6-Dichloro-phenyl)-4-isopropyl-2H-pyrazol-3-ylmethoxy]-2-methyl-phenyl}-methyl-amino)-ethyl]-4-fluoro-benzoic acid | LC-MS: 570.0 (M + 1), |
| 106 | 5-[2-({4-[2-(2,6-Dichloro-phenyl)-4-isopropyl-2H-pyrazol-3-ylmethoxy]-2-methyl-phenyl}-methyl-amino)-ethyl]-2-fluoro-benzoic acid | LC-MS: 570.0 (M + 1), |
| 107 | 4-[({4-[2-(2,6-Dichloro-phenyl)-4-isopropyl-2H-pyrazol-3-ylmethoxy]-2-methyl-phenyl}-methyl-amino)-methyl]-3-formylamino-benzoic acid | LC-MS: 581.0 (M + 1). |
| 108 | 2-Benzyloxy-4-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 644.0 (M + 1), 642.0 (M − 1). |

TABLE 3-continued

| Ex | Chemical Name | Physical Data |
|---|---|---|
| 109 | 4-[({4-[2-(2,6-Dichloro-phenyl)-4-isopropyl-2H-pyrazol-3-ylmethoxy]-2-methyl-phenyl}-methyl-amino)-methyl]-2-pentyl-benzoic acid | LC-MS: 608.3 (M + 1), 606.0 (M − 1). |
| 110 | 2-Butyrylamino-4-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 623.0 (M + 1), 621.0 (M − 1). |
| 111 | 4-[({4-[2-(2,6-Dichloro-phenyl)-4-isopropyl-2H-pyrazol-3-ylmethoxy]-2-methyl-phenyl}-methyl-amino)-methyl]-2-trifluoromethyl-benzoic acid | LC-MS: 606.0 (M + 1), 604.0 (M − 1). |
| 112 | 3-[({4-[2-(2,6-Dichloro-phenyl)-4-isopropyl-2H-pyrazol-3-ylmethoxy]-2-methyl-phenyl}-methyl-amino)-methyl]-5-trifluoromethyl-benzoic acid | LC-MS: 606.0 (M + 1), 604.0 (M − 1). |
| 113 | 5-[({4-[2-(2,6-Dichloro-phenyl)-4-isopropyl-2H-pyrazol-3-ylmethoxy]-2-methyl-phenyl}-methyl-amino)-methyl]-2-fluoro-benzoic acid | LC-MS: 556.0 (M + 1), 554.0 (M − 1). |
| 114 | 3-[({4-[2-(2,6-Dichloro-phenyl)-4-isopropyl-2H-pyrazol-3-ylmethoxy]-2-methyl-phenyl}-methyl-amino)-methyl]-4-methoxy-benzoic acid | LC-MS: 568.0 (M + 1), 566.0 (M − 1) |
| 115 | 5-[({4-[2-(2,6-dichloro-phenyl)-4-isopropyl-2H-pyrazol-3-ylmethoxy]-2-methyl-phenyl}-methyl-amino)-methyl]-1H-pyrrole-2-carboxylic acid | LC-MS: 527.0 (M + 1), 525.0 (M − 1). |
| 116 | 2-[({4-[2-(2,6-dichloro-phenyl)-4-isopropyl-2H-pyrazol-3-ylmethoxy]-2-methyl-phenyl}-methyl-amino)-methyl]-furan-3-carboxylic acid | LC-MS: 528.0 (M + 1), 526.0 (M − 1). |
| 117 | 3-{4-[2-(2,6-Dichloro-phenyl)-4-isopropyl-2H-pyrazol-3-ylmethoxy]-2-methyl-benzylamino}-4-methyl-benzoic acid | LC-MS: 536.0 (M − 1). |
| 118 | 3-Butoxy-5-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 610.0 (M + 1), 608.3 (M − 1) |
| 119 | 5-[({4-[2-(2,6-dichloro-phenyl)-4-isopropyl-2H-pyrazol-3-ylmethoxy]-2-methyl-phenyl}-methyl-amino)-methyl]-thiophene-2-carboxylic acid | LC-MS: 544.0 (M + 1), 542.0 (M − 1). |
| 120 | 2-[({4-[2-(2,6-dichloro-phenyl)-4-isopropyl-2H-pyrazol-3-ylmethoxy]-2-methyl-phenyl}-methyl-amino)-methyl]-oxazole-4-carboxylic acid | LC-MS: 529.0 (M + 1), 527.0 (M − 1) |
| 121 | 2-Benzoyl-4-[({4-[2-(2,6-dichloro-phenyl)-4-isopropyl-2H-pyrazol-3-ylmethoxy]-2-methyl-phenyl}-methyl-amino)-methyl]-benzoic acid | LC-MS m/e 642.0 (M + 1), 640.0 (M − 1) |

Example 122

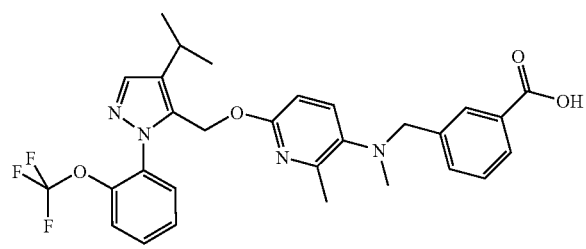

Step A

3-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic Acid Methyl Ester To an ambient temperature solution of 6-[4-isopropyl-2-(2-trifluoromethoxy-phenyl)-2H-pyrazol-3-ylmethoxy]-2-methyl-pyridin-3-ylamine (100 mg, 0.246 mmol) in MeOH (3 mL) is added 3-formyl-benzoic acid methyl ester (40 mg, 0.246 mmol). The reaction mixture is stirred at room temperature for 10 min. Decaborane (12 mg, 0.0738 mmol) is added and the reaction mixture is stirred at room temperature. After 2 h, formaldehyde (2.0 mL, 37 wt % in water) is added and the reaction mixture is stirred at room temperature for 10 min. Decaborane (12 mg, 0.0738 mmol) is added and the reaction is stirred at room temperature. After 2 h, the reaction mixture is concentrated and the residue is chromatographed (SiO$_2$ 40 g, 0% to 20% EtOAc/Hex) to yield the title compound (97 mg, 69%). $^1$H NMR (400 MHz, DMSO) δ 7.91-7.88 (m, 1H), 7.81 (dt, 1H, J=4.6, 2.5 Hz), 7.63 (s, 1H), 7.59-7.50 (m, 4H), 7.48-7.41 (m, 3H), 6.39 (d, 1H, J=7.9 Hz), 5.13 (s, 2H), 4.00 (s, 2H), 3.82 (s, 3H), 3.03 (sept, 1H, J=6.6 Hz), 2.46 (s, 3H), 2.32 (s, 3H), 1.18 (d, 6H, J=6.6 Hz).

Step B

3-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic Acid To an ambient temperature solution of 3-[({6-[4-Isopropyl-2-(2-trifluoromethoxy-phenyl)-2H-pyrazol-3-yl-methoxy]-2-methyl-pyridin-3-yl}-methyl-amino)-methyl]-benzoic acid methyl ester (106 mg, 0.186 mmol) in dioxane (2 mL) is added a solution of lithium hydroxide (279 μL, 0.558 mmol, 2.0N in water). The reaction mixture is heated to 50° C. The reaction is concentrated under reduced pressure and the residue is partitioned between Et$_2$O and water. The aqueous layer pH is adjusted to approximately 7 and is extracted with a second portion of Et$_2$O. The combined organic layers are washed with water, dried (MgSO$_4$), filtered, and concentrated to yield the title compound (99 mg, 96%). ES/MS m/e 555.3 (M+1)

The compounds listed in table 4 are prepared essentially according to the preparation of 3-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic acid using the appropriate starting material.

TABLE 4

| Ex | Chemical Name | Physical Data |
|---|---|---|
| 123 | 4-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic acid | LC/MS (ES+): 555.3 |
| 124 | 5-[({6-[4-Isopropyl-2-(2-trifluoromethoxy-phenyl)-2H-pyrazol-3-ylmethoxy]-2-methyl-pyridin-3-yl}-methyl-amino)-methyl]-2-methoxy-benzoic acid | LC/MS (ES+): 585.3 |
| 125 | 4-[({6-[4-Isopropyl-2-(2-trifluoromethoxy-phenyl)-2H-pyrazol-3-ylmethoxy]-2-methyl-pyridin-3-yl}-methyl-amino)-methyl]-2-pentyl-benzoic acid | LC/MS (ES+): 625.3 |
| 126 | 4-[({6-[4-Isopropyl-2-(2-trifluoromethoxy-phenyl)-2H-pyrazol-3-ylmethoxy]-2-methyl-pyridin-3-yl}-methyl-amino)-methyl]-2-methyl-benzoic acid | LC/MS (ES+): 569.0 |
| 127 | 4-[({6-[4-Isopropyl-2-(2-trifluoromethoxy-phenyl)-2H-pyrazol-3-ylmethoxy]-2-methyl-pyridin-3-yl}-methyl-amino)-methyl]-2-pent-1-ynyl-benzoic acid | LC-ES/MS m/e 621.0 (M + 1), 100% |

Example 128

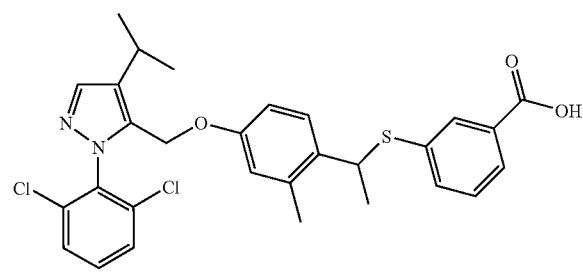

Step A 3-(1-{4-[2-(2,6-Dichloro-phenyl)-4-isopropyl-2H-pyrazol-3-ylmethoxy]-2-methyl-phenyl}-ethylsulfanyl)-benzoic Acid Methyl Ester To an ambient temperature solution of 1-{4-[2-(2,6-Dichloro-phenyl)-4-isopropyl-2H-pyrazol-3-ylmethoxy]-2-methyl-phenyl}-ethanol (75 mg, 1.78 mmol) in toluene (20 mL) are added 3-Mercapto-benzoic acid methyl ester (299 mg, 1.78 mmol) and tri-N-butylphosphine (668 µL, 2.68 mmol). The reaction mixture is cooled to 0° C. 1,1'-(Azocarbonyl)-dipiperidine (676 mg, 2.68 mmol) is added and the reaction mixture is warmed to room temperature overnight. The reaction mixture is concentrated and the residue is chromatographed (40 g SiO$_2$, 0% to 30% EtOAc/Hexanes) to yield the title compound (541 mg, 54%). $^1$H NMR (400 MHz, CDCl$_3$) δ 8.00-7.98 (m, 1H), 7.99 (t, 1H, J=1.8 Hz), 7.87 (dt, 1H, J=4.6, 2.5 Hz), 7.70 (s, 1H), 7.43-7.39 (m, 3H), 7.32-7.22 (m, 3H), 6.61-6.54 (m, 2H), 4.79 (s, 2H), 4.53 (q, 1H, J=7.0 Hz), 3.90 (s, 3H), 2.99 (sept, 1H, J=6.6 Hz), 2.32 (s, 3H), 1.56 (d, 3H, J=6.9 Hz), 1.30 (d, 6H, J=6.6 Hz).

Step B 4-(1-{4-[2-(2,6-Dichloro-phenyl)-4-isopropyl-2H-pyrazol-3-ylmethoxy]-2-methyl-phenyl}-ethylsulfanyl)-benzoic Acid To an ambient temperature solution of 3-(1-{4-[2-(2,6-Dichloro-phenyl)-4-isopropyl-2H-pyrazol-3-ylmethoxy]-2-methyl-phenyl}-ethylsulfanyl)-benzoic acid methyl ester (10 mg, 0.0176 mmol) in dioxane (2 mL) is added a solution of lithium hydroxide (26 µL, 0.052 mmol, 2.0N in water). The reaction mixture is heated to 50° C. The reaction mixture is concentrated and the residue is partitioned between Et$_2$O and water. The aqueous layer pH is adjusted to approximately 4 and is extracted with a second portion of Et$_2$O. The combined organic layers are washed with water, dried (MgSO$_4$), filtered and concentrated to yield the title compound (10 mg, quant). ES/MS m/e ($^{35}$Cl) 556.3 (M+1)

Example 129

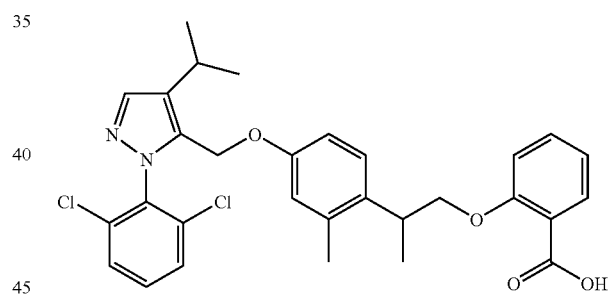

2-(2-{4-[2-(2,6-Dichloro-phenyl)-4-isopropyl-2H-pyrazol-3-ylmethoxy]-2-methyl-phenyl}-propoxy)-benzoic Acid The title compound is prepared essentially according to the preparation of 4-(1-{4-[2-(2,6-Dichloro-phenyl)-4-isopropyl-2H-pyrazol-3-ylmethoxy]-2-methyl-phenyl}-ethylsulfanyl)-benzoic acid using the appropriate starting material. Racemate LC/MS (ES+): 553.0, Isomer 1 LC/MS (ES+): 553.0, Isomer 2 LC/MS (ES+): 553.0

The compounds listed in table 5 are prepared essentially according to the preparation of 4-(1-{4-[2-(2,6-Dichloro-phenyl)-4-isopropyl-2H-pyrazol-3-ylmethoxy]-2-methyl-phenyl}-ethylsulfanyl)-benzoic acid using the appropriate starting material.

TABLE 5[1]

| Ex | Chemical Name | Physical Data |
|---|---|---|
| 130 | 2-(2-{4-[2-(2,6-Dichloro-phenyl)-4-isopropyl-2H-pyrazol-3-ylmethoxy]-2-methyl-phenyl}-ethoxy)-6-methyl-benzoic acid | LC/MS (ES+): 553.0, |
| 131 | 3-(2-{4-[2-(2,6-Dichloro-phenyl)-4-isopropyl-2H-pyrazol-3-ylmethoxy]-2-methyl-phenyl}-ethoxy)-naphthalene-2-carboxylic acid | LC/MS (ES+): 589.0, |
| 132 | 5-Chloro-2-(2-{4-[2-(2,6-dichloro-phenyl)-4-isopropyl-2H-pyrazol-3-ylmethoxy]-2-methyl-phenyl}-ethoxy)-benzoic acid | LC/MS (ES+): 573.0 |
| 133 | 2-(2-{4-[2-(2,6-Dichloro-phenyl)-4-isopropyl-2H-pyrazol-3-ylmethoxy]-2-methyl-phenyl}-ethoxy)-5-methoxy-benzoic acid | LC/MS (ES+): 569.0 |
| 134 | 2-(2-{4-[2-(2,6-Dichloro-phenyl)-4-isopropyl-2H-pyrazol-3-ylmethoxy]-2-methyl-phenyl}-ethoxy)-5-methyl-benzoic acid | LC/MS (ES+): 553.0 |
| 135 | 4-(2-{4-[2-(2,6-Dichloro-phenyl)-4-isopropyl-2H-pyrazol-3-ylmethoxy]-2-methyl-phenyl}-ethoxy)-benzoic acid | LC/MS (ES+): 539.0 |
| 136 | 3-(2-{4-[2-(2,6-Dichloro-phenyl)-4-isopropyl-2H-pyrazol-3-ylmethoxy]-2-methyl-phenyl}-ethoxy)-benzoic acid | LC/MS (ES+): 539.0 |
| 137 | 2-(2-{4-[2-(2,6-Dichloro-phenyl)-4-isopropyl-2H-pyrazol-3-ylmethoxy]-2-methyl-phenyl}-ethoxy)-benzoic acid | LC/MS (ES+): 539.0 |
| 138 | 2-(2-{4-[2-(2,6-Dichloro-phenyl)-4-isopropyl-2H-pyrazol-3-ylmethoxy]-2-methyl-phenyl}-propoxy)-6-methyl-benzoic acid | LC/MS (ES+): 567.0 |
| 139 | 2-(2-{4-[2-(2,6-Dichloro-phenyl)-4-isopropyl-2H-pyrazol-3-ylmethoxy]-2-methyl-phenyl}-propoxy)-5-methyl-benzoic acid | LC/MS (ES+): 567.0 |
| 140 | 2-(2-{4-[2-(2,6-Dichloro-phenyl)-4-isopropyl-2H-pyrazol-3-ylmethoxy]-2-methyl-phenyl}-propoxy)-4-methyl-benzoic acid | LC/MS (ES+): 567.0 |
| 141 | 2-(2-{4-[2-(2,6-Dichloro-phenyl)-4-isopropyl-2H-pyrazol-3-ylmethoxy]-2-methyl-phenyl}-propoxy)-3-methyl-benzoic acid | LC/MS (ES+): 567.0, |
| 142 | 3-(2-{4-[2-(2,6-Dichloro-phenyl)-4-isopropyl-2H-pyrazol-3-ylmethoxy]-2-methyl-phenyl}-propoxy)-benzoic acid | Racemate LC/MS (ES+): 553.0, Isomer 1 LC/MS (ES+): 553.0, Isomer 2 LC/MS (ES+): 553.0 |
| 143 | 4-(2-{4-[2-(2,6-Dichloro-phenyl)-4-isopropyl-2H-pyrazol-3-ylmethoxy]-2-methyl-phenyl}-propoxy)-benzoic acid | Racemate LC/MS (ES+): 553.0, Isomer 1 LC/MS (ES+): 553.0, Isomer 2 LC/MS (ES+): 553.0 |
| 144 | 3-(1-{4-[2-(2,6-Dichloro-phenyl)-4-isopropyl-2H-pyrazol-3-ylmethoxy]-2-methyl-phenyl}-ethylsulfanyl)-benzoic acid | Racemate LC/MS (ES+): 555.0, Isomer 1 LC/MS (ES+): 555.0, Isomer 2 LC/MS (ES+): 555.0 |
| 145 | 4-(1-{4-[2-(2,6-Dichloro-phenyl)-4-isopropyl-2H-pyrazol-3-ylmethoxy]-2-methyl-phenyl}-ethylsulfanyl)-benzoic acid | Racemate LC/MS (ES+): 555.0, Isomer 1 LC/MS (ES+): 555.0, Isomer 2 LC/MS (ES+): 555.0 |

TABLE 5[1]-continued

| Ex | Chemical Name | Physical Data |
|---|---|---|
| 146 | 3-(1-{4-[4-Isopropyl-2-(2-trifluoromethoxy-phenyl)-2H-pyrazol-3-ylmethoxy]-2-methyl-phenyl}-ethylsulfanyl)-benzoic acid | Racemate LC/MS (ES+): 571.0, Isomer 1 LC/MS (ES+): 571.0, Isomer 2 LC/MS (ES+): 571.0 |
| 147 | 3-(1-{6-[2-(2,6-Dichloro-phenyl)-4-isopropyl-2H-pyrazol-3-ylmethoxy]-pyridin-3-yl}-ethylsulfanyl)-benzoic acid | Racemate LC/MS (ES+): 542.0, Isomer 1 LC/MS (ES+): 542.0, Isomer 2 LC/MS (ES+): 542.0 |
| 148 | 4-(1-{6-[2-(2,6-Dichloro-phenyl)-4-isopropyl-2H-pyrazol-3-ylmethoxy]-pyridin-3-yl}-ethylsulfanyl)-benzoic acid | Racemate LC/MS (ES+): 542.0, Isomer 1 LC/MS (ES+): 542.0, Isomer 2 LC/MS (ES+): 542.0 |
| 149 | 3-(1-{6-[2-(2,6-Dichloro-phenyl)-4-isopropyl-2H-pyrazol-3-ylmethoxy]-pyridin-3-yl}-ethylsulfanyl)-benzoic acid | Racemate LC/MS (ES+): 542.0, Isomer 1 LC/MS (ES+): 542.0, Isomer 2 LC/MS (ES+): 542.0 |
| 150 | 3-(1-{4-[2-(2,6-Dichloro-phenyl)-4-isopropyl-2H-pyrazol-3-ylmethoxy]-phenyl}-ethylsulfanyl)-benzoic acid | LC/MS (ES+): 541.0, |
| 151 | 4-(1-{4-[2-(2,6-Dichloro-phenyl)-4-isopropyl-2H-pyrazol-3-ylmethoxy]-phenyl}-ethylsulfanyl)-benzoic acid | LC/MS (ES+): 541.0, |
| 152 | 3-{4-[2-(2,6-Dichloro-phenyl)-4-isopropyl-2H-pyrazol-3-ylmethoxy]-2-methyl-benzyloxy}-benzoic acid | LC/MS (ES+): 525.0, |
| 153 | 4-{4-[2-(2,6-Dichloro-phenyl)-4-isopropyl-2H-pyrazol-3-ylmethoxy]-2-methyl-benzyloxy}-benzoic acid | LC/MS (ES+): 525.0, |
| 154 | (3-{4-[2-(2,6-Dichloro-phenyl)-4-isopropyl-2H-pyrazol-3-ylmethoxy]-2-methyl-benzyloxy}-phenyl)-acetic acid | LC/MS (ES+): 539.0 |
| 155 | (4-{4-[2-(2,6-Dichloro-phenyl)-4-isopropyl-2H-pyrazol-3-ylmethoxy]-2-methyl-benzyloxy}-phenyl)-acetic acid | LC/MS (ES+): 539.0 |
| 156 | 4-{4-[2-(2,6-Dichloro-phenyl)-4-isopropyl-2H-pyrazol-3-ylmethoxy]-2-methyl-benzyloxy}-2-propyl-benzoic acid | LC/MS (ES+): 567.0, |
| 157 | 5-{4-[2-(2,6-Dichloro-phenyl)-4-isopropyl-2H-pyrazol-3-ylmethoxy]-2-methyl-benzyloxy}-2-propyl-benzoic acid | LC/MS (ES+): 567.0 |
| 158 | 4-{4-[2-(2,6-Dichloro-phenyl)-4-isopropyl-2H-pyrazol-3-ylmethoxy]-2-methyl-benzyloxy}-2-methyl-benzoic acid | LC/MS (ES+): 539.0 |
| 159 | 3-(1-{4-[2-(2,6-Dichloro-phenyl)-4-isopropyl-2H-pyrazol-3-ylmethoxy]-2-methyl-phenyl}-ethoxy)-benzoic acid | Racemate LC/MS (ES+): 539.0, Isomer 1 LC/MS (ES+): 539.0, Isomer 2 LC/MS (ES+): 539.0, |
| 160 | 4-(1-{4-[2-(2,6-Dichloro-phenyl)-4-isopropyl-2H-pyrazol-3-ylmethoxy]-2-methyl-phenyl}-ethoxy)-benzoic acid | Racemate LC/MS (ES+): 537.0, Isomer 1 LC/MS (ES+): 537.0, Isomer 2 LC/MS (ES+): 537.0, |

TABLE 5[1]-continued

| Ex | Chemical Name | Physical Data |
|---|---|---|
| 161 | 3-(1-{6-[2-(2,6-Dichloro-phenyl)-4-isopropyl-2H-pyrazol-3-ylmethoxy]-pyridin-3-yl}-ethoxy)-benzoic acid | Racemate LC/MS (ES+): 526.0, Isomer 1 LC/MS (ES+): 526.0, Isomer 2 LC/MS (ES+): 526.0, |
| 162 | 4-(1-{6-[2-(2,6-Dichloro-phenyl)-4-isopropyl-2H-pyrazol-3-ylmethoxy]-pyridin-3-yl}-ethoxy)-benzoic acid | Racemate LC/MS (ES+): 526.0, Isomer 1 LC/MS (ES+): 526.0, Isomer 2 LC/MS (ES+): 526.0, |
| 163 | 3-(1-{4-[2-(2,6-Dichloro-phenyl)-4-isopropyl-2H-pyrazol-3-ylmethoxy]-phenyl}-ethoxy)-benzoic acid | LC/MS (ES+): 525.0, |
| 164 | 4-(1-{4-[2-(2,6-Dichloro-phenyl)-4-isopropyl-2H-pyrazol-3-ylmethoxy]-phenyl}-ethoxy)-benzoic acid | LC/MS (ES+): 525.0 |
| 165 | 4-[({4-[2-Cyclopropyl-2-(trifluoromethoxy-phenyl-2H-pyrazol-3-ylmethoxy}-2-methyl-phenyl}-methyl-amino)-methyl]-2-methyl-benzoic acid methyl ester | LC-ES/MS m/e 580.0 (M + 1) |
| 166 | 2-{4-[2-(2,6-Dichloro-phenyl)-4-isopropyl-2H-pyrazol-3-ylmethoxy]-2-methyl-phenyl}-benzo[b]thiophene-5-carboxylic acid | LC-ES/MS m/e 551 (M + 1) |
| 167 | 4-[({2-Chloro-4-[4-isopropyl-2-(2-trifluoromethoxy-phenyl)-2H-pyrazol-3-ylmethoxy]-phenyl}-methyl-amino)-methyl]-2-methyl-benzoic acid | LC-ES/MS m/e 588.2 (M + 1) |
| 168 | 4-[({2-Chloro-4-[4-cyclopropyl-2-(2,6-dichloro-phenyl)-2H-pyrazol-3-ylmethoxy]-phenyl}-methyl-amino)-methyl]-2-methyl-benzoic acid | LC-ES/MS m/e 570.0 (M + 1) |
| 169 | 4-[({2-Chloro-4-[2-(2,6-dichloro-phenyl)-4-isopropyl-2H-pyrazol-3-ylmethoxy]-phenyl}-methyl-amino)-methyl]-2-methyl-benzoic acid | LC-ES/MS m/e 574.0 (M + 1) |
| 170 | 4-[({4-[4-Cyclopropyl-2-(2,6-dichloro-phenyl)-2H-pyrazol-3-ylmethoxy]-2-fluoro-phenyl}-methyl-amino)-methyl]-2-methyl-benzoic acid | LC-ES/MS m/e 554.0 (M + 1) |
| 171 | 4-[({4-[2-(2,6-Dichloro-phenyl)-4-isopropyl-2H-pyrazol-3-ylmethoxy]-2-fluoro-phenyl}-methyl-amino)-methyl]-2-methyl-benzoic acid | LC-ES/MS m/e 556.0 (M + 1) |
| 172 | 4-[({4-[2-(2,6-Dichloro-phenyl)-4-isopropyl-2H-pyrazol-3-ylmethoxy]-phenyl}-methyl-amino)-methyl]-2-methyl-benzoic acid | LC-ES/MS m/e 538.2 (M + 1) |
| 173 | 4'-[4-Cyclopropyl-2-(2,6-dichloro-phenyl)-2H-pyrazol-3-ylmethoxy]-2'-methyl-biphenyl-4-carboxylic acid | ES/MS m/e 493.0 (M + 1) |
| 174 | 6-{4-[4-Cyclopropyl-2-(2-trifluoromethoxy-phenyl)-2H-pyrazol-3-ylmethoxy]-2-methyl-phenyl}-benzo[d]isothiazole-3-carboxylic acid | ES/MS m/e 566.0 (M + 1) |
| 175 | 6-{4-[4-Cyclopropyl-2-(2-trifluoromethoxy-phenyl)-2H-pyrazol-3-ylmethoxy]-2-methyl-phenyl}-1-methyl-1H-indole-3-carboxylic acid | ES/MS m/e 562.0 (M + 1) |
| 176 | 6-{4-[4-Cyclopropyl-2-(2-trifluoromethoxy-phenyl)-2H-pyrazol-3-ylmethoxy]-2-methyl-phenyl}-1-isopropyl-1H-indole-3-carboxylic acid | ES/MS m/e 590.0 (M + 1) |
| 177 | 6-{4-[4-Cyclopropyl-2-(2-trifluoromethoxy-phenyl)-2H-pyrazol-3-ylmethoxy]-2-methyl-phenyl}-1,2-dimethyl-1H-indole-3-carboxylic acid | ES/MS m/e 576.0 (M + 1) |
| 178 | 6-{4-[4-Cyclopropyl-2-(2-trifluoromethoxy-phenyl)-2H-pyrazol-3-ylmethoxy]-2-methyl-phenyl}-benzo[b]thiophene-3-carboxylic acid | ES/MS m/e 565.0 (M + 1) |
| 179 | 4-[({4-[4-Cyclopropyl-2-(2-trifluoromethoxy-phenyl)-2H-pyrazol-3-ylmethoxy]-2-methyl-phenyl}-methyl-amino)-methyl]-benzoic acid | ES/MS m/e 552.2 (M + 1) |
| 180 | 2-{4-[2-(2,6-Dichloro-phenyl)-4-isopropyl-2H-pyrazol-3-ylmethoxy]-2-methyl-phenyl}-benzo[b]thiophene-7-carboxylic acid | LC-ES/MS m/e 551 (M + 1) |

[1]When present, individual enantiomers are isolated from the racemic mixture via chiral chromatography. Isomer 1 elutes from the column first and isomer 2 elutes from the column second.

Example 181

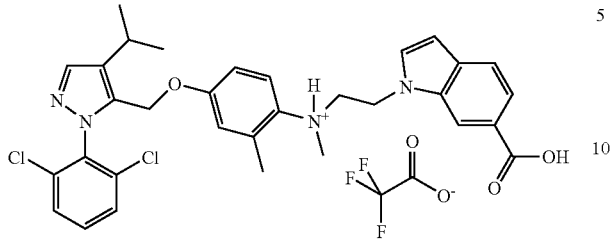

[2-(6-Carboxy-indol-1-yl)-ethyl]-{4-[2-(2,6-dichloro-phenyl)-4-isopropyl-2H-pyrazol-3-yl-methoxy]-2-methyl-phenyl}-methyl-ammonium; trifluoro-acetate

Step A

To a 0° C. suspension of sodium hydride (10 mg, 0.235 mmol, 60% oil dispersion) in DMF (2 mL) is added a solution of 1H-indole-2-carboxylic acid methyl ester (34 mg, 0.195 mmol) in DMF (2 mL) dropwise. The reaction is warmed to room temperature over 30 min. The reaction is cooled to 0° C. and a solution of (2-Bromo-ethyl)-{4-[2-(2,6-dichloro-phenyl)-4-isopropyl-2H-pyrazol-3-ylmethoxy]-2-methyl-phenyl}-methyl-amine (80 mg, 0.156 mmol) in DMF (2 mL) is added dropwise. The reaction is warmed to room temperature and is stirred overnight. The reaction mixture is quenched with saturated aqueous ammonium chloride and is concentrated under reduced pressure. The residue is partitioned between Et$_2$O and water. The aqueous layer is extracted with Et$_2$O and the combined organic layers are washed with brine, dried (MgSO$_4$), filtered, and concentrated under reduced pressure to yield a mixture of ester and carboxylic acid products (83 mg, 88%).

Step B

To an ambient temperature solution of the methyl ester from Step A (83 mg, 0.137 mmol) in MeOH/water (1/1 mL) is added potassium hydroxide (231 mg, 4.11 mmol). The reaction mixture is heated to 80° C. overnight. The reaction mixture is concentrated and the residue is partitioned between Et$_2$O and water. The pH of the aqueous layer is adjusted to 6-7. The aqueous layer is extracted with Et$_2$O and the combined organic layers are washed with water, dried (MgSO$_4$), filtered, and concentrated under reduced pressure. The residue is purified via reversed phase HPLC (C18 OBD 19×100 mm, 30 to 70% ACN/water (0.1% TFA) at 20 mL/min) to yield the title compound (64 mg, 66%). ES/MS m/e ($^{37}$Cl) 593.0 (M+1)

The compounds listed in table 6 are prepared essentially according to the preparation of [2-(6-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate using the appropriate starting material.

TABLE 6

| Ex | Chemical Name | Physical Data |
|---|---|---|
| 182 | [2-(4-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 593.0 |
| 183 | [2-(2-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 593.0 |
| 184 | [2-(3-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 593.0 |
| 185 | [2-(5-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 593.0 |
| 186 | [2-(6-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 593.0 |
| 187 | [2-(7-Carboxy-indol-1-yl)-ethyl]-{4-[2-(2,6-dichloro-phenyl)-4-isopropyl-2H-pyrazol-3-ylmethoxy]-2-methyl-phenyl}-methyl-ammonium; trifluoro-acetate | LC/MS (ES+): 591.0 |

Example 188

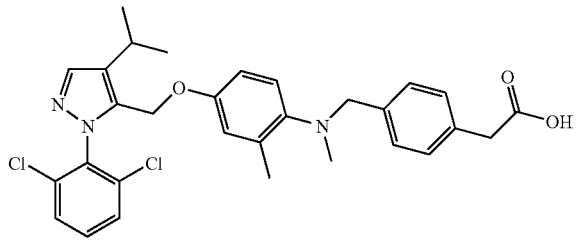

Step A

{4-[({4-[2-(2,6-Dichloro-phenyl)-4-isopropyl-2H-pyrazol-3-ylmethoxy]-2-methyl-phenyl}-methyl-amino)-methyl]-phenyl}-acetic Acid Methyl Ester To an ambient temperature solution of {4-[2-(2,6-dichloro-phenyl)-4-isopropyl-2H-pyrazol-3-ylmethoxy]-2-methyl-phenyl}-methyl-amine (82 mg, 0.204 mmol) in acetonitrile (3 mL) are added (4-bromomethyl-phenyl)-acetic acid methyl ester (52 mg, 0.214 mmol) and cesium carbonate (133 mg, 0.408 mmol). The reaction mixture is heated to 80° C. overnight. The reaction mixture is concentrated under reduced pressure. The residue is chromatographed (SiO$_2$ 40 g, 0% to 20% EtOAc/Hex). Reversed phase HPLC (C18 OBD 19×100 mm, 30 to 70% ACN/water (0.1% TFA) at 20 mL/min) is employed to remove approximately 10% starting amine present to yield the title compound (78 mg, 68%). LC-ES/MS m/e 566.3 (M+1), 95%

Step B

{4-[({4-[2-(2,6-Dichloro-phenyl)-4-isopropyl-2H-pyrazol-3-ylmethoxy]-2-methyl-phenyl}-methyl-amino)-methyl]-phenyl}-acetic Acid To an ambient temperature solution of {4-[({4-[2-(2,6-Dichloro-phenyl)-4-isopropyl-2H-pyrazol-3-ylmethoxy]-2-methyl-phenyl}-methyl-amino)-methyl]-phenyl}-acetic acid methyl ester (81 mg, 0.143 mmol) in dioxane (2 mL) is added a solution of lithium hydroxide (215 μL, 0.429 mmol, 2.0N in water). The reaction mixture is heated to 50° C. The reaction is concentrated and the residue is partitioned between Et$_2$O and water. The aqueous layer pH is adjusted to approximately 7 and the aqueous layer is extracted with a second portion of Et$_2$O. The combined organic layers are washed with water, dried (MgSO$_4$), filtered, and concentrated to yield the title compound (75 mg, 95%). ES/MS m/e ($^{35}$Cl) 552.0 (M+1).

Example 189

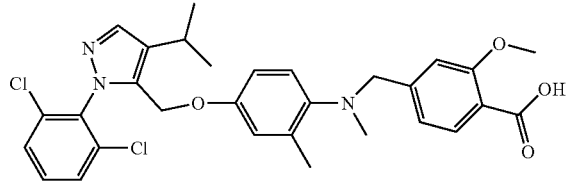

4-[({4-[2-(2,6-Dichloro-phenyl)-4-isopropyl-2H-pyrazol-3-ylmethoxy]-2-methyl-phenyl}-methyl-amino)-methyl]-2-methoxy-benzoic Acid The title compound is prepared essentially according to the preparation of {4-[({4-[2-(2,6-Dichloro-phenyl)-4-isopropyl-2H-pyrazol-3-ylmethoxy]-2-methyl-phenyl}-methyl-amino)-methyl]-phenyl}-acetic acid using the appropriate starting material. LC-ES/MS m/e 568.0 (M+1), 566.0 (M−1).

Example 190

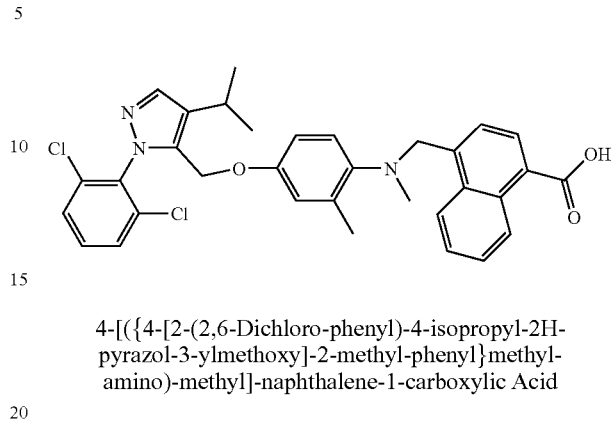

4-[({4-[2-(2,6-Dichloro-phenyl)-4-isopropyl-2H-pyrazol-3-ylmethoxy]-2-methyl-phenyl}methyl-amino)-methyl]-naphthalene-1-carboxylic Acid The title compound is prepared essentially according to the preparation of {4-[({4-[2-(2,6-Dichloro-phenyl)-4-isopropyl-2H-pyrazol-3-ylmethoxy]-2-methyl-phenyl}-methyl-amino)-methyl]-phenyl}-acetic acid using the appropriate starting material. LC-ES/MS m/e 588.3 (M+1), 586.0 (M−1)

The compounds listed in table 7 are prepared essentially according to the preparation of {4-[({4-[2-(2,6-Dichloro-phenyl)-4-isopropyl-2H-pyrazol-3-ylmethoxy]-2-methyl-phenyl}-methyl-amino)-methyl]-phenyl}-acetic acid using the appropriate starting material.

TABLE 7

| Ex | Chemical Name | Physical Data |
|---|---|---|
| 191 | 2-{4-[({4-[2-(2,6-Dichloro-phenyl)-4-isopropyl-2H-pyrazol-3-ylmethoxy]-2-methyl-phenyl}-methyl-amino)-methyl]-phenyl}-propionic acid | LC/MS (ES+): 566.3 |
| 192 | 4-[({4-[2-(2,6-Dichloro-phenyl)-4-isopropyl-2H-pyrazol-3-ylmethoxy]-2-methyl-phenyl}-methyl-amino)-methyl]-3-methoxy-benzoic acid | LC-MS: 568.0 (M + 1), 566.0 (M − 1) |
| 193 | 4-[({4-[2-(2,6-Dichloro-phenyl)-4-isopropyl-2H-pyrazol-3-ylmethoxy]-2-methyl-phenyl}-methyl-amino)-methyl]-3-fluoro-benzoic acid | LC-MS: 556.0 (M + 1), 554.0 (M − 1) |
| 194 | 4-[({4-[2-(2,6-Dichloro-phenyl)-4-isopropyl-2H-pyrazol-3-ylmethoxy]-2-methyl-phenyl}-methyl-amino)-methyl]-2-methoxy-benzoic acid | LC-MS: 568.0 (M + 1), 566.0 (M − 1) |
| 195 | 3-Bromo-4-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 618.0 (M + 1) |
| 196 | 4-[({4-[2-(2,6-Dichloro-phenyl)-4-isopropyl-2H-pyrazol-3-ylmethoxy]-2-methyl-phenyl}-methyl-amino)-methyl]-2-isopropoxy-benzoic acid | LC-MS: 596.0 (M + 1), 594.0 (M − 1) |
| 197 | 2-Butoxy-4-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 610.0 (M + 1), 608.0 (M − 1) |
| 198 | 4-[({4-[2-(2,6-Dichloro-phenyl)-4-isopropyl-2H-pyrazol-3-ylmethoxy]-2-methyl-phenyl}-methyl-amino)-methyl]-naphthalene-1-carboxylic acid | LC-MS: 588.3 (M + 1), 586.0 (M − 1) |
| 199 | 3-[({4-[2-(2,6-Dichloro-phenyl)-4-isopropyl-2H-pyrazol-3-ylmethoxy]-2-methyl-phenyl}-methyl-amino)-methyl]-5-methyl-benzoic acid | LC-MS: 552.3 (M + 1), 550.3 (M − 1) |
| 200 | 4-[({4-[2-(2,6-Dichloro-phenyl)-4-isopropyl-2H-pyrazol-3-ylmethoxy]-2-methyl-phenyl}-methyl-amino)-methyl]-2,3-difluoro-benzoic acid | LC-MS: 574.0 (M + 1), 572.3 (M − 1). |
| 201 | 4-[({4-[2-(2,6-Dichloro-phenyl)-4-isopropyl-2H-pyrazol-3-ylmethoxy]-2-methyl-phenyl}-methyl-amino)-methyl]-3-trifluoromethyl-benzoic acid | LC-MS: 606.0 (M + 1), 604.3 (M − 1). |
| 202 | 6-[({4-[2-(2,6-Dichloro-phenyl)-4-isopropyl-2H-pyrazol-3-ylmethoxy]-2-methyl-phenyl}-methyl-amino)-methyl]-nicotinic acid | LC-MS: 539.3 (M + 1), 537.3 (M − 1) |
| 203 | 4-[({4-[2-(2,6-Dichloro-phenyl)-4-isopropyl-2H-pyrazol-3-ylmethoxy]-2-methyl-phenyl}-methyl-amino)-methyl]-3-hydroxy-benzoic acid | LC-MS: 554.0 (M + 1), 552.0 (M − 1) |

TABLE 7-continued

| Ex | Chemical Name | Physical Data |
|---|---|---|
| 204 | 3-[({4-[2-(2,6-Dichloro-phenyl)-4-isopropyl-2H-pyrazol-3-ylmethoxy]-2-methyl-phenyl}-methyl-amino)-methyl]-4-fluoro-benzoic acid | %). LC-MS: 556.0 (M + 1), 554.0 (M − 1) |
| 205 | 2-Butoxy-5-[({4-[2-(2,6-dichloro-phenyl)-4-isopropyl-2H-pyrazol-3-ylmethoxy]-2-methyl-phenyl}-methyl-amino)-methyl]-benzoic acid | LC-MS: 610.0 (M + 1), 608.3 (M − 1) |
| 206 | 5-[({4-[2-(2,6-dichloro-phenyl)-4-isopropyl-2H-pyrazol-3-ylmethoxy]-2-methyl-phenyl}-methyl-amino)-methyl]-furan-2-carboxylic acid | LC-MS: 528.0 (M + 1), 526.0 (M − 1) |
| 207 | 4-[({4-[2-(2,6-Dichloro-phenyl)-4-isopropyl-2H-pyrazol-3-ylmethoxy]-2-methyl-phenyl}-methyl-amino)-methyl]-2-(propane-1-sulfonylamino)-benzoic acid | LC-ES/MS m/e 659.0 (M + 1), 657.0 (M − 1) |

Example 208

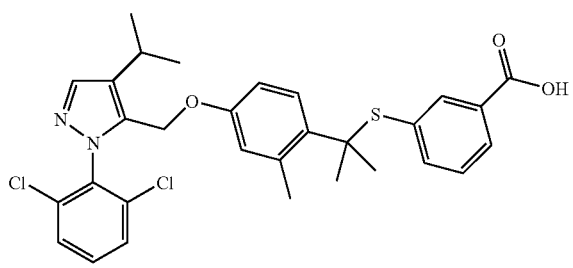

Step A 3-(1-{4-[2-(2,6-Dichloro-phenyl)-4-isopropyl-2H-pyrazol-3-ylmethoxy]-2-methyl-phenyl}-1-methyl-ethylsulfanyl)-benzoic Acid Methyl Ester To an ambient temperature solution of 2-{4-[2-(2,6-dichloro-phenyl)-4-isopropyl-2H-pyrazol-3-ylmethoxy]-2-methyl-phenyl}-propan-2-ol (100 mg, 0.230 mmol) in DCE (1 mL) is added zinc iodide (37 mg, 0.115 mmol). The reaction is stirred at room temperature for 10 min. A solution of methyl 4-mercaptobenzoate (38 mg, 0.225 mmol) in DCE (1 mL) is added and the reaction is stirred overnight at room temperature. The reaction is concentrated under reduced pressure and the residue is chromatographed (SiO$_2$ 40 g, 0% to 30% EtOAC/Hex) to yield the title compound (84 mg, 63%).

$^1$H NMR (400 MHz, CDCl$_3$) δ 7.74 (d, 2H, J=7.5 Hz), 7.71 (s, 1H), 7.44 (d, 2H, J=7.9 Hz), 7.37-7.30 (m, 1H), 7.03 (d, 2H, J=7.5 Hz), 6.89 (d, 1H, J=8.8 Hz), 6.61 (s, 1H), 6.41 (d, 1H, J=8.5 Hz), 4.81 (s, 2H), 3.89 (s, 3H), 3.02 (sept, 1H, J=6.6 Hz), 2.73 (s, 3H), 1.70 (s, 6H), 1.32 (d, 6H, J=6.6 Hz).

Step B 3-(1-{4-[2-(2,6-Dichloro-phenyl)-4-isopropyl-2H-pyrazol-3-ylmethoxy]-2-methyl-phenyl}-1-methyl-ethylsulfanyl)-benzoic Acid To an ambient temperature solution of 3-(1-{4-[2-(2,6-Dichloro-phenyl)-4-isopropyl-2H-pyrazol-3-ylmethoxy]-2-methyl-phenyl}-1-methyl-ethylsulfanyl)-benzoic acid methyl ester (91 mg, 0.156 mmol) in dioxane (2 mL) is added a solution of lithium hydroxide (234 μL, 0.468 mmol, 2.0N in water). The reaction mixture is heated to 50° C. The reaction mixture is concentrated and the residue is partitioned between Et$_2$O and water. The aqueous layer pH is adjusted to approximately 4 and is extracted with a second portion of Et$_2$O. The combined organic layers are washed with water, dried (MgSO$_4$), filtered, and concentrated to yield the title compound (84 mg, 95%). ES/MS m/e ($^{35}$Cl) 569.0 (M+1)

The compounds listed in table 8 are prepared essentially according to the preparation of 3-(1-{4-[2-(2,6-Dichloro-phenyl)-4-isopropyl-2H-pyrazol-3-ylmethoxy]-2-methyl-phenyl}-1-methyl-ethylsulfanyl)-benzoic acid using the appropriate starting material.

TABLE 8

| Ex | Chemical Name | Physical Data |
|---|---|---|
| 209 | 3-(1-{4-[2-(2,6-Dichloro-phenyl)-4-isopropyl-2H-pyrazol-3-ylmethoxy]-2-methyl-phenyl}-1-methyl-ethylsulfanyl)-benzoic acid | LC/MS (ES+): 569.0 |
| 210 | 4-(1-{4-[2-(2,6-Dichloro-phenyl)-4-isopropyl-2H-pyrazol-3-ylmethoxy]-2-methyl-phenyl}-1-methyl-ethylsulfanyl)-benzoic acid | LC/MS (ES+): 569.0, |
| 211 | [4-(1-{4-[2-(2,6-Dichloro-phenyl)-4-isopropyl-2H-pyrazol-3-ylmethoxy]-2-methyl-phenyl}-1-methyl-ethylsulfanyl)-phenyl]-acetic acid | LC/MS (ES+): 583.0, |
| 212 | [3-(1-{4-[2-(2,6-Dichloro-phenyl)-4-isopropyl-2H-pyrazol-3-ylmethoxy]-2-methyl-phenyl}-1-methyl-ethylsulfanyl)-phenyl]-acetic acid | LC/MS (ES+): 583.0, |
| 213 | 3-(1-{4-[4-Isopropyl-2-(2-trifluoromethoxy-phenyl)-2H-pyrazol-3-ylmethoxy]-2-methyl-phenyl}-1-methyl-ethylsulfanyl)-benzoic acid | LC/MS (ES+): 585.0 |
| 214 | 4-(1-{4-[4-Isopropyl-2-(2-trifluoromethoxy-phenyl)-2H-pyrazol-3-ylmethoxy]-2-methyl-phenyl}-1-methyl-ethylsulfanyl)-benzoic acid | LC/MS (ES+): 585.0 |
| 215 | [4-(1-{4-[4-Isopropyl-2-(2-trifluoromethoxy-phenyl)-2H-pyrazol-3-ylmethoxy]-2-methyl-phenyl}-1-methyl-ethylsulfanyl)-phenyl]-acetic acid | LC/MS (ES+): 599.0 |
| 216 | [3-(1-{4-[4-Isopropyl-2-(2-trifluoromethoxy-phenyl)-2H-pyrazol-3-ylmethoxy]-2-methyl-phenyl}-1-methyl-ethylsulfanyl)-phenyl]-acetic acid | LC/MS (ES+): 599.0 |

Example 217

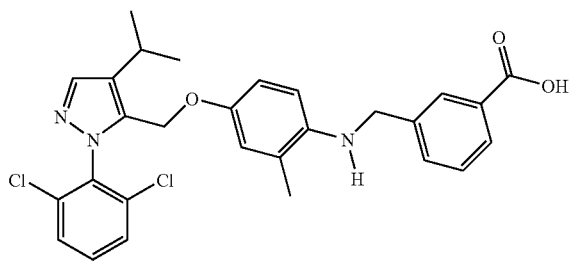

3-({4-[2-(2,6-Dichloro-phenyl)-4-isopropyl-2H-pyrazol-3-ylmethoxy]-2-methyl-phenylamino}-methyl)-benzoic Acid To a 0° C. solution of 3-[(tert-Butoxycarbonyl-{4-[2-(2,6-dichloro-phenyl)-4-isopropyl-2H-pyrazol-3-ylmethoxy]-2-methyl-phenyl}-amino)-methyl]-benzoic acid methyl ester (797 mg, 1.24 mmol) in dioxane (10 mL) is added hydrochloric acid (3.12 mL, 12.40 mmol, 4M in dioxane) dropwise. The reaction is warmed to room temperature and is stirred overnight. The reaction mixture is concentrated under reduced pressure and the residue is partitioned between EtOAc and saturated aqueous $NaHCO_3$. The aqueous layer is extracted with EtOAc and the combined organic layers are washed with brine, dried ($MgSO_4$), filtered, and concentrated under reduced pressure. The residue is chromatographed ($SiO_2$ 120 g, 0% to 30% EtOAc/Hex) to yield the title compound (603 mg, 90%). ES/MS m/e ($^{35}Cl$) 524.0 (M+1)

Example 218

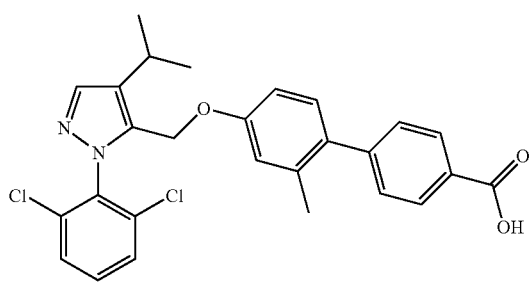

4'-[2-(2,6-Dichloro-phenyl)-4-isopropyl-2H-pyrazol-3-ylmethoxy]-2'-methyl-biphenyl-4-carboxylic Acid The title compound is prepared essentially as described in the preparation of 3-({4-[2-(2,6-Dichloro-phenyl)-4-isopropyl-2H-pyrazol-3-ylmethoxy]-2-methyl-phenylamino}-methyl)-benzoic acid using the appropriate starting material. LC-MS: 495 (M+1)

Example 219

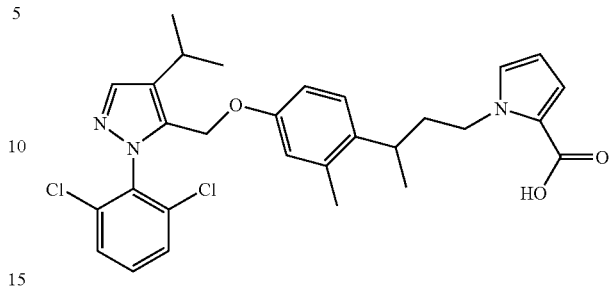

(+/−)-1-(3-{4-[2-(2,6-Dichloro-phenyl)-4-isopropyl-2H-pyrazol-3-ylmethoxy]-2-methyl-phenyl}-butyl)-1H-pyrrole-2-carboxylic Acid

Step A

To a solution of methylpyrrole-2-carboxylate in dimethylformamide (3 mL) is added cesium carbonate (0.119 g, 0.366 mmol) followed by (+/−)-3-nitro-benzenesulfonic acid 3-{4-[2-(2,6-dichloro-phenyl)-4-isopropyl-2H-pyrazol-3-ylmethoxy]-2-methyl-phenyl}-butyl ester (0.116 g, 0.183 mmol). The reaction mixture is heated to 75° C. overnight. The reaction is quenched with water followed by 1N HCl. The resulting solution is extracted two times with ethyl acetate. The organic layers are combined, washed with brine, dried over magnesium sulfate, filtered and concentrated under reduced pressure. The residue is purified via flash chromatography eluting with 0-3% ethyl acetate:toluene to give the methyl ester.

Step B

To a solution of the methyl ester from Step A (12 mg, 1 equiv.) in methanol is added 1 N NaOH (0.11 mL, 5 equiv.). The reaction heated to reflux for 3 hours. The reaction is concentrated under reduced pressure and the residue dissolved in water. 1 N HCl is added and the precipitated product is isolated via filtration, (7 mg, 58%). ES/MS m/e: 539.8 (M+0), 541.8 (M+2).

Example 220

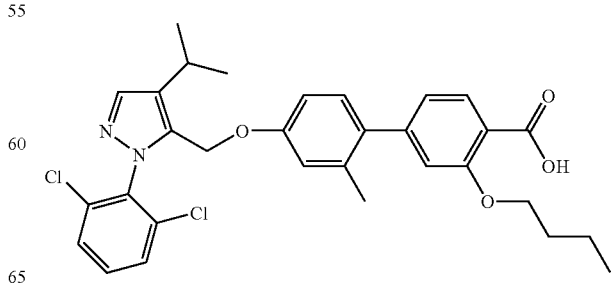

3-Butoxy-4'-[2-(2,6-dichloro-phenyl)-4-isopropyl-2H-pyrazol-3-ylmethoxy]-2'-methyl-biphenyl-4-carboxylic Acid Step A A solution of 3-butoxy-4'-hydroxy-2'-methyl-biphenyl-4-carbaldehyde (0.198 g, 0.696 mmol) and 5-bromomethyl-4-isopropyl-1-(2,6-dichloro-phenyl)-1H-pyrazole (0.242 g, 0.696 mmol) in DMF (2.0 mL) is treated with $K_2CO_3$ (0.192 g, 1.39 mmol). The mixture is stirred at 70° C. for 2 hours. The mixture is cooled to room temperature and quenched with water (10 mL). The mixture is extracted with ethyl acetate (20 mL×2), and the combined organic layers are dried over sodium sulfate and concentrated under reduced pressure. The residue is purified by silica gel chromatography eluting with 20% ethyl acetate in hexanes to give 3-butoxy-4'-[2-(2,6-dichloro-phenyl)-4-isopropyl-2H-pyrazol-3-ylmethoxy]-2'-methyl-biphenyl-4-carbaldehyde (0.125 g, 33%). ES/MS m/e 551.0; 553.0 (M+1).

Step B

A solution of 3-butoxy-4'-[2-(2,6-dichloro-phenyl)-4-isopropyl-2H-pyrazol-3-ylmethoxy]-2'-methyl-biphenyl-4-carbaldehyde (0.125 g, 0.227 mmol) in t-BuOH (2.0 mL) and 2-methyl-2-butene (1.0 mL) at 0° C. is treated with a solution of $NaClO_2$ (205 mg, 2.27 mmol) and $NaH_2PO_4$—$H_2O$ (313 mg, 2.27 mmol) in water (2.0 mL). The mixture is stirred at 0° C. for 60 minutes. The organic layer is separated, dried over sodium sulfate, and concentrated under reduced pressure. The residue is purified using silica gel chromatography eluting with 50%-100% ethyl acetate in hexanes to give the title compound (0.120 g, 93%). ES/MS m/e 566.8; 568.7 (M+1).

Example 221

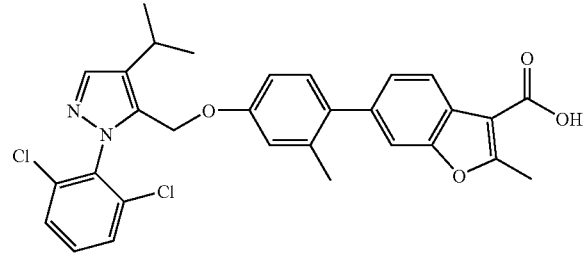

6-{4-[2-(2,6-Dichloro-phenyl)-4-isopropyl-2H-pyrazol-3-ylmethoxy]-2-methyl-phenyl}-2-methyl-benzofuran-3-carboxylic Acid Step A A solution of 4-bromo-3-methyl-phenol (135 mg, 0.723 mmol) and 5-bromomethyl-1-(2,6-dichloro-phenyl)-4-isopropyl-1H-pyrazole (210 mg, 0.603 mmol) in dimethylformamide (1.0 mL) is treated with potassium carbonate (84 mg, 0.603 mmol). The reaction mixture is heated at 80° C. for 60 minutes and cooled to room temperature. The mixture is loaded directly onto a silica gel column and purified with 25% EtOAc/Hexanes to provide 5-(4-bromo-3-methyl-phenoxymethyl)-1-(2,6-dichloro-phenyl)-4-isopropyl-1H-pyrazole (0.258 g, 94%). ES/MS m/e (M+1) 454.8.

Step B

A solution of 2-methyl-6-(4,4,5,5-tetramethyl-[1,3,2]dioxaborolan-2-yl)-benzofuran-3-carboxylic acid methyl ester (162 mg, 0.512 mmol) and 5-(4-bromo-3-methyl-phenoxymethyl)-1-(2,6-dichloro-phenyl)-4-isopropyl-1H-pyrazole (256 mg, 0.563 mmol) in toluene (5 mL) is evacuated and refilled with $N_2$ three times. $Pd(OAc)_2$ (11.5 mg, 0.051 mmol), 2-dicyclohexylphosphino-2,6-dimethoxy-1,1'-biphenyl (42 mg, 0.102 mmol), and potassium phosphate (tribasic, N-hydrate, 218 mg, 1.02 mmol) in 0.5 mL of water are added. The resulting mixture is evacuated and refilled with $N_2$ three times. The mixture is stirred at 110° C. for 16 hours and cooled to room temperature. The mixture is filtered through a pad of celite, and the filtrate is concentrated. The residue is purified by silica gel chromatography with 25% EtOAc/Hexanes to provide the product 6-{4-[2-(2,6-dichloro-phenyl)-4-isopropyl-2H-pyrazol-3-ylmethoxy]-2-methyl-phenyl}-2-methyl-benzofuran-3-carboxylic acid methyl ester (89 mg, 31%). ES/MS m/e 564.8 (M+1).

Step C

The title compound is prepared by hydrolysis from the ester according to the preparation of 3-(2-{4-[4-Isopropyl-2-(2-trifluoromethyl-phenyl)-2H-pyrazol-3-ylmethoxy]-2-methyl-phenyl}-vinyl)-benzoic acid (Example 1) using the appropriate starting material.
LC-MS: 550.8; 548.8 (M+1).

Example 222

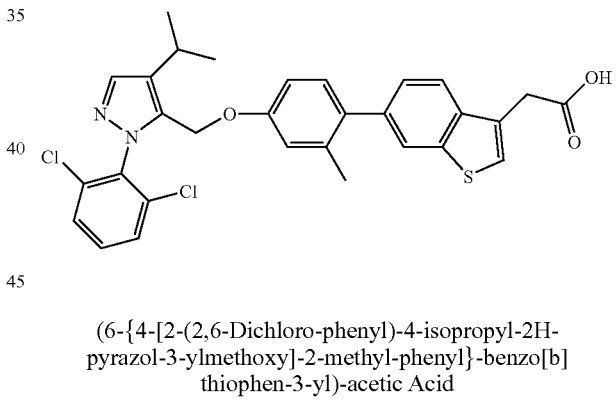

(6-{4-[2-(2,6-Dichloro-phenyl)-4-isopropyl-2H-pyrazol-3-ylmethoxy]-2-methyl-phenyl}-benzo[b]thiophen-3-yl)-acetic Acid Step A A solution of [6-(4,4,5,5-tetramethyl-[1,3,2]dioxaborolan-2-yl)-benzo[b]thiophen-3-yl]-acetic acid ethyl ester (267 mg, 0.770 mmol) and 5-(4-bromo-3-methyl-phenoxymethyl)-1-(2,6-dichloro-phenyl)-4-isopropyl-1H-pyrazole (280 mg, 0.616 mmol) in toluene (10 mL) is evacuated and refilled with $N_2$ three times. $Pd(OAc)_2$ (5.5 mg, 0.024 mmol), 2-dicyclohexylphosphino-2,6-dimethoxy-1,1'-biphenyl (20 mg, 0.049 mmol), and potassium phosphate, tribasic, N-hydrate (262 mg, 1.23 mmol) are added. The mixture is stirred at 100° C. for 15 hours. The reaction mixture is cooled to room temperature and filtered through a pad of celite. The filtrate is concentrated, and the residue is purified by flash chromatography (eluted with 25% EtOAc/Hexanes) and the appropriate fractions are concentrated. The material is dried in vacuo to afford (6-{4-[2-(2,6-dichloro-phenyl)-4-isopropyl-2H-pyrazol-3- ylmethoxy]-2-methyl-phenyl}-benzo[b]thiophen-3-yl)-acetic acid ethyl ester (43 mg, 12% yield). ES/MS m/e 592.8; 594.8 (M+1).

Step B

A solution of (6-{4-[2-(2,6-dichloro-phenyl)-4-isopropyl-2H-pyrazol-3-ylmethoxy]-2-methyl-phenyl}-benzo[b]thiophen-3-yl)-acetic acid ethyl ester (43 mg; 0.072 mmoles) in tetrahydrofuran (1.0 mL) and methanol (1.0 mL) is treated with sodium hydroxide (1.0 mL; 1.0 N). The mixture is stirred at room temperature for 2 hours and quenched with HCl (1.0 mL, 1.0 M). The mixture is extracted with EtOAc (10 mL×2). The combined organic layers are dried over $Na_2SO_4$, filtered and concentrated. The crude product is purified by flash chromatography (eluting with 30-100% EtOAc/Hexanes) and the appropriate fractions are concentrated. The material is dried in vacuo to afford the title compound (28 mg, 68%). ES/MS m/e 564.8; 566.8 (M+1); 562.8; 564.8 (M−1)

Example 223

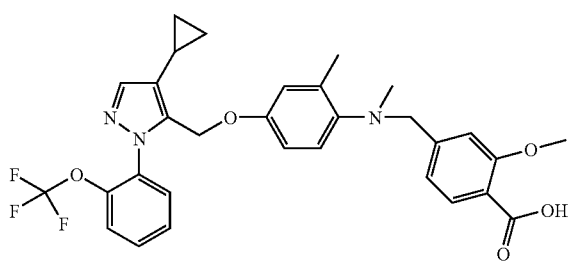

4-[({4-[4-Cyclopropyl-2-(2-trifluoromethoxy-phenyl)-2H-pyrazol-3-ylmethoxy]-2-methyl-phenyl}-methyl-amino)-methyl]-2-methoxy-benzoic Acid Step A Sodium hydride (60% in mineral oil, 30 mg, 0.75 mmol) is added to a solution of {4-[4-cyclopropyl-2-(2-trifluoromethoxy-phenyl)-2H-pyrazol-3-ylmethoxy]-2-methyl-phenyl}-methyl-amine (0.31 g, 0.75 mmol) and 4-bromomethyl-2-methoxy-benzoic acid methyl ester (0.320 g, 1.23 mmol) in DMF (3 mL) at room temperature. The reaction is heated to 40° C. for 2 h. The mixture is diluted with water and is extracted with ethyl acetate. The combined organic layers are washed with brine and dried over $MgSO_4$. The crude residue is purified via radial chromatography (2 mm plate, 20 to 40 THF-heptane) to afford 4-[({4-[4-cyclopropyl-2-(2-trifluoromethoxy-phenyl)-2H-pyrazol-3-ylmethoxy]-2-methyl-phenyl}-methyl-amino)-methyl]-2-methoxy-benzoic acid methyl ester (303 mg, 68%). ES/MS m/e 596.0 (M+1).

Step B

A mixture of 4-[({4-[4-cyclopropyl-2-(2-trifluoromethoxy-phenyl)-2H-pyrazol-3-ylmethoxy]-2-methyl-phenyl}-methyl-amino)-methyl]-2-methoxy-benzoic acid methyl ester (0.30 g, 0.51 mmol), sodium hydroxide (5 N, 0.5 mL), THF (3 mL) and methanol (3 mL) is heated to reflux for 1 h. The reaction is cooled and acidified with 5 N HCl, then diluted with water and extracted with ethyl acetate. The combined organic layers are washed with brine and dried over $MgSO_4$ to give the tile compound (285 mg, 97%) as an off-white foam. LC-ES/MS m/e 582.0 (M+1).

Example 224

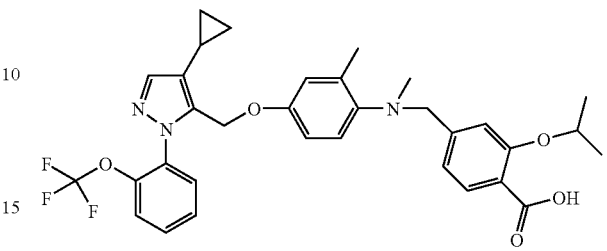

4-[({4-[4-Cyclopropyl-2-(2-trifluoromethoxy-phenyl)-2H-pyrazol-3-ylmethoxy]-2-methyl-phenyl}-methyl-amino)-methyl]-2-isopropoxy-benzoic Acid Step A In a manner similar to the preparation of 4-[({4-[4-cyclopropyl-2-(2-trifluoromethoxy-phenyl)-2H-pyrazol-3-ylmethoxy]-2-methyl-phenyl}-methyl-amino)-methyl]-2-methoxy-benzoic acid methyl ester, utilizing {4-[4-cyclopropyl-2-(2-trifluoromethoxy-phenyl)-2H-pyrazol-3-ylmethoxy]-2-methyl-phenyl}-methyl-amine and 4-bromomethyl-2-isopropoxy-benzoic acid methyl ester, 4-[({4-[4-Cyclopropyl-2-(2-trifluoromethoxy-phenyl)-2H-pyrazol-3-ylmethoxy]-2-methyl-phenyl}-methyl-amino)-methyl]-2-isopropoxy-benzoic acid methyl ester is prepared. ES/MS m/e 624.0 (M+1).

Step B

In a manner similar to the preparation of 4-[({4-[4-cyclopropyl-2-(2-trifluoromethoxy-phenyl)-2H-pyrazol-3-ylmethoxy]-2-methyl-phenyl}-methyl-amino)-methyl]-2-methoxy-benzoic acid, utilizing 4-[({4-[4-cyclopropyl-2-(2-trifluoromethoxy-phenyl)-2H-pyrazol-3-ylmethoxy]-2-methyl-phenyl}-methyl-amino)-methyl]-2-isopropoxy-benzoic acid methyl ester, the title compound is prepared. LC-ES/MS m/e 610.2 (M+1).

We claim:
1. A compound of formula

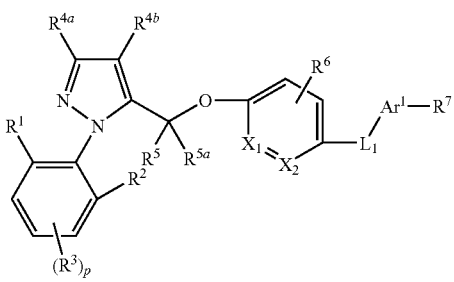

p is 0 or 1 or 2;
$X_1$ is C or N and $X_2$ is C or N; provided that both $X_1$ and $X_2$ are not N;

$R^1$ and $R^2$ are independently selected from the group consisting of hydrogen, $C_1$-$C_6$ alkyl, $C_1$-$C_6$ haloalkyl, $C_1$-$C_6$ alkoxy, $C_1$-$C_6$ haloalkoxy, halo, —S$C_1$-$C_6$ alkyl, and —S—$C_1$-$C_3$ haloalkyl;

each $R^3$ is independently selected from the group consisting of hydrogen, $C_1$-$C_6$ alkyl, $C_1$-$C_6$ haloalkyl, $C_1$-$C_6$ alkoxy, $C_1$-$C_6$ haloalkoxy, and halo;

$R^{4a}$ is selected from the group consisting of hydrogen, $C_1$-$C_6$ alkyl, $C_1$-$C_6$ haloalkyl, $C_3$-$C_8$ cycloalkyl, $C_4$-$C_8$ alkylcycloalkyl, $C_1$-$C_6$ alkoxy, and $C_1$-$C_6$ haloalkoxy;

$R^{4b}$ is selected from the group consisting of hydrogen, $C_1$-$C_6$ alkyl, $C_1$-$C_6$ haloalkyl, $C_3$-$C_8$ cycloalkyl, $C_4$-$C_8$ alkylcycloalkyl, $C_1$-$C_6$ alkoxy, and $C_1$-$C_6$ haloalkoxy;

$R^5$ and $R^{5a}$ are independently selected from the group consisting of hydrogen, and $C_1$-$C_3$ alkyl;

$R^6$ is selected from the group consisting of hydrogen, $C_1$-$C_6$ alkyl, $C_1$-$C_6$ haloalkyl, halo, $C_1$-$C_6$ alkoxy, $C_1$-$C_6$ haloalkoxy, $NO_2$, $C_3$-$C_8$ cycloalkyl, and $C_4$-$C_8$ alkylcycloalkyl;

$L_1$ is selected from the group consisting of a bond, $C_1$-$C_6$ alkyl, $CR^a$=$CR^b$, ethynyl, $C_1$-$C_5$ alkylene, $C_1$-$C_5$ alkyl-S—, $C_1$-$C_5$ alkyl-O—, $N(R^c)$—$C_1$-$C_5$ alkyl, and —$C_1$-$C_5$ alkyl-$N(R^c)$—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl and $C_4$-$C_8$ alkylcycloalkyl;

$Ar^1$ is selected from the group consisting of indolyl, thienyl, benzothienyl, naphthyl, phenyl, pyridinyl, pyrazolyl, oxazolyl, benzoisoxazolyl, benzofuranyl, pyrrolyl, thiazolyl, benzoisothiazolyl, indazolyl, and furanyl, each optionally substituted with one or two groups independently selected from the group consisting of hydroxy, $C_1$-$C_6$ alkyl, $C_1$-$C_6$ haloalkyl, halo, $C_2$-$C_6$ alkenyl, $C_2$-$C_6$ alkynyl, $C_1$-$C_6$ alkoxy, —O$C_1$-$C_2$ alkylphenyl, $N(R^c)SO_2C_1$-$C_6$ alkyl, —$C(O)R^{10}$, and NHC(O)$R^{10}$;

$R^7$ is selected from the group consisting of COOH, $C_1$-$C_5$ alkylCOOH, —O—$C_1$-$C_5$ alkylCOOH, $C_2$-$C_4$ alkenylCOOH, $C_3$-$C_8$ cycloalkylCOOH, and $CONR^{11}R^{11}$;

each $R^{10}$ is independently selected from the group consisting of hydrogen, $C_1$-$C_6$ alkyl, and phenyl;

each $R^{11}$ is independently hydrogen, or $C_1$-$C_6$ alkyl; or a pharmaceutically acceptable salt thereof.

2. A compound of according to claim 1 wherein
p is 0 or 1 or 2;
$X_1$ is C or N and $X_2$ is C or N; provided that both $X_1$ and $X_2$ are not N;
$R^1$ and $R^2$ are independently selected from the group consisting of hydrogen, $C_1$-$C_3$ alkyl, $C_1$-$C_3$ haloalkyl, $C_1$-$C_3$ thiohaloalkyl, $C_1$-$C_3$ alkoxy, $C_1$-$C_3$ haloalkoxy, and halo;
$R^3$ is absent or independently selected from the group consisting of $C_1$-$C_3$ alkyl, $C_1$-$C_3$ haloalkyl, $C_1$-$C_3$ alkoxy, $C_1$-$C_3$ haloalkoxy, and halo;
$R^{4a}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;
$R^{4b}$ is selected from the group consisting of hydrogen, $C_1$-$C_3$ alkyl, $C_1$-$C_3$ haloalkyl, $C_3$-$C_6$ cycloalkyl, and $C_4$-$C_5$ alkylcycloalkyl;
$R^5$ and $R^{5a}$ are independently selected from the group consisting of hydrogen and $C_1$-$C_3$ alkyl;
$R^6$ is selected from the group consisting of hydrogen, $C_1$-$C_3$ alkyl, $C_1$-$C_3$ haloalkyl, halo, and —$NO_2$;
$L_1$ is selected from the group consisting of a bond, $CR^a$=$CR^b$, ethynyl, $C_1$-$C_3$ alkyl-S—, $C_1$-$C_3$ alkyl-O—, $N(R^c)$—$C_1$-$C_3$ alkyl, and —$C_1$-$C_3$ alkyl-$N(R^c)$—, wherein $R^a$ and $R^b$ are independently selected from the group consisting of hydrogen and $C_1$-$C_3$ alkyl; and $R^c$ is independently selected from the group consisting of H, $C_1$-$C_5$ alkyl, $C_1$-$C_3$ alkylphenyl, and $C_4$-$C_8$ alkylcycloalkyl;

$Ar^1$ is selected from the group consisting of indolyl, benzothienyl, benzoisothiazolyl, indazolyl, naphthyl, phenyl, pyridinyl, pyrazolyl, pyrrolyl, thienyl, thiazolyl, and furanyl, each optionally substituted with one or two groups independently selected from the group consisting of hydroxy, $C_1$-$C_3$ alkyl, $C_1$-$C_3$ haloalkyl, halo, $C_2$-$C_4$ alkenyl, $C_2$-$C_4$ alkynyl, $C_1$-$C_4$ alkoxy, —O$C_1$-$C_2$ alkylphenyl, —$NHC(O)R^{10}$;

$R^7$ is selected from the group consisting of —COOH, —$C_1$-$C_3$ alkylCOOH, —O—$C_1$-$C_3$ alkylCOOH, and, —$CONR^{11}R^{11}$;

each $R^{10}$ is independently selected from the group consisting of hydrogen, $C_1$-$C_3$ alkyl, and phenyl;

each $R^{11}$ is independently hydrogen, or $C_1$-$C_5$ alkyl; or a pharmaceutically acceptable salt thereof.

3. A compound according to claim 1 wherein
p is 0 or 1;
$X_1$ and $X_2$ are both C, or $X_1$ is N and $X_2$ is C;
$R^1$ and $R^2$ are independently selected from the group consisting of hydrogen, fluoro, chloro, $CF_3$, $SCF_3$, $OCF_3$,
$R^3$ is fluoro, chloro $C_1$-$C_3$ alkyl, $CF_3$, $SCF_3$, or $OCF_3$;
$R^{4a}$ is hydrogen, methyl, ethyl or isopropyl or cyclopropyl;
$R^{4b}$ is H, $C_1$-$C_3$ alkyl, $C_1$-$C_3$ haloalkyl, $C_1$-$C_3$ haloalkoxy, or $C_3$-$C_4$ cycloalkyl;
$R^5$ and $R^{5a}$ are each independently selected from H or $C_1$-$C_3$ alkyl;
$Ar^1$ group is phenyl, indolyl, pyridinyl, pyrrolyl, thienyl, naphthyl, thiazolyl, furanyl, pyrazolyl, indazolyl, benzoisothiazolyl, and benzothienyl each optionally substituted with one to two groups independently selected from $C_1$-$C_5$ alkyl, $C_1$-$C_3$ alkoxy, $C_1$-$C_2$ haloalkoxy, and $C_1$-$C_3$ haloalkyl;
$R^6$ is hydrogen, methyl, ethyl or chloro;
$L_1$ is a bond, ethenyl, —$CH(CH_3)$—S—, $C(CH_3)_2$—S—, —$CH_2O$—, —$CH_2CH_2O$—, —$CH(CH_3)$—O—, —$CH(CH_3)CH_2$—O—, —$CH(CH_2CH_3)$—O—, —$CH_2NH$—, —$CH_2CH_2NH$—, —$N(R^c)CH_2$—, $N(R^c)CH_2CH_2$—, or $N(R^c)CH_2CH_2CH_2$—; wherein $R^c$ is hydrogen, $C_1$-$C_2$ alkyl, benzyl or —$CH_2CH_2$—O—$CH_2$—;
$R^7$ is COOH, —$CH_2COOH$, —$CH(CH_3)COOH$, -cyclopropylCOOH, —$C(CH_3)_2COOH$, $CONH_2$, $C(O)NHCH_3$, or $C(O)NHCH_2CH_3$;
$R^{10}$ is hydrogen or $C_1$-$C_2$ alkyl; and
$R^{11}$ is hydrogen or $C_1$-$C_2$ alkyl.

4. A compound according to claim 1, wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is ethenyl, ethynyl, —$N(CH_3)CH_2$—, or —$N(CH_3)CH_2CH_2$—; $R^5$ and $R^{5a}$ are both hydrogen; $R^6$ is hydrogen, methyl, chloro or bromo; $Ar^1$ is phenyl, indolyl, indazolyl, benzothienyl, or benzoisothiazolyl, each optionally substituted with a group selected from methyl, ethyl, propyl, isopropyl, cyclopropyl, methoxy, ethoxy, isopropoxy and cyclopropoxy; and $R^7$ is COOH.

5. A compound according to claim 1, wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

6. A compound according to claim 1, wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, optionally substituted with a group selected from methyl, ethyl, propyl, isopropyl, cyclopropyl, methoxy, ethoxy, isopropoxy and cyclopropoxy; and $R^7$ is COOH.

7. A compound according to claim 1, wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond, —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

8. A compound according to claim 2, wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

9. A compound according to claim 2, wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond; $R^5$ and $R^{5a}$ are both hydrogen; $R^6$ is hydrogen, methyl, ethyl or chloro; $Ar^1$ is phenyl, benzoisothiazolyl, indazolyl, indolyl or benzothienyl, each optionally substituted with a group selected from methyl, ethyl, propyl, isopropyl, cyclopropyl, methoxy, ethoxy, isopropoxy and cyclopropoxy; and $R^7$ is COOH.

10. A compound according to claim 2, wherein $X_1$ and $X_2$ are both C; p is 0; $R^1$ and $R^2$ are independently selected from the group consisting of hydrogen, chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is a bond; $R^5$ and $R^{4a}$ are both hydrogen; $R^6$ is hydrogen, methyl, ethyl or chloro; $Ar^1$ is phenyl optionally substituted with a group selected from methyl, ethyl, propyl, isopropyl, cyclopropyl, methoxy, ethoxy, isopropoxy and cyclopropoxy; and $R^7$ is COOH.

11. A compound according to claim 2, wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^{4a}$ is hydrogen; $R^{4b}$ is trifluoromethyl, isopropyl or cyclopropyl; $L_1$ is ethenyl; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

12. A compound according to claim 1, wherein $X_1$ and $X_2$ are both C; p is 0; $R^1$ and $R^2$ are independently selected from the group consisting of chloro, fluoro, trifluoromethyl, thiotrifluoromethyl, and trifluoromethoxy; $R^3$ is hydrogen; $R^{4a}$ is hydrogen; $R^{4b}$ is trifluoromethyl, isopropyl or cyclopropyl; $L_1$ is ethenyl, —N(CH$_3$)CH$_2$—, or —N(CH$_3$)CH$_2$CH$_2$—; $R^5$ and $R^{5a}$ are both hydrogen; $R^6$ is hydrogen, methyl, ethyl or chloro; $Ar^1$ is phenyl, thienyl, pyrrolyl, furanyl, or thiazolyl, each optionally substituted with a group selected from methyl, ethyl, propyl, isopropyl, cyclopropyl, methoxy, ethoxy, isopropoxy and cyclopropoxy; and $R^7$ is COOH.

13. A compound selected from the group consisting of:
- 4-[({4-[2-(2,6-Dichloro-phenyl)-4-isopropyl-2H-pyrazol-3-ylmethoxy]-2-methyl-phenyl}-methyl-amino)-methyl]-2-methoxy-benzoic acid,
- 4-[({4-[2-(2,6-Dichloro-phenyl)-4-isopropyl-2H-pyrazol-3-ylmethoxy]-2-methyl-phenyl}-methyl-amino)-methyl]-2-methyl-benzoic acid,
- 4-[({4-[2-(2,6-Dichloro-phenyl)-4-isopropyl-2H-pyrazol-3-ylmethoxy]-2-methyl-phenyl}-methyl-amino)-methyl]-2-isopropoxy-benzoic acid,
- 2-Butoxy-4-[({4-[2-(2,6-dichloro-phenyl)-4-isopropyl-2H-pyrazol-3-ylmethoxy]-2-methyl-phenyl}-methyl-amino)-methyl]-benzoic acid,
- 2-Benzyloxy-4-[({4-[2-(2,6-dichloro-phenyl)-4-isopropyl-2H-pyrazol-3-ylmethoxy]-2-methyl-phenyl}-methyl-amino)-methyl]-benzoic acid,
- 4-[({4-[2-(2,6-Dichloro-phenyl)-4-isopropyl-2H-pyrazol-3-ylmethoxy]-2-methyl-phenyl}-methyl-amino)-methyl]-naphthalene-1-carboxylic acid,
- 4-[({4-[2-(2,6-Dichloro-phenyl)-4-isopropyl-2H-pyrazol-3-ylmethoxy]-2-methyl-phenyl}-methyl-amino)-methyl]-2-pentyl-benzoic acid,
- 3-[({4-[2-(2,6-Dichloro-phenyl)-4-isopropyl-2H-pyrazol-3-ylmethoxy]-2-methyl-phenyl}-methyl-amino)-methyl]-5-methyl-benzoic acid,
- 2-Butyrylamino-4-[({4-[2-(2,6-dichloro-phenyl)-4-isopropyl-2H-pyrazol-3-ylmethoxy]-2-methyl-phenyl}-methyl-amino)-methyl]-benzoic acid,
- 4-[({4-[2-(2,6-Dichloro-phenyl)-4-isopropyl-2H-pyrazol-3-ylmethoxy]-2-methyl-phenyl}-methyl-amino)-methyl]-2-trifluoromethyl-benzoic acid,
- 3-[({4-[2-(2,6-Dichloro-phenyl)-4-isopropyl-2H-pyrazol-3-ylmethoxy]-2-methyl-phenyl}-methyl-amino)-methyl]-5-trifluoromethyl-benzoic acid,
- 4-[({4-[2-(2,6-Dichloro-phenyl)-4-isopropyl-2H-pyrazol-3-ylmethoxy]-2-methyl-phenyl}-methyl-amino)-methyl]-3-hydroxy-benzoic acid,
- 5-[({4-[2-(2,6-Dichloro-phenyl)-4-isopropyl-2H-pyrazol-3-ylmethoxy]-2-methyl-phenyl}-methyl-amino)-methyl]-2-fluoro-benzoic acid,
- 3-[({4-[2-(2,6-Dichloro-phenyl)-4-isopropyl-2H-pyrazol-3-ylmethoxy]-2-methyl-phenyl}-methyl-amino)-methyl]-4-fluoro-benzoic acid,
- 3-[({4-[2-(2,6-Dichloro-phenyl)-4-isopropyl-2H-pyrazol-3-ylmethoxy]-2-methyl-phenyl}-methyl-amino)-methyl]-4-methoxy-benzoic acid,
- 2-Butoxy-5-[({4-[2-(2,6-dichloro-phenyl)-4-isopropyl-2H-pyrazol-3-ylmethoxy]-2-methyl-phenyl}-methyl-amino)-methyl]-benzoic acid,
- 3-Butoxy-5-[({4-[2-(2,6-dichloro-phenyl)-4-isopropyl-2H-pyrazol-3-ylmethoxy]-2-methyl-phenyl}-methyl-amino)-methyl]-benzoic acid, 3-[({4-[4-Cyclopropyl-2-(2,6-dichloro-phenyl)-2H-pyrazol-3-ylmethoxy]-phenyl}methyl-amino)-methyl]-benzoic acid, 4-[({-4-[4-Isopropyl-2-(2-trifluoromethoxy-phenyl)-2H-pyrazol-3-ylmethoxy]-2-methyl-phenyl}-methyl-amino)-methyl]-benzoic acid, 4-[({4-[2-(2,6-Dichloro-phenyl)-4-isopropyl-2H-pyrazol-3-ylmethoxy]-2-methyl-phenyl}-methyl-amino)-methyl]-benzoic acid, 3-[({4-[2-(2,6-Dichloro-phenyl)-4-isopropyl-2H-pyrazol-3-ylmethoxy]-2-methyl-phenyl}-methyl-amino)-methyl]-benzoic acid, 3-[({-4-[Isopropyl-2-(2-trifluoromethoxy-phenyl)-2H-pyrazol-3-ylmethoxy]-2-methyl-phenyl}-methyl-amino)-methyl]-benzoic acid, 4-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic acid, 3-[({6-[4-Isopropyl-2-(2-trifluoromethoxy-phenyl)-2H-pyrazol-3-ylmethoxy]-2-methyl-pyridin-3-yl}-methyl-amino)-methyl]-benzoic acid, 5-[({6-[4-Isopropyl-2-(2-trifluoromethoxy-phenyl)-2H-pyrazol-3-ylmethoxy]-2-methyl-pyridin-3-yl}-methyl-amino)-methyl]-2-methoxy-benzoic acid, 4-[({6-[4-Isopropyl-2-(2-trifluoromethoxy-phenyl)-2H-pyrazol-3-ylmethoxy]-2-methyl-pyridin-3-yl}-methyl-amino)-methyl]-2-pentyl-benzoic acid, 4-[({6-[4-Isopropyl-2-(2-trifluoromethoxy-phenyl)-2H-pyrazol-3-ylmethoxy]-2-methyl-pyridin-3-yl}-methyl-amino)-methyl]-2-methyl-benzoic acid, 6-{4-[4-Isopropyl-2-(2-trifluoromethoxy-phenyl)-2H-pyrazol-3-ylmethoxy]-2-methyl-phenyl}-1-methyl-1H-indole-3-carboxylic acid, 6-{4-[4-Isopropyl-2-(2-trifluoromethoxy-phenyl)-2H-pyrazol-3-ylmethoxy]-2-methyl-phenyl}-benzo[b]thiophene-3-carboxylic acid, 5-{4-[2-(2,6-Dichloro-phenyl)-4-isopropyl-2H-pyrazol-3-ylmethoxy]-2-methyl-phenyl}-thiophene-2-carboxylic acid, 5-{4-[4-Isopropyl-2-(2-trifluoromethoxy-phenyl)-2H-pyrazol-3-ylmethoxy]-2-methyl-phenyl}-thiophene-2-carboxylic acid, 2-{4-[4-Isopropyl-2-(2-trifluoromethoxy-phenyl)-2H-pyrazol-3-ylmethoxy]-2-methyl-phenyl}-4-methyl-thiazole-5-carboxylic acid, 6-[({4-[2-(2,6-Dichloro-phenyl)-4-isopropyl-2H-pyrazol-3-ylmethoxy]-2-methyl-phenyl}-methyl-amino)-methyl]-nicotinic acid, 4-[({4-[4-Isopropyl-2-(2-trifluoromethoxy-phenyl)-2H-pyrazol-3-ylmethoxy]-2-methyl-phenyl}-methyl-amino)-methyl]-2-methyl-benzoic acid, 3-[({-4-[2-(2,6-Dichloro-phenyl)-4-isopropyl-2H-pyrazol-3-ylmethoxy]-2-methyl-phenyl}-ethyl-amino)-methyl]-benzoic acid, and a pharmaceutically acceptable salt, enantiomer or diastereomer thereof.

14. The compound 2-[2-({4-[2-(2,6-Dichloro-phenyl)-4-isopropyl-2H-pyrazol-3-ylmethoxy]-2-methyl-phenyl}-methyl-amino)-ethyl]-5-methyl-benzoic acid.

15. The compound 3-[({4-[2-(2,6-Dichloro-phenyl)-4-isopropyl-2H-pyrazol-3-ylmethoxy]-2-methyl-phenyl}-methyl-amino)-methyl]-5-methyl-benzoic acid.

16. The compound-[({4-[2-(2,6-Dichloro-phenyl)-4-isopropyl-2H-pyrazol-3-ylmethoxy]-2-methyl-phenyl}-ethyl-amino)-methyl]-benzoic acid.

17. A method of treating dyslipidemia comprising administering a therapeutically effective amount of a compound according to claim 1 to a patient in need thereof.

18. A method of treating atherosclerosis comprising administering a therapeutically effective amount of a compound according to claim 1 to a patient in need thereof.

19. A pharmaceutical composition comprising a compound according to claim 1 and a carrier, diluent, or excipient.

* * * * *